US010653797B2

(12) United States Patent
Ruoslahti et al.

(10) Patent No.: US 10,653,797 B2
(45) Date of Patent: May 19, 2020

(54) COMPOUNDS AND COMPOSITIONS FOR TARGETING BRAIN INJURIES AND METHODS OF USE THEREOF

(71) Applicant: SANFORD BURNHAM PREBYS MEDICAL DISCOVERY INSTITUTE, La Jolla, CA (US)

(72) Inventors: Erkki Ruoslahti, La Jolla, CA (US); Aman Mann, La Jolla, CA (US); Pablo Scodeller, La Jolla, CA (US); Sazid Hussain, La Jolla, CA (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 104 days.

(21) Appl. No.: 15/756,947

(22) PCT Filed: Sep. 2, 2016

(86) PCT No.: PCT/US2016/050168
§ 371 (c)(1),
(2) Date: Mar. 1, 2018

(87) PCT Pub. No.: WO2017/040976
PCT Pub. Date: Mar. 9, 2017

(65) Prior Publication Data
US 2018/0296696 A1 Oct. 18, 2018

Related U.S. Application Data

(60) Provisional application No. 62/213,168, filed on Sep. 2, 2015.

(51) Int. Cl.
| *A61K 47/62* | (2017.01) |
| *A61P 43/00* | (2006.01) |
| *C07K 5/10* | (2006.01) |
| *A61K 47/69* | (2017.01) |
| *A61K 9/51* | (2006.01) |
| *C07K 5/103* | (2006.01) |
| *A61K 47/64* | (2017.01) |
| *A61K 9/00* | (2006.01) |
| *A61K 48/00* | (2006.01) |

(52) U.S. Cl.
CPC ........ *A61K 47/6929* (2017.08); *A61K 9/0019* (2013.01); *A61K 9/5115* (2013.01); *A61K 47/62* (2017.08); *A61K 47/6425* (2017.08); *A61K 47/6923* (2017.08); *A61K 48/005* (2013.01); *A61K 48/0008* (2013.01); *A61P 43/00* (2018.01); *C07K 5/1013* (2013.01)

(58) Field of Classification Search
None
See application file for complete search history.

(56) References Cited

FOREIGN PATENT DOCUMENTS

| WO | WO-2008017517 A1 * | 2/2008 | ............. C07K 14/47 |
| WO | WO-2016059236 A1 * | 4/2016 | ......... A61K 39/0008 |

OTHER PUBLICATIONS

Chodobski et al (Transl Stroke Res 2: 492-516, 2011).*
Upadhyay RK, (Biomed Res Intl 2014, 1-37, 2014).*
Zhang et al (Biomat Sc 4, 219-229, 2016).*
Keener A, (The Scientist Mag, 1-12, Nov. 1, 2017).*
Mann et al (Nat Commun 7: 1-11, Jun. 28, 2016).*
PCT/US2016/050168 International Search Report and Written Opinion dated Dec. 12, 2016.
O'Loughliin et al. "Whey Protein Isolate Polydispersity Affects Enzymatic Hydrolysis Outcomes," Food Chemistry, May 2013, 141(3):2234-2342.
Chen et al. "Unique Molecular Signatures of Disease Brain Endothelia Provide a Novel Site for CNS-directed Enzyme Therapy," Nature Medicine, Oct. 2009, 15(10): 1215-1218.
Tuinstra et al. "Gene Delivery to Overcome Astrocyte Inhibition of Axonal Growth: An In Vitro Model of the Glial Scar," Biotechnology and Bioengineering, Mar. 2013, 110(3):947-957.
Wilems et al."Sustained Dual Drug Delivery of Anti-Inhibitory Molecules for Treatment of Spinal Cord Injury," Journal of Controlled Release, 2015, 213:103-111.
Lau et al. "Pathophysiology of the Brain Extracellular Matrix: A New Target of Remyelination," Nature Reviews Nueroscience, Oct. 2013, 14(10):722-729.

* cited by examiner

*Primary Examiner* — Daniel E Kolker
*Assistant Examiner* — Aditi Dutt
(74) *Attorney, Agent, or Firm* — Wagenknecht IP Law Group PC

(57) ABSTRACT

Disclosed are methods and compositions for selectively targeting sites of traumatic brain injury (TBI). A brain injury-specific 4-amino acid peptide (sequence CAQK), identified by in vivo phage display screening in mice with acute brain injury, shows selective binding to mouse and human brain injury lesions, and when systemically injected, specifically homes to sites of injury in penetrating and non-penetrating (controlled cortical impact) brain injury models. Also disclosed are methods and compositions for delivering therapeutic compounds to such sites. CAQK-coated nanoparticles containing silencing oligonucleotides provide an alternative to local delivery of therapeutics, which is invasive and can add complications to the injury.

20 Claims, 12 Drawing Sheets
Specification includes a Sequence Listing.

COMPOUNDS AND COMPOSITIONS FOR TARGETING BRAIN INJURIES AND METHODS OF USE THEREOF

CROSS-REFERENCE TO RELATED APPLICATIONS

This application is a national phase application of PCT/US2016/050168 filed Sep. 2, 2016, which claims priority to U.S. Provisional Application 62/213,168, filed Sep. 2, 2015 each of which is incorporated by reference in their entirety.

STATEMENT REGARDING FEDERALLY SPONSORED RESEARCH

This invention was made with Government support under Cooperative Agreement HR0011-13-2-0017 awarded by the Defense Advanced Research Projects Agency (DARPA). The Government has certain rights in the invention.

REFERENCE TO SEQUENCE LISTING

The Sequence Listing submitted on Sep. 2, 2016 as a text file named "SBMRI_16-002_PCT_ST25", created on Aug. 19, 2016, and having a size of 2,717 bytes is hereby incorporated by reference.

FIELD OF THE INVENTION

The disclosed invention relates generally to the fields of molecular medicine and brain biology and, more specifically, to molecules that selectively home to sites of acute brain injury.

BACKGROUND OF THE INVENTION

Acute brain injury such as traumatic brain injury (TBI) disrupts the normal function of the brain and generally has a poor prognosis for functional recovery and survival. Termed a 'silent epidemic', TBI is a leading cause of mortality and morbidity in children, teens and active adults from ages 1 to 44, with an annual incidence of 2.5 million in the US (Coronado et al., *J. Safety Res.* 43:299-307 (2012)). TBI can lead to acute and potentially long-lasting neurological dysfunction, including the development of chronic traumatic encephalopathy (CTE) or even Alzheimer's disease (Smith et al., *Nat. Rev. Neurology* 9:211-221 (2013)). A majority of combat-related TBI cases are additionally complicated by a penetrating injury to the brain, which is often even more difficult to manage than non-penetrating injuries (Bell et al., *J. Trauma* 66:S104-111 (2009)). Despite this substantial socio-economic impact, TBI treatment is limited to palliative care and no specific therapies with long-term benefits are available.

The blood-brain barrier (BBB) is considered a major impediment to systemic treatment of central nervous system (CNS) diseases. As a result, localized delivery of drugs within the brain has been explored, but it has limitations in clinical settings. In acute brain injury and several cerebrovascular diseases, including stroke, hypertension, and ischemia, the BBB is transiently disrupted, which allows extravascular access for macromolecules and neuroprotective drugs from the systemic circulation. In fact, the leakage of serum proteins into brain parenchyma is used to test for BBB integrity (Kuroiwa et al., *Acta Neuropathologica* 76:62-70 (1988)). However, lack of specific binding of passively accumulating proteins in the injured area can result in low retention and subsequent washout over time. Due to this clearance, the therapeutic efficacy of a systemically administered drug may be greatly limited.

Previous studies have used in vivo phage display to probe tissues in situ for specific molecular signatures and discovered homing peptides specific for different pathologies including tumors, atherosclerotic plaques, and wounds (Ruoslahti, *Nat. Rev. Cancer* 2:83-90 (2002); Ruoslahti, *Adv. Mater.* 24:3747-3756 (2012); Teesalu et al., *Methods Enzymol.* 503:35-56 (2012)). An acute and complex event such as TBI is suited for a similar approach as site-specific molecular changes in protein expression have been reported (Natale et al., *J. Neurotrauma* 20:907-927 (2003)).

Current approaches for delivering therapeutics to brain injury sites are invasive and can add complications to the injury.

It is an object of the present invention to provide peptides that recognize specific molecular changes at the sites of nervous system injury and enhance delivery of compounds and compositions to such sites.

It is another object of the present invention to provide peptides that selectively home to sites of nervous system injury.

It is another object of the present invention to provide compositions that selectively home to sites of nervous system injury.

It is another object of the present invention to provide methods for selectively targeting sites of nervous system injury.

It is another object of the present invention to provide methods for treating nervous system injury by selectively targeting sites of nervous system injury.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF SUMMARY OF THE INVENTION

The methods and compositions provided herein are based on the finding that a 4-amino acid peptide (CAQK) selectively recognizes brain injuries and accumulates at the sites of injury. This and other peptides containing the CAQK amino acid sequence were discovered to enhance the accumulation of systemically administered payloads with chemistries ranging in size from a drug-sized molecule to nanoparticles, and incorporating a variety of imaging and therapeutic functions of potential utility in clinical management of brain injuries. Importantly, the target of this delivery system is expressed both in mouse and human brain injuries.

The binding target for the CAQK peptide is a chondroitin sulfate proteoglycan (CSPG)-rich protein-carbohydrate extracellular matrix complex that is overexpressed in CNS injuries and is notably composed of hyaluronic acid, versican, aggrecan, brevican, neurocan, phosphacan, tenascin-R, and hyaluronan and proteoglycan link protein (Hapln). The overexpression of this complex results in the formation of a CSPG-rich glial scar, which is a major barrier to regeneration. This CSPG-rich extracellular matrix complex is also overexpressed in stroke and other nervous system injuries. Degradation of the complex is known to improve the outcome of stroke. CAQK-containing peptides were also shown to the site of injury in an experimental model of stroke caused by cerebral ischemia. Thus, the discovered peptides can selectively target sites of nervous system injury, especially those that overexpress CSPGs.

Disclosed are peptides, compositions, and methods for selective targeting nervous system injury, such as brain injury and stroke injury, sites of glial scar formation, and sites where hyaluronic acid, versican, tenascin-R, and Hapln are being deposited. The disclosed peptides, compositions, and methods are useful for selectively targeting acute nervous system injury, such as traumatic brain injury and stroke injury.

A peptide sequence that specifically homes to sites of nervous system injury has been discovered. Peptides containing the sequence home to, and can delivery large cargos to, sites of nervous system injury in the brain without regard to the blood brain barrier. This is likely due to compromise of the blood brain barrier in nervous system injury. The targeting and selectively homing are due to the presence of molecules at the site of nervous system injury to which the peptide sequence can bind.

Disclosed are peptides that contain the amino acid sequence CAQK (SEQ ID NO:4). In some forms, the peptides have any one or combinations of the following properties: selective homing to a site of nervous system injury; selective homing to a site of acute nervous system injury; selective homing to a site of brain injury; selective homing to a site of acute brain injury; selective homing to a site of stroke injury; selective homing to a site of acute stroke injury; specific binding to one or more of versican, tenascin-R, and Hapln; selective homing to a site of glial scar formation; selective homing to a site where hyaluronic acid, versican, tenascin-R, and Hapln are being deposited; and selective homing to CSPG-rich extracellular matrix complex.

In some forms, the peptide is 100 amino acids in length or less, 50 amino acids in length or less, 30 amino acids in length or less, 20 amino acids in length or less, 15 amino acids in length or less, 10 amino acids in length or less, 8 amino acids in length or less, 6 amino acids in length or less, 5 amino acids in length or less, or 4 amino acids in length. In some forms, the peptide is linear. In some forms, the peptide is circular.

In some forms of the peptide, the amino acid sequence CAQK (SEQ ID NO:4) is at the C terminal end of the peptide. In some forms, the peptide consists of the amino acid sequence CAQK (SEQ ID NO:4). In some forms, the peptide is modified. In some forms, the peptide is a methylated peptide. In some forms, the peptide includes a methylated amino acid segment. In some forms, the peptide is N- or C-methylated in at least one position.

Disclosed are compositions that include the disclosed peptide. In some forms, the composition includes the disclosed peptide and a cargo composition. In some forms of the composition, the peptide and the cargo composition are covalently coupled or non-covalently associated with each other. In some forms, the composition includes the disclosed peptide and a cargo molecule. In some forms of the composition, the peptide and the cargo molecule are covalently coupled or non-covalently associated with each other.

In some forms, the composition selectively homes to a site of acute brain injury. In some forms, the composition specifically binds to one or more of versican, tenascin-R, and Hapln. In some forms, the composition selectively homes to a site of glial scar formation. In some forms, the composition selectively homes to a site where hyaluronic acid, versican, tenascin-R, and Hapln are being deposited. In some forms, the composition selectively homes to CSPG-rich extracellular matrix complex. In some forms, the composition selectively homes to a site of acute brain injury, specifically binds to one or more of versican, tenascin-R, and Hapln, selectively homes to a site of glial scar formation, selectively homes to a site where hyaluronic acid, versican, tenascin-R, and Hapln are being deposited, selectively homes to CSPG-rich extracellular matrix complex, or combinations thereof.

In some forms, the cargo composition includes one or more cargo molecules. In some forms of the cargo composition, the cargo molecules each independently include a therapeutic agent, a therapeutic protein, a therapeutic compound, a therapeutic composition, a polypeptide, a nucleic acid molecule, a small molecule, a label, a labeling agent, a contrast agent, an imaging agent, a fluorophore, fluorescein, rhodamine, a radionuclide, indium-111, technetium-99, carbon-11, or carbon-13, or combinations thereof. In some forms of the cargo composition, at least one of the cargo molecules includes a therapeutic agent. In some forms of the cargo composition, at least one of the cargo molecules includes a functional nucleic acid. In some forms of the cargo composition, at least one of the cargo molecules includes a detectable agent.

In some forms, the cargo composition includes a surface molecule. In some forms, the cargo composition further includes a surface molecule. In some forms, the surface molecule includes a nanoparticle, a nanoworm, an iron oxide nanoworm, an iron oxide nanoparticle, an albumin nanoparticle, a liposome, a micelle, a phospholipid, a polymer, a microparticle, a bead, a virus, a phage, a viral particle, a phage particle, a viral capsid, a phage capsid, a virus-like particle, or a fluorocarbon microbubble. In some forms, the surface molecule includes a nanoparticle. In some forms of the composition, the cargo molecules are encapsulated in the nanoparticle.

In some forms, the composition includes a plurality of the cargo composition. In some forms, the composition includes a plurality of the peptide. In some forms of the composition, the peptide and the cargo composition are coupled via a linker.

Disclosed are compositions comprising a peptide and a cargo composition, where the peptide consists of the amino acid sequence CAQK (SEQ ID NO:4), where the cargo composition includes a surface molecule and cargo molecule, where the surface molecule includes a nanoparticle, where the cargo molecule is encapsulated in the nanoparticle, where the cargo molecule is a therapeutic agent, and where the therapeutic agent includes a functional nucleic acid.

The disclosed peptides and compositions are useful for selective targeting nervous system injury, such as brain injury and stroke injury, sites of glial scar formation, sites where hyaluronic acid, versican, tenascin-R, and Hapln are being deposited, and CSPG-rich extracellular matrix complexes. For example, the disclosed peptides and compositions are useful for selectively targeting acute nervous system injury, such as traumatic brain injury and stroke injury. Thus, methods for selectively targeting a cargo to a site of acute nervous system injury in a subject are disclosed.

In some forms, the method involves administering the disclosed composition to a subject having an acute nervous system injury. The composition selectively homes to a site of the nervous system injury in the subject thereby selectively targeting the cargo composition of the composition to the site of the nervous system injury.

In some forms, the nervous system injury includes a brain injury. In some forms, the peptide selectively homes to a site of the brain injury. In some forms, the brain injury includes traumatic brain injury, stroke injury, or both. In some forms, the peptide specifically binds to one or more of versican, tenascin-R, and Hapln. In some forms, the peptide selectively homes to a site of glial scar formation. In some forms, the peptide selectively homes to a site where hyaluronic acid, versican, tenascin-R, and Hapln are being deposited. In some forms, the peptide selectively homes to CSPG-rich extracellular matrix complex.

The composition can be administered by any suitable route. In some forms, the composition is administered intravenously. In some forms, the composition is administered systemically. In some forms, the composition is not administered locally.

The disclosed peptides and compositions are particularly useful for targeting acute nervous system injury. Thus, in some forms, the composition can be administered near the time of the injury or during the acute phase of the injury. In some forms, the composition is administered within 10 days of the onset of the nervous system injury. In some forms, the composition is administered within 5 days of the onset of the nervous system injury. In some forms, the composition is administered within 24 hours of the onset of the nervous system injury.

Disclosed in particular are methods of selectively targeting a cargo composition to a site of acute nervous system injury in a subject, where the method involves administering the composition to a subject having an acute nervous system injury, where the composition includes a peptide and a cargo composition, where the peptide consists of the amino acid sequence CAQK (SEQ ID NO:4), where the cargo composition includes a surface molecule and cargo molecule, where the surface molecule includes a nanoparticle, where the cargo molecule is encapsulated in the nanoparticle, where the cargo molecule is a therapeutic agent, and where the therapeutic agent includes a functional nucleic acid. The composition selectively homes to a site of the nervous system injury in the subject thereby selectively targeting the cargo composition of the composition to the site of the nervous system injury.

Also disclosed are methods of selectively targeting CSPG-rich extracellular matrix complexes (extracellular matrix containing hyaluronic acid, versican, tenascin-R, and Hapln and exemplified by the matrix of cultured U251 astrocytoma cells). The method can involve administering a composition to a subject, where the composition comprises a homing molecule and a pharmaceutically acceptable carrier. The composition selectively homes to the CSPG-rich extracellular matrix complex thereby selectively targeting the CSPG-rich extracellular matrix complex.

In some forms of the method, the homing molecule can specifically bind to one or more of versican, tenascin-R, and Hapln. In some forms of the method, the homing molecule can selectively home to a site where hyaluronic acid, versican, tenascin-R, and Hapln are being deposited. In some forms of the method, the homing molecule can selectively home to CSPG-rich extracellular matrix complex. In some forms of the method, the composition can be administered intravenously. In some forms of the method, the composition can be administered systemically.

In some forms of the method, the composition can further comprise a cargo composition. In some forms of the method, the cargo composition can include one or more cargo molecules. In some forms of the method, the cargo molecules can each independently be a therapeutic agent, a therapeutic protein, a therapeutic compound, a therapeutic composition, a polypeptide, a nucleic acid molecule, a small molecule, a label, a labeling agent, a contrast agent, an imaging agent, a fluorophore, fluorescein, rhodamine, a radionuclide, indium-111, technetium-99, carbon-11, or carbon-13, or combinations thereof. In some forms of the method, at least one of the cargo molecules comprises a therapeutic agent. In some forms of the method, at least one of the cargo molecules comprises a functional nucleic acid. In some forms of the method, at least one of the cargo molecules comprises a detectable agent.

Also disclosed are homing molecules that selectively home to CSPG-rich extracellular matrix complexes. In some forms, the homing molecules can be identified by bringing into contact the homing molecule and versican, tenascin-R, Hapln, or combinations thereof, and assessing whether the homing molecule specifically binds to the versican, tenascin-R, Hapln, or combination thereof. The homing molecule is identified if the homing molecule specifically binds to the versican, tenascin-R, Hapln, or combination thereof. In some forms, the homing molecules can be identified by bringing into contact the homing molecule and CSPG-rich extracellular matrix complexes, and assessing whether the homing molecule specifically binds to the CSPG-rich extracellular matrix complexes. The homing molecule is identified if the homing molecule specifically binds to the CSPG-rich extracellular matrix complexes. In some forms the CSPG-rich extracellular matrix complexes can be matrix produced by U251 astrocytoma cells.

Also disclosed are methods of identifying compounds that target sites of nervous system injury. The method can involve bringing into contact a test compound and versican, tenascin-R, Hapln, or combinations thereof, and assessing whether the test compound specifically binds to the versican, tenascin-R, Hapln, or combination thereof. The test compound is identified as a compound that target sites of nervous system injury if the test compound specifically binds to the versican, tenascin-R, Hapln, or combination thereof.

In some forms of the method, the versican, tenascin-R, Hapln, or combination thereof can be part of extracellular matrix. In some forms of the method, the extracellular matrix can be in or obtained from glial scar. In some forms, the extracellular matrix is CSPG-rich extracellular matrix complex (extracellular matrix containing hyaluronic acid, versican, tenascin-R, and Hapln and exemplified by the matrix of cultured U251 astrocytoma cells).

In some forms of the method, assessing whether the test compound specifically binds the versican, tenascin-R, Hapln, or combination thereof, can be accomplished by assessing whether the test compound specifically binds the CSPG-rich extracellular matrix complex. In some forms of the method, the extracellular matrix can be at a site of nervous system injury in test animal, where bringing into contact is accomplished by administering the test compound to the animal intravenously.

In some forms of the method, the versican, tenascin-R, Hapln, or combination thereof is not comprised in extracellular matrix. In some forms of the method, the versican, tenascin-R, Hapln, or combination thereof can be made from individual versican, tenascin-R, and Hapln proteins.

In some forms of the method, the test compound can be coupled to a label, wherein assessing whether the test compound specifically binds is accomplished by detecting the label.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 3A illustrates phage binding to extracellular matrix formed by U251 cells. The cells were gently dissociated and removed, and the remaining ECM was incubated with phage for 1 hour at room temperature, and phage binding was detected following an ELISA protocol. CAQK phage showed higher binding to ECM than control phage. FIG. 3B shows inhibition of CAQK phage binding to ECM by free CAQK peptide. FIG. 3C illustrates that phage binding to ECM is reduced upon enzymatic digestion of ECM with chondroitinase ABC or hyaluronidase. Mean±SEM. Representative data shown in FIGS. 3A, 3B, and 3C is from three experimental repetitions each with three sample replicates.

FIGS. 4B and 4C characterize CAQK peptide-conjugated porous silicon nanoparticles (CAQK-PSiNPs) using size distribution measured by dynamic light scattering (FIG. 4B); and photoluminescence spectra ($\lambda_{ex}$=365 nm) of PSiNP and CAQK-PSiNP (FIG. 4C; CAQK-PSiNP shows peak at ~530 nm while PSiNP does not). FAM label on the peptide appeared in the emission spectrum at ~530 nm and was included to allow estimation of conjugation efficiency to PSiNP, as described in the methods section. FIG. 4D shows release of siRNA from PSiNPs at different time points. Dy677-labeled siRNA was loaded into PSiNPs and incubated in PBS at 37° C. The released siRNA was obtained from supernatant at different time points.

FIG. 5A is a schematic of the experimental design for siRNA delivery. FIG. 5B is a graph showing signal-to-noise ratio (SNR) calculated for the peptide-conjugated PSiNPs in each mouse tissue (relative to PBS control) as described in the methods. CAQK-PSiNP showed significantly higher SNR in PBI brains than the control peptide-conjugated group (Mean±SD, *P<0.05, two-tailed Student's t test; n.s.—not significant, n=3). FIG. 5C is a graph showing percentage GFP/DAPI expression. Mean GFP intensity in injured hemisphere was normalized to corresponding contralateral hemisphere and plotted as percentage GFP expression (y-axis) (*P<0.05; ANOVA analysis, n=3). DAPI signal (plotted) showed similar total cell number. Mean±SEM, n.s., not significant.

FIGS. 6A and 6B show binding of CAQK-NPs to sections of the corpus callosum (FIG. 6A) and cortex (FIG. 6B) of human brains. Peptide-conjugated nanoparticles were incubated with formalin fixed frozen sections from injured and normal brains for ex vivo binding. Sections were counterstained with nuclear fast red, and the number of particles in each frame were counted and plotted in the graph. FIG. 6C illustrates versican expression in human brains. FIGS. 6D and 6E illustrate Hapln4 expression in the corpus callosum (FIG. 6D) and cortex (FIG. 6E) of human brains. Positive immunohistochemical staining was quantified and plotted. Mean±SEM, (ANOVA analysis; *P<0.05, P<0.005, *P<0.0005).

DETAILED DESCRIPTION OF THE INVENTION

Figure 1A:
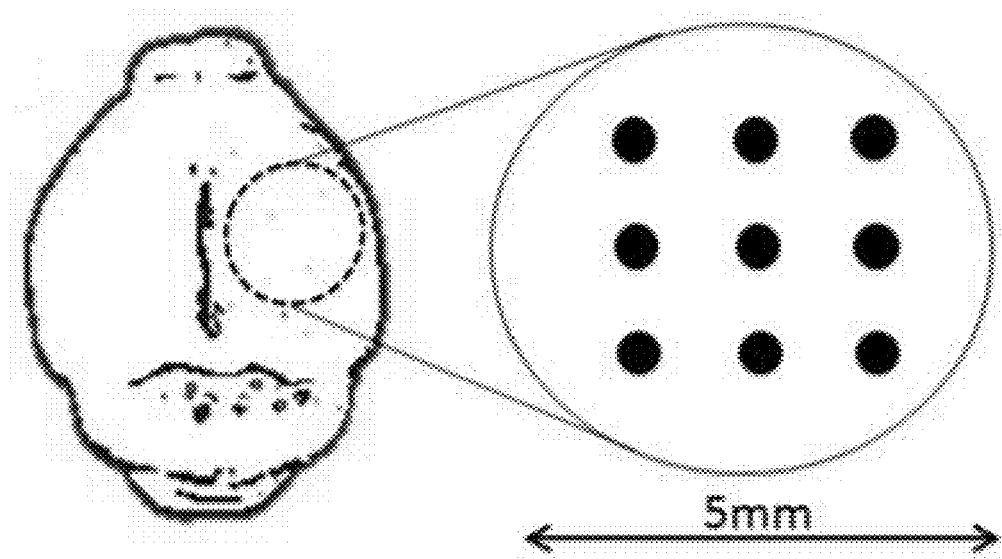
FIG. 1A illustrates a schematic of the PBI mouse model where a 5 mm craniotomy was performed in the right parietotemporal cortex and nine needle punctures were inflicted according to the grid shown.

The disclosed method and compositions may be understood more readily by reference to the following detailed description of particular embodiments and the Example included therein and to the Figures and their previous and following description.

A 4-amino acid peptide (CAQK) was discovered that selectively recognizes brain injuries and accumulates at the sites of injury. Peptides containing this sequence enhance the accumulation of systemically administered payloads with chemistries ranging in size from a drug-sized molecule to nanoparticles, and incorporating a variety of imaging and therapeutic functions for treatment of nervous system injuries. Importantly, the target of this delivery system is expressed both in mouse and human brain injuries. Peptides containing the sequence home to, and can delivery large cargos to, sites of nervous system injury in the brain without regard to the blood brain barrier. This is likely due to compromise of the blood brain barrier in nervous system injury. The targeting and selectively homing are due to the presence of molecules at the site of nervous system injury to which the peptide sequence can bind.

The binding target for the CAQK peptide is a chondroitin sulfate proteoglycan (CSPG)-rich protein-carbohydrate extracellular matrix complex that is overexpressed in CNS injuries and is notably composed of hyaluronic acid, versican, tenascin-R, and hyaluronan and proteoglycan link protein (Hapln). The targeted CSPG-rich extracellular matrix complexes generally are extracellular matrix containing hyaluronic acid, versican, tenascin-R, and Hapln and exemplified by the matrix of cultured U251 astrocytoma cells. The overexpression of this complex results in the formation of a CSPG-rich glial scar, which is a major barrier to regeneration. This CSPG-rich extracellular matrix complex is also overexpressed in stroke and other nervous system injuries. Degradation of the complex is known to improve the outcome of stroke. CAQK-containing peptides were also shown to the site of injury in an experimental model of stroke caused by cerebral ischemia. Thus, the discovered peptides can selectively target sites of nervous system injury, especially those that overexpress CSPGs.

Disclosed are peptides, compositions, and methods for selective targeting nervous system injury, such as brain injury and stroke injury, sites of glial scar formation, sites where hyaluronic acid, versican, tenascin-R, and Hapln are being deposited, and CSPG-rich extracellular matrix complexes. The disclosed peptides, compositions, and methods are useful for selectively targeting acute nervous system injury, such as traumatic brain injury and stroke injury.

Disclosed are peptides comprising the amino acid sequence CAQK (SEQ ID NO:4). In some forms, the peptides have any one or combinations of the following properties: selective homing to a site of nervous system injury; selective homing to a site of acute nervous system injury; selective homing to a site of brain injury; selective homing to a site of acute brain injury; selective homing to a site of stroke injury; selective homing to a site of acute stroke injury; specific binding to one or more of versican, tenascin-R, and Hapln; selective homing to a site of glial scar formation; selective homing to a site where hyaluronic acid, versican, tenascin-R, and Hapln are being deposited; and selective homing to CSPG-rich extracellular matrix complex.

Disclosed are compositions that include the disclosed peptide. In some forms, the composition includes the disclosed peptide and a cargo composition. In some forms of the composition, the peptide and the cargo composition are covalently coupled or non-covalently associated with each other. In some forms, the composition includes the disclosed peptide and a cargo molecule. In some forms of the composition, the peptide and the cargo molecule are covalently coupled or non-covalently associated with each other.

The disclosed peptides and compositions are useful for selective targeting nervous system injury, such as brain injury and stroke injury, sites of glial scar formation, sites where hyaluronic acid, versican, tenascin-R, and Hapln are being deposited, and CSPG-rich extracellular matrix complexes. For example, the disclosed peptides and compositions are useful for selectively targeting acute nervous system injury, such as traumatic brain injury and stroke injury. Thus, methods for selectively targeting a cargo to a site of acute nervous system injury in a subject are disclosed.

In some forms, the method involves administering the disclosed composition to a subject having an acute nervous system injury. The composition selectively homes to a site of the nervous system injury in the subject thereby selectively targeting the cargo composition of the composition to the site of the nervous system injury.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Materials

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a cargo molecule is disclosed and discussed and a number of modifications that can be made to a number of molecules including the cargo molecule are discussed, each and every combination and permutation of cargo molecule and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. CAQK Compositions

Disclosed are compositions that include the disclosed peptide. In some forms, the composition includes the disclosed peptide and a cargo composition. In some forms, the cargo composition includes one or more cargo molecules. In some forms, the cargo composition includes a surface molecule. In some forms, the composition includes the disclosed peptide and a surface molecule. In some forms, the cargo composition includes a surface molecule.

In some forms, the composition can include a plurality of surface molecules, a plurality of CAQK peptides and a plurality of cargo molecules. In some forms, the composition can include one or more surface molecules, a plurality of CAQK peptides and a plurality of cargo molecules. In some forms, the composition can include a plurality of surface molecules, one or more CAQK peptides and a plurality of cargo molecules. In some forms, the composition can include a plurality of surface molecules, a plurality of CAQK peptides and one or more cargo molecules. In some forms, the composition can include one or more surface molecules, one or more CAQK peptides and a plurality of cargo molecules. In some forms, the composition can include one or more surface molecules, a plurality of CAQK peptides and one or more cargo molecules. In some forms, the composition can include a plurality of surface molecules, one or more CAQK peptides and one or more cargo molecules.

In some forms, the composition can include a plurality of surface molecules, a plurality of CAQK peptides and a plurality of cargo compositions. In some forms, the composition can include one or more surface molecules, a plurality of CAQK peptides and a plurality of cargo compositions. In some forms, the composition can include a plurality of surface molecules, one or more CAQK peptides and a plurality of cargo compositions. In some forms, the composition can include a plurality of surface molecules, a plurality of CAQK peptides and one or more cargo compositions. In some forms, the composition can include one or more surface molecules, one or more CAQK peptides and a plurality of cargo compositions. In some forms, the composition can include one or more surface molecules, a plurality of CAQK peptides and one or more cargo compositions. In some forms, the composition can include a plurality of surface molecules, one or more CAQK peptides and one or more cargo compositions.

In some forms, the composition can include a surface molecule, a plurality of CAQK peptides and a plurality of cargo molecules, where one or more of the CAQK peptides and one or more of the cargo molecules are associated with the surface molecule. In some forms, the composition can include a surface molecule, a plurality of CAQK peptides and a plurality of cargo molecules, where a plurality of the plurality of CAQK peptides and a plurality of the plurality of cargo molecules are associated with the surface molecule. In some forms, the composition can include a surface molecule, a plurality of CAQK peptides and a plurality of cargo molecules, where the CAQK peptides and the cargo molecules are associated with the surface molecule.

In some forms, the composition can include a surface molecule, a plurality of CAQK peptides and a plurality of cargo compositions, where one or more of the CAQK peptides and one or more of the cargo compositions are associated with the surface molecule. In some forms, the composition can include a surface molecule, a plurality of CAQK peptides and a plurality of cargo compositions, where a plurality of the plurality of CAQK peptides and a plurality of the plurality of cargo compositions are associated with the surface molecule. In some forms, the composition can include a surface molecule, a plurality of CAQK peptides and a plurality of cargo compositions, where the CAQK peptides and the cargo compositions are associated with the surface molecule.

In some forms, the composition can include a surface molecule, where the surface molecule is multivalent for CAQK peptides and cargo molecules. In some forms, the composition can include a surface molecule, where the surface molecule is multivalent for CAQK peptides and includes one or more cargo molecules. In some forms, the composition can include a surface molecule, where the surface molecule is multivalent for cargo molecules and includes one or more CAQK peptides.

In some forms, the composition can include a surface molecule, where the surface molecule is multivalent for CAQK peptides and cargo compositions. In some forms, the composition can include a surface molecule, where the surface molecule is multivalent for CAQK peptides and includes one or more cargo compositions. In some forms, the composition can include a surface molecule, where the surface molecule is multivalent for cargo compositions and includes one or more CAQK peptides.

In some forms, the composition can include one or more copies of the peptide. In some forms, the composition can include at least 5 copies of the peptide. In some forms, the composition can include at least 10 copies of the peptide. In some forms, the composition can include at least 100 copies of the peptide. In some forms, the composition can include at least 1000 copies of the peptide. In some forms, the composition can include at least 10,000 copies of the peptide.

In some forms, the composition can include one or more copies of the cargo composition. In some forms, the composition can include at least 5 copies of the cargo composition. In some forms, the composition can include at least 10 copies of the cargo composition. In some forms, the composition can include at least 100 copies of the cargo composition. In some forms, the composition can include at least 1000 copies of the cargo composition. In some forms, the composition can include at least 10,000 copies of the cargo composition.

In some forms, the composition can include one or more copies of the cargo molecule. In some forms, the composition can include at least 5 copies of the cargo molecule. In some forms, the composition can include at least 10 copies of the cargo molecule. In some forms, the composition can include at least 100 copies of the cargo molecule. In some forms, the composition can include at least 1000 copies of the cargo molecule. In some forms, the composition can include at least 10,000 copies of the cargo molecule.

In some forms, the composition can include 1 copy of the surface molecule. In some forms, the composition can include at least 1 copy of the surface molecule. In some forms, the composition can include 2 copies of the surface molecule. In some forms, the composition can include at least 2 copies of the surface molecule. In some forms, the composition can include 3 copies of the surface molecule. In some forms, the composition can include at least 3 copies of the surface molecule. In some forms, the composition can include 4 copies of the surface molecule. In some forms, the composition can include at least 4 copies of the surface molecule. In some forms, the composition can include 5 copies of the surface molecule. In some forms, the composition can include at least 5 copies of the surface molecule. In some forms, the composition can include 10 copies of the surface molecule. In some forms, the composition can include at least 10 copies of the surface molecule.

In some forms, one or more of the cargo molecules can be conjugated to one or more of the CAQK peptides. In some forms, the CAQK peptides can be conjugated with a surface molecule. In some forms, the cargo molecules can be conjugated with a surface molecule. In some forms, one or more of the conjugated CAQK peptides can be indirectly conjugated to a surface molecule via a linker, one or more of the conjugated cargo molecules can be indirectly conjugated to the surface molecule via a linker, or both. In some forms, the composition can further include a plurality of linkers. In some forms, at least one of the linkers can include polyethylene glycol. In some forms, one or more of the conjugated cargo molecules and CAQK peptides can be covalently coupled. In some forms, one or more of the covalently coupled cargo molecules and CAQK peptides can include fusion peptides. In some forms, the CAQK peptides can be conjugated with a surface molecule. In some forms, one or more of the conjugated CAQK peptides can be directly conjugated to a surface molecule. In some forms, one or more of the conjugated CAQK peptides can be indirectly conjugated to a surface molecule. In some forms, one or more of the CAQK peptides can be covalently coupled to a surface molecule. In some forms, one or more of the covalently coupled CAQK peptides can be directly covalently coupled to a surface molecule. In some forms, one or more of the covalently coupled CAQK peptides can be indirectly covalently coupled to a surface molecule. In some forms, the cargo molecules can be conjugated with a surface molecule. In some forms, one or more of the conjugated cargo molecules are directly conjugated to a surface molecule. In some forms, one or more of the conjugated cargo molecules can be indirectly conjugated to a surface molecule. In some forms, one or more of the cargo molecules can be covalently coupled to a surface molecule. In some forms, one or more of the covalently coupled cargo molecules can be directly covalently coupled to a surface molecule. In some forms, one or more of the covalently coupled cargo molecules can be indirectly covalently coupled to a surface molecule.

In some forms, one or more of the cargo compositions can be conjugated to one or more of the CAQK peptides. In some forms, the CAQK peptides can be conjugated with a surface molecule. In some forms, the cargo composition includes a surface molecule and one or more cargo molecules. In some forms, the cargo compositions can be conjugated with the surface molecule. In some forms, one or more of the conjugated CAQK peptides can be indirectly conjugated to the surface molecule via a linker, one or more of the cargo peptides can be indirectly conjugated to the surface molecule via a linker, or both. In some forms, the composition can further include a plurality of linkers. In some forms, at least one of the linkers can include polyethylene glycol. In some forms, one or more of the cargo compositions and CAQK peptides can be covalently coupled. In some forms, one or more of the covalently coupled cargo compositions and CAQK peptides can include fusion peptides. In some forms, one or more of the conjugated CAQK peptides can be directly conjugated to the surface molecule. In some forms, one or more of the conjugated CAQK peptides can be indirectly conjugated to the surface molecule. In some forms, one or more of the CAQK peptides can be covalently coupled to the surface molecule. In some forms, one or more of the covalently coupled CAQK peptides can be directly covalently coupled to the surface molecule. In some forms, one or more of the covalently coupled CAQK peptides can be indirectly covalently coupled to the surface molecule.

In some forms, the disclosed compositions can have a therapeutic effect. In some forms, the therapeutic effect can be reducing damage of a nervous system injury. In some forms, the therapeutic effect can be increasing retention of nervous system function following a nervous system injury. In some forms, the subject can have one or more sites to be targeted, where the composition homes to one or more of the sites to be targeted. In some forms, the subject can have a site of nervous system injury, where the composition has a therapeutic effect at the site of nervous system injury.

B. CAQK Peptides

Disclosed are peptides that specifically home to sites of nervous system injury. These peptides include the amino acid sequence CAQK and the CAQK sequence is the only determinant of homing. These peptides can be referred to as CAQK peptides. Peptides containing the sequence home to, and can delivery large cargos to, sites of nervous system injury in the brain without regard to the blood brain barrier. This is likely due to compromise of the blood brain barrier in nervous system injury. The targeting and selectively homing are due to the presence of molecules at the site of nervous system injury to which the peptide sequence can bind. Generally, CAQK peptides will have any one or combinations of the following properties: selective homing to a site of nervous system injury; selective homing to a site of acute nervous system injury; selective homing to a site of brain injury; selective homing to a site of acute brain injury; selective homing to a site of stroke injury; selective homing to a site of acute stroke injury; specific binding to one or more of versican, tenascin-R, and Hapln; selective homing to a site of glial scar formation; selective homing to a site where hyaluronic acid, versican, tenascin-R, and Hapln are being deposited; and selective homing to CSPG-rich extracellular matrix complex.

In some forms, the peptide is 100 amino acids in length or less, 50 amino acids in length or less, 30 amino acids in length or less, 20 amino acids in length or less, 15 amino acids in length or less, 10 amino acids in length or less, 8 amino acids in length or less, 6 amino acids in length or less, 5 amino acids in length or less, or 4 amino acids in length. In some forms, the peptide is linear. In some forms, the peptide is circular.

In some forms of the peptide, the amino acid sequence CAQK (SEQ ID NO:4) is at the C terminal end of the peptide. In some forms, the peptide consists of the amino acid sequence CAQK (SEQ ID NO:4). In some forms, the peptide is modified. In some forms, the peptide is a methylated peptide. In some forms, the peptide includes a methylated amino acid segment. In some forms, the peptide is N- or C-methylated in at least one position.

Disclosed are peptides that include the amino acid sequence CAQK (SEQ ID NO:4). In some forms, the peptide can be a modified peptide. In some forms, the peptide can be a methylated peptide. In some forms, one or more of the methylated peptide can include a methylated amino acid segment. In some forms, the peptide can be N- or C-methylated in at least one position.

CAQK peptides are peptides that include the amino acid sequence CAQK (SEQ ID NO:4). CAQK peptides can be composed of standard amino acids with standard peptide linkages or can be embodied in other than standard amino acids and/or with other than standard peptide linkages. CAQK peptides can include modifications to the peptide, amino acids, and/or linkages. Examples of suitable modifications known to those in the art and are described elsewhere herein.

In some forms, the peptide can be comprised in a CAQK composition. In some forms, the CAQK composition can include one or more cargo compositions. In some forms, the CAQK composition can include one or more cargo molecules. In some forms, the peptide can be comprised in a CAQK conjugate. In some forms, the CAQK conjugate can include one or more cargo compositions. In some forms, the CAQK conjugate can include one or more cargo molecules. In some forms, the composition can include a plurality of cargo compositions. In some forms, the composition can include a plurality of cargo molecules. In some forms, the composition can include a plurality of copies of the peptide.

The disclosed peptides, including CAQK peptides, can have a length of up to 10, 20, 30, 40, 50, 100, 150, 200, 250, 300, 400, 500, 1000 or 2000 residues. In forms, the peptides can have a length of at least 7, 8, 9, 10, 15, 20, 25, 30, 40, 50, 60, 70, 80, 90, 100 or 200 residues. In some forms, the peptides can have a length of 7 to 200 residues, 7 to 100 residues, 7 to 90 residues, 7 to 80 residues, 7 to 70 residues, 7 to 60 residues, 7 to 50 residues, 7 to 40 residues, 7 to 30 residues, 7 to 20 residues, 7 to 15 residues, 7 to 10 residues, 8 to 200 residues, 8 to 100 residues, 8 to 90 residues, 8 to 80 residues, 8 to 70 residues, 8 to 60 residues, 8 to 50 residues, 8 to 40 residues, 8 to 30 residues, 8 to 20 residues, 8 to 15 residues, 8 to 10 residues, 9 to 200 residues, 9 to 100 residues, 9 to 90 residues, 9 to 80 residues, 9 to 70 residues, 9 to 60 residues, 9 to 50 residues, 9 to 40 residues, 9 to 30 residues, 9 to 20 residues, 9 to 15 residues, 9 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 10 to 15 residues, 15 to 200 residues, 15 to 100 residues, 15 to 90 residues, 15 to 80 residues, 15 to 70 residues, 15 to 60 residues, 15 to 50 residues, 15 to 40 residues, 15 to 30 residues, 15 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

CAQK peptides can be composed of, for example, amino acids, amino acid analogs, peptide analogs, amino acid mimetics, peptide mimetics, etc. Although structures, design, etc. of CAQK peptides is described herein in terms of amino acids and peptides composed of amino acids for convenience, it is understood that analogous analogs, mimetics, modified forms, etc. of amino acids and peptides can also be used as CAQK peptides and designed using similar principles.

Bonds and modifications to amino acids that can reduce or eliminate protease cleavage at a bond are known and can be used in the disclosed peptides, including CAQK peptides. For example, the stability and activity of peptides can be increased by protecting some of the peptide bonds with N-methylation or C-methylation. Methylated peptides are peptides containing a non-natural methyl group. Peptides can be methylated at nitrogens (N-methylated peptides), carbons (C-methylated peptides), and sulfur (S-methylated peptides). When a portion of a peptide is methylated the portion that is methylated can be referred to as a methylated amino acid segment.

A variety of chemical modification techniques and moieties are described in, for example, U.S. Pat. Nos. 5,554,728, 6,869,932, 6,828,401, 6,673,580, 6,552,170, 6,420,339, U.S. Pat. Pub. 2006/0210526 and Intl. Pat. App. WO 2006/136586. Some examples of such modifications include peptide bond surrogates such as those described in Cudic and Stawikowski, Peptidomimetics: Fmoc Solid-Phase Pseudo-peptide Synthesis, in Methods in Molecular Biology, vol. 294, 223-246 (2008), and chemical modifications, such as maleimide capping, polyethylene glycol (PEG) attachment, maleidification, acylation, alkylation, esterification, and amidification, to produce structural analogs of the peptide.

The disclosed peptides can be made in the form of stabilized peptides and/or formulated as long-circulating forms. For example, a polyethylene glycol conjugate can be used. The disclosed peptides can also be administered over a period of time. For example, peptides can be delivered with an osmotic pump. This can extend the permeability of the target cells and tissues. Modified forms of peptides can be used. For example, peptides can be methylated (which can stabilize the peptides against proteolysis).

It is understood that there are numerous amino acid and peptide analogs which can be incorporated into the disclosed peptides. For example, there are numerous D amino acids or other non-natural amino acids which can be used. The opposite stereoisomers of naturally occurring peptides are disclosed, as well as the stereo isomers of peptide analogs. These amino acids can readily be incorporated into polypeptide chains by chemical synthesis or by charging tRNA molecules with the amino acid of choice and engineering genetic constructs that utilize, for example, amber codons, to insert the analog amino acid into a peptide chain in a site specific way (Albericio, F. (2000). *Solid-Phase Synthesis: A Practical Guide* (1 ed.). Boca Raton: CRC Press; Nilsson B L, Soellner M B, Raines R T (2005). "Chemical Synthesis of Proteins". *Annu. Rev. Biophys. Biomol. Struct.* 34: 91-118; Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH=CH— (cis and trans), —$COCH_2$—, —CH(OH)$CH_2$—, and —$CHH_2SO$. These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—$CHH_2$—S); Hann J. Chem. Soc Perkin Trans. I 307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appin, EP 45665 CA (1982): 97:39405 (1982) (—CH(OH)$CH_2$—); Holladay et al. Tetrahedron. Lett 24:4401-4404 (1983) (—C(OH)$CH_2$—); and Hruby Life Sci 31:189-199 (1982) (—$CH_2$—S—); each of which is incorporated herein by reference. A particularly useful non-peptide linkage is —$CH_2NH$—. It is understood that peptide analogs can have more than one atom between the bond atoms, such as b-alanine, g-aminobutyric acid, and the like.

Amino acid analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides as long as activity is preserved. Cysteine residues can be used to cyclize or attach two or more peptides together. This can be beneficial to constrain peptides into particular conformations (Rizo and Gierasch Ann. Rev. Biochem. 61:387 (1992), incorporated herein by reference).

The disclosed compositions can include or use the disclosed CAQK peptides in various forms, including peptides and peptidomimetics as disclosed. For convenience of expression, in many places herein the use or inclusion of peptides will be recited. It is understood that, in such cases, it is considered that CAQK peptides in various forms can also be used or included in the same or similar ways as is described in terms of peptides, and such use and inclusion is specifically contemplated and disclosed thereby.

As used herein, the term "peptide" is used broadly to mean peptides, proteins, fragments of proteins and the like. Peptides are a class of compounds composed of amino acids chemically bound together. In general, the amino acids are chemically bound together via amide linkages (CONH) in peptides. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as that from which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861). In some forms of peptidomimetics, amino acids can be bound together by chemical bonds other than amide linkages, as is known in the art. For example, the amino acids may be bound by amine linkages. The C-terminal end of a peptide refers to the end of the peptide having the peptide's terminal carboxyl group. This is the last amino acid of the peptide when considered from the N to C orientation of the peptide. The CAQK peptide is further describes and defined elsewhere herein.

As used herein, the term "non-natural amino acid" refers to an organic compound that has a structure similar to a natural amino acid so that it mimics the structure and reactivity of a natural amino acid. The non-natural amino acid as defined herein generally increases or enhances the properties of a peptide (e.g., selectivity, stability) when the non-natural amino acid is either substituted for a natural amino acid or incorporated into a peptide.

As used herein, the term "homing molecule" means any molecule that selectively homes in vivo to specific cells or specific tissue in preference to normal tissue. Similarly, the term "homing peptide" or "homing peptidomimetic" means a peptide that selectively homes in vivo to specific cells or specific tissue in preference to normal tissue. It is understood that a homing molecule that selectively homes in vivo to specific cells or specific tissue or can exhibit preferential homing to r specific cells or specific tissue. The CAQK peptide is an example of a homing molecule.

As used herein, "selectively homes" means that, in vivo, the homing molecule binds preferentially to the target as compared to non-target. For example, the homing molecule can bind preferentially to targets at sites of nervous system injury, as compared to normal or non-injured tissue. Selective homing to, for example, a site of nervous system injury generally is characterized by at least a two-fold greater localization at the site of nervous system injury, as compared to several non-nervous system tissue types or to non-injured nervous system tissue. A homing molecule can be characterized by, for example, 5-fold, 10-fold, 20-fold or more preferential localization to the target as compared to one or more non-targets. For example, a homing molecule can be characterized by, for example, 5-fold, 10-fold, 20-fold or more preferential localization to a site of nervous system injury as compared to several non-nervous system tissue types or to non-injured nervous system tissue, or as compared to most or all non-nervous system tissue. Thus, it is understood that, in some cases, a homing molecule, such as the CAQK peptide, homes, in part, to one or more normal organs or one or more normal tissues in addition to homing to the target tissue. Selective homing can also be referred to as targeting. The molecules, proteins, cells, tissues, etc. that are targeted by homing molecules can be referred to as targets, targeted molecules, proteins, cells, tissues, etc.

C. Cargo Compositions

Cargo compositions are molecules or compositions that are associated with the disclosed peptides in a composition. Doing so allows the peptide to mediate targeting and homing of the cargo composition to the target of the peptide (e.g., a site of nervous system injury). The cargo composition is or contains a cargo that is desired to be targeted to site of a nervous system injury. The cargo composition can be a cargo molecule or a plurality of cargo molecules. Or the cargo composition can be a surface molecule. Or the cargo composition can include one or more cargo molecules and one or more other components, such as a surface molecule. In this way, cargo compositions are generally defined by their components and their association (and administration) with the disclosed peptides. Cargo composition can include one or more cargo molecules. Cargo compositions can include two or more different cargo molecules.

1. Cargo Molecules

Cargo molecules are any molecule that is associated with a disclosed peptide. The association can be direct or indirect and covalent or non-covalent. Generally, cargo molecules are molecules that are desired to be targeted to site of a nervous system injury.

The disclosed compositions can include one or more cargo molecules. Generally, the disclosed compositions can include a plurality of cargo molecules. The disclosed compositions can include a single type of cargo molecule or a plurality of different types of cargo molecules. Thus, for example, the disclosed compositions can include a plurality of different types of cargo molecules where a plurality of one or more of the different types of cargo molecules can be present.

Cargo molecules can be or can include, for example, therapeutic agents, therapeutic proteins, therapeutic compounds, therapeutic compositions, polypeptides, nucleic acid molecules, functional nucleic acids, small molecules, detectable agents, labels, labeling agents, contrast agents, imaging agents, fluorophores, fluorescein, rhodamine, radionuclides, Lutetium-177 ($^{177}$Lu), Rhenium-188 ($^{188}$Re), Gallium-68 ($^{68}$Ga), Yttrium-90 ($^{90}$Y), Technetium-99m ($^{99m}$Tc), Holmium-166 ($^{166}$Ho), Iodine-131 ($^{131}$I), Indium-111 ($^{111}$In), Flourine-18 ($^{18}$F), Carbon-11 ($^{11}$C), Carbon-13 ($^{13}$C), Nitrogen-13 ($^{13}$N), Oxygen-15 ($^{15}$O), Bromine-75 ($^{75}$Br), Bromine-76 ($^{76}$Br), Iodine-124 (124I), Thalium-201 ($^{201}$Tl), Technetium-99 ($^{99}$Tc), Iodine-123 ($^{123}$I). This is a non-exclusive and a non-inclusive list. Any molecule that is desired to be targeted to a site of nervous system injury can be a cargo molecule.

Cargo molecules can be associated with and arranged in the compositions in a variety of configurations. In some forms, cargo molecules can be associated with, conjugated to, and/or covalently coupled to a plurality of surface molecules. In some forms, cargo molecules can be associated with, conjugated to, and/or covalently coupled to a plurality of CAQK peptides. In some forms, cargo molecules can be associated with, conjugated to, and/or covalently coupled to a plurality of CAQK peptides, where the CAQK peptides can be associated with, conjugated to, and/or covalently coupled to a plurality of surface molecules. Combinations of these combinations can also be used.

i. Therapeutic Agents for Nervous System Injuries

A significant use of the disclosed compositions that target and home to nervous system injuries is to deliver cargo molecules to sites of nervous system injury. Therapeutic agents are a particularly useful cargo molecule to delivery to sites of nervous system injury. A number of therapeutic agents are known for effects that would be useful at the sites of nervous system injury, some of which are described below.

a. Statins

Statins form a class of lipid-lowering medications that inhibit the enzyme HMG-CoA reductase, which plays a central role in the production of cholesterol. However, statins also exhibit pleiotropic properties that make them potentially attractive neuroprotective agents. Preclinical studies demonstrate that statins target multiple secondary injury pathways and improve functional outcome after experimental TBI (Wang et al., *Exp. Neurol.* 206:59-69 (2007)). Statins decrease apoptosis after trauma and favorably alter the ratio of anti-apoptotic to apoptotic factors (Lu et al. *J. Neurotrauma* 24:1132-1146 (2007)). Studies show that statins may also promote the growth and differentiation of new neurons and upregulate neurotrophic factors, including BDNF and vascular endothelial growth factor (VEGF) (Wu et al., *J. Neurotrauma* 25:130-139 (2008); Chen et al., *J. Cereb. Blood Flow. Metab.* 25:281-290 (2005)). TBI models have also revealed that statins limit the production of inflammatory mediators, glial cell activation and cerebral edema, while increasing the integrity of the blood brain barrier (Chen et al., *J. Cereb. Blood Flow. Metab.* 25:281-290 (2005)). However, statins can cause life-threatening muscle damage known as rhabdomyolysis, which can cause severe muscle pain, liver damage, kidney failure, and death. Statins are also known to have effects on the coagulation and fibrinolytic systems, which may be the basis of their protective effects in cardiovascular disease (Jansen et al., *Crit. Care* 17:227 (2013)).

b. Progesterone

Progesterone is an endogenous steroid and progestogen sex hormone, whose receptors are expressed in the CNS of both males and females. Progesterone has been shown to have neuroprotective effects in experimental spinal cord injury (SCI), stroke and TBI (Gonzalez Deniselle et al., *J. Steroid Biochem. Mol. Biol.* 83:199-209 (2002); Jiang et al., *Brain Res.* 735:101-107 (1996); Roof et al., *J. Neurotrauma* 17:367-388 (2000)). However, recent reports question its effectiveness in trauma models. A systematic review of progesterone treatment in CNS injury raised concerns about the methodological quality of the TBI studies, and quantitative evaluation revealed possible experimental bias in these studies (Gibson et al., *Brain* 131:318-328 (2008)). Additionally, no protective effects of progesterone were observed at doses previously reported to be effective by others, in well characterized models of either TBI or SCI (Fee et al., *Brain Res.* 1137:146-152 (2007); Gilmer et al., *J. Neurotrauma* 25:593-602 (2008)). These data suggest that the use of progesterone for treating TBI is still questionable.

c. Cyclosporine A

The early effects of TBI include metabolic crises such as mitochondrial failure. Mitochondrial failure leads to energy and ionic imbalances, reduced brain ATP levels, changes in mitochondrial permeability transition, release of cytochrome c and induction of pro-apoptotic events (Mazzeo et al., *Exp. Neurol.* 218:363-370 (2009)). Cyclosporine A (also known as cyclosporin), is an immunosuppressant drug widely used in organ transplantation to prevent rejection. Cyclosporine A has been shown to attenuate mitochondrial failure by binding to cyclophilin D and stabilizing the mitochondrial permeability transition pore (Szabo et al., *J. Biol. Chem.* 266:3376-3379 (1991)). Treatment with Cyclosporine A reduced axonal damage in diffuse axonal injury models and decreased lesion size following controlled cortical impact in TBI (Okonkwo et al., *J. Cereb. Blood Flow Metab.* 19:443-451 (1999); Sullivan et al., *Neuroscience* 101:289-295 (2000)).

Despite such advantages, Cyclosporine A shows relatively poor brain penetration, it has a biphasic drug-response curve, and prolonged use adversely impacts the immune system (Margulies et al., *J. Neurotrauma* 26:925-939 (2009)).

d. Diketopiperazines etopiperazines are cyclized dipeptides that were developed based on the tripeptide thyrotropin-releasing hormone. Thyrotropin-releasing hormone and its analogs inhibit multiple secondary injury factors and processes, proving to be highly neuroprotective in experimental neurotrauma (Pitts et al., *Neurotrauma* 12:235-243 (1995)). Four structurally different diketopiperazines demonstrated significant neuroprotective properties both in vitro and in animal TBI studies, one of which (35b) showed effectiveness across TBI models and species. In neuronal cell cultures, 35b provided neuroprotection in multiple models of necrotic and apoptotic cell death, reducing apoptotic cell death (Faden et al., *J. Cereb. Blood Flow Metab.* 23:342-354 (2003)). Given their safety profile and their multipotential neuroprotective effects in experimental TBI models, diketopiperazines are attractive candidates for TBI therapy.

e. Substance P Antagonists

Blood brain barrier disruption is an important contributor to secondary injury following TBI, and therapies to restore blood brain barrier functionality are under investigation for neuroprotection. The localized permeability of the blood brain barrier and the delayed onset of secondary injury provide a window of opportunity for therapeutic intervention. The duration of the blood brain barrier impairment is at least up to five days (Cunningham et al., *J. Neurotrauma* 31:505-514 (2014)). Within this time window, affinity ligand-based (synaphic) targeting can be an effective drug delivery approach, with results showing as high as 35-fold enhancement in the accumulation of systemically administered imaging agents and therapeutics at and around the site of injury.

Substance P is released early following trauma as part of a neurogenic inflammatory response. Inhibition of post-traumatic substance P activity, either by preventing substance P release or by antagonism of the neurokinin-1 receptor, reduced inflammation associated with acute TBI and maintained the integrity of the blood brain barrier (Nimmo et al., *Neuropeptides* 38:40-47 (2004)). Furthermore, administration of substance P antagonists decreased blood brain barrier permeability and edema formation, reduced axonal injury, enhanced neuronal survival and improved behavioral outcomes following experimental TBI (Donkin et al., *Curr. Opin. Neurol.* 23:293-299 (2010); Donkin et al., *J. Cereb. Blood Flow Metab.* 29:1388-1398 (2009)). An evaluation of the therapeutic window, along with further investigation in additional animal models and species is needed.

f. SUR1-regulated $NC_{ca-ATp}$ Channel Inhibitors

Edema and progressive secondary hemorrhage are important secondary injury mechanisms that contribute to neurological impairments in patients after TBI. Studies suggest that upregulation of sulfonylurea receptor 1 (SUR1)-regulated $NC_{ca-ATp}$ channels in microvascular endothelium plays a key role in secondary injury pathways (Simard et al., *Curr. Opin. Pharmacol.* 8:42-49 (2008)). Glibenclamide, an antidiabetic drug in the class of medications known as sulfonylureas, also functions as a SUR1 inhibitor, leading to a reduction in edema, secondary hemorrhage, inflammation, apoptosis, and lesion size in experimental TBI and subarachnoid hemorrhage models (Simard et al., *J. Cereb. Blood Flow Metab.* 29:317-330 (2009); Simard et al., *J. Neurotrauma* 26:2257-2267 (2009)). Glibenclamide treatment was also shown to improve functional recovery after TBI (Simard et al., *J. Neurotrauma* 26:2257-2267 (2009)).

g. Cell Cycle Inhibitors

Upregulation of cell cycle proteins occurs in both mitotic (astrocytes and microglia) and post-mitotic (neurons, oligodendroglia) cells after CNS injury, and is associated with caspase-mediated neuronal apoptosis and glial proliferation after TBI (Di Giovanni et al., *PNAS* 102:8333-8338 (2005)). Cell cycle inhibitors have been extensively evaluated in cancer, but have also been shown to be strongly neuroprotective in vivo. Inhibitors of the cell cycle, such as flavopiridol, a semi-synthetic flavonoid, and the purine analogues roscovitine and olomoucine, exert powerful neuroprotective effects in various models of neuronal cell death, as well as inhibitory effects on the proliferation and activation of astrocytes and microglia (Di Giovanni et al., *PNAS* 102: 8333-8338 (2005); Cernak et al., *Cell Cycle* 4:1286-1293 (2005); Verdaguer et al., *J. Pharmacol. Exp. Ther.* 308:609-616 (2004)). Intracerebroventricular administration of flavopiridol (an inhibitor of all major cyclic-dependent kinases) after fluid percussion injury in rats reduced lesion volume by approximately 70% and improved cognitive and sensorimotor recovery to the level of uninjured controls. In addition, flavopiridol markedly reduced glial cell activation, and these changes were associated with suppression of cell cycle proteins in neurons, astrocytes, and microglia. Furthermore, delayed administration of flavopiridol had similar neuroprotective effects; with systemic intraperitoneal treatment given 24 hours post-trauma causing a significant reduction in lesion volumes (Cernak et al., *Cell Cycle* 4:1286-1293 (2005)).

Roscovitine in particular, is a very selective cell cycle inhibitor. In addition to improving functional recovery and mediating a reduction in lesion size, central administration of roscovitine reduced astrogliosis and produced a marked inhibition of microglial-mediated neuroinflammation (Hilton et al., *J. Cereb. Blood Flow Metab.* 28:1845-1859 (2008)). Protective effects of cell cycle inhibitors have also been demonstrated after experimental spinal cord injury and stroke (Byrnes et al., *Brain* 130:2977-2992 (2007); Osuga et al., *PNAS* 97:10254-10259 (2000)). However, the toxicity of these cell cycle inhibitors presents a major disadvantage.

h. Cell-Based Therapies

Endogenous therapeutic stem cell strategies focus on increasing mobilization, longevity, and production of neural stem cells in the subventricular zone and dentate gyrus (George et al., *Neuron* 87:297-309 (2015)). While the brain has a limited capacity for regeneration, endogenous neural stem cells, as well as numerous pro-regenerative molecules, can participate in replacing and repairing damaged or diseased neurons and glial cells. One particular benefit of using endogenous regeneration is the avoidance of the host immune response.

Exogenous stem cell treatments refer to transplanted cells from another source into a patient. Exogenous stem cells have been delivered to the brain via the blood stream or direct transplantation and have shown great promise in animal models to enhance stroke recovery. Exogenous stem cells are typically divided into three categories: (1) immortalized cell lines, (2) neural progenitor cells or neural stem cells, and (3) bone marrow-derived hematopoietic/endothelial progenitors and stromal cells (Bliss et al., *Neurobiol. Dis.* 37:275-283 (2010)). Immortalized cell lines have been developed from tumor cells or from manipulation with oncogenes. NT2N cells, which are derived from teratocarcinoma, differentiate into post-mitotic neuron-like cells with the addition of retinoic acid and mitotic inhibitors, and have been shown to improve outcome in several ischemic models (Saporta et al., *Neuroscience* 91:519-525 (1999)). ReNeuron's cells, which were engineered to be immortalized only in the presence of tamoxifen to reduce the risk of tumor formation, have shown dose-dependent recovery in stroke rodent models (Stroemer et al., *Neurorehabil. Neural. Repair.* 23:895-909 (2009); Stroemer et al., Front Biosci. 13:2290-2292 (2008)).

Human neural progenitor cells are derived from embryonic and fetal tissue and have the ability to produce astrocytes, neurons, and oligodendrocytes (Gage, *Science* 287: 1433-1438 (2000)). In stroke models, neural progenitor cells are able to migrate to the injured regions and improve recovery (Zhang et al., *Nat. Biotechnol.* 19:1129-1133 (2001)). Progenitor cells derived from bone marrow, umbilical cord blood and adipose tissue have all been shown to improve recovery in stroke models (Shen et al., *J. Cereb. Blood Flow Metab.* 27:6-13 (2007)).

The discovery of induced pluripotent stem (iPS) cells created a paradigm shift in cell therapy, as it allowed researchers to bypass many of the concerns of traditional stem cell therapy, such as ethical concerns, supply limitations, and the possible requirement of immunosuppression (Meissner et al., *Nat. Biotechnol.* 25:1177-1181 (2007)). Developments in this field have included vector- and transgene-free techniques to derive iPS cells that improve functional outcome after brain ischemia (Mohamad et al., *PLoS One* 8:e64160 (2013)).

However, the precise mechanism of action of stem cell therapeutics remains elusive, thus limiting the design of trials and applications.

i. siRNA Treatment

Previous studies on siRNA therapy of brain injuries have either used direct injection into the CNS space or silenced a target present in the brain endothelial cells (Fukuda et al., *Genes* 4:435-456 (2013)). A number of targets for gene silencing, such as Bcl-2 family proteins, caspases, histone deacetylases (HDACs), and phosphatase and tensin homolog (PTEN), have been suggested for brain injury treatment.

The Bcl-2 family of proteins is localized to the outer membrane of mitochondria, where it can either be pro-apoptotic or anti-apoptotic, making it an important apoptosis regulator. As discussed above, secondary injury in TBI can trigger pro-apoptotic events. Therefore, the use of Bcl-2 inhibitors might be a good strategy in treating TBI and stroke. Bcl-2 inhibitors include the antisense oligonucleotide drug Genasense, the small molecule inhibitor compounds ABT-737 and ABT-263, and the small molecule oral drug Venetoclax.

Caspases are a family of protease enzymes that play essential roles in programmed cell death and inflammation. Other recently identified roles of caspases include cell proliferation, tumor suppression, cell differentiation, neural development and axon guidance and aging (Shalini et al., *Cell Death Diff.* 22:526-539 (2015)). As excessive programmed cell death is a prominent feature in neurodegenerative diseases, caspases make a good target in the treatment of TBI.

Histone deacetylases (HDAC) are a class of enzymes that remove acetyl groups from amino acids on histones, allowing the histones to wrap the DNA more tightly. HDACs are involved in various gene regulation pathways including signal transduction, cell cycle, and cancer pathways. Deregulation of histone modification has been implicated in neurological and psychological disorders such as Schizophrenia and Huntington's disease (Lee et al., *Neurotherapeutics* 10:664-676 (2013)). Accordingly, some studies suggest that HDAC inhibitors have therapeutic benefits in various neurological and psychiatric disorders (Grayson et al., *Mol. Pharm.* 77:126-135 (2010)). However, since many neurological disorders only affect specific brain regions, an understanding of the specificity of HDACs is imperative before further investigation for their use in TBI therapy.

Phosphatase and tensin homolog (PTEN) is a protein that seems to act primarily as a tumor suppressor. However, its absence has also been implicated in nerve regeneration in mice, thus making it an attractive target for inhibition in treating TBI (Liu et al., *Nat. Neurosci.* 13:1075-1081 (2010)).

ii. Functional Nucleic Acids

Cargo molecules can be functional nucleic acids. Functional nucleic acids are nucleic acid molecules that have a specific function, such as binding a target molecule, serving as an enzyme substrate or cofactor, or catalyzing a specific reaction. For example, functional nucleic acids can bind a target nucleic acid (RNA or DNA) or can serve as enzyme substrate-guiding sequence (or guide). Functional nucleic acid molecules can be divided into the following categories, which are not meant to be limiting. For example, functional nucleic acids include antisense molecules, aptamers, ribozymes, triplex forming molecules, RNA interference (RNAi), CRISPR (Clustered Regularly Interspaced Short Palindromic Repeats) RNA (crRNA), and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Often functional nucleic acids are designed to interact with other nucleic acids based on sequence complementarity between the target molecule and the functional nucleic acid molecule. In other situations, the specific recognition between the functional nucleic acid molecule and the target molecule is not based on sequence complementarity between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNase H mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$. A representative sample of methods and techniques which aid in the design and use of antisense molecules can be found in U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Triplex forming functional nucleic acid molecules are molecules that can interact with either double-stranded or single-stranded nucleic acid.

When triplex molecules interact with a target region, a structure called a triplex is formed, in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than 10-6, 10-8, 10-10, or 10-12. Representative examples of how to make and use triplex forming molecules to bind a variety of different target molecules can be found in U.S. Pat. Nos. 5,176,996, 5,645,985, 5,650,316, 5,683,874, 5,693,773, 5,834,185, 5,869,246, 5,874,566, and 5,962,426.

Gene expression can also be effectively silenced in a highly specific manner through RNA interference (RNAi). This silencing was originally observed with the addition of double stranded RNA (dsRNA) (Fire, A., et al., Nature, 391:806-11 (1998); Napoli, C., et al., Plant Cell, 2:279-89 (1990); Hannon, G. J., Nature, 418:244-51 (2002)). Once dsRNA enters a cell, it is cleaved by an RNase III—like enzyme, Dicer, into double stranded small interfering RNAs (siRNA) 21-23 nucleotides in length that contain 2 nucleotide overhangs on the 3' ends (Elbashir, S. M., et al., Genes Dev., 15:188-200 (2001); Bernstein, E., et al., Nature, 409: 363-6 (2001); Hammond, S. M., et al., Nature, 404:293-6 (2000)). In an ATP-dependent step, the siRNAs become integrated into a multi-subunit protein complex, commonly known as the RNAi induced silencing complex (RISC), which guides the siRNAs to the target RNA sequence (Nykanen, A., et al., Cell, 107:309-21 (2001)). At some point the siRNA duplex unwinds, and it appears that the antisense strand remains bound to RISC and directs degradation of the complementary mRNA sequence by a combination of endo and exonucleases (Martinez, J., et al., Cell, 110:563-74 (2002)). However, the effect of RNAi or siRNA or their use is not limited to any type of mechanism.

Small Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, S. M., et al., Nature, 411:494 498(2001); Ui-Tei, K., et al., FEBS Lett, 479:79-82 (2000)). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit.

Similar to RNAi, CRISPR (Clustered Regularly Interspaced Short Palindromic Repeats) interference is a powerful approach, via selective DNA cleavage, for reducing gene expression of endogenously expressed proteins. CRISPRs are genetic elements containing direct repeats separated by unique spacers, many of which are identical to sequences found in phage and other foreign genetic elements. Recent work has demonstrated the role of CRISPRs in adaptive immunity and shown that small RNAs derived from CRISPRs (crRNAs) are implemented as homing oligonucleotides for the targeted interference of foreign DNA (Jinek et al., Science, 337:816-821 (2012)). crRNAs are used to selectively cleave DNA at the genetic level.

Where the functional nucleic acid serves as an enzyme cofactor, the cofactor can be, for example, a substrate-guiding sequence (or guide), which directs a nuclease to cleave a substrate (an RNA or DNA).

2. Surface Molecules

Surface molecules can be used to couple, associate, encapsulate, hold, etc. components of the disclosed compositions. Surface molecules can be associated with and arranged in the compositions in a variety of configurations. In some forms, surface molecules can be associated with, conjugated to, and/or covalently coupled to a plurality of peptides (such as CAQK peptides), a plurality of cargo molecules, or both. In some forms, surface molecules can be associated with, conjugated to, and/or covalently coupled to a plurality of peptides (such as CAQK peptides), where the peptides can be associated with, conjugated to, and/or covalently coupled to a plurality of cargo molecules. In some forms, surface molecules can be associated with, conjugated to, and/or covalently coupled to a plurality of cargo molecules, where the cargo molecules can be associated with, conjugated to, and/or covalently coupled to a plurality of peptides (such as CAQK peptides). Combinations of these combinations can also be used.

The surface molecules, alternatively referred to as a surface particles, disclosed herein can be associated with CAQK peptides and cargo molecules in such a way that the composition is delivered to a target. The surface molecule can be any substance that can be used with the CAQK peptides and cargo molecules, and is not restricted by size or substance. The term surface molecule is used to identify a component of the disclosed composition but is not intended to be limiting. In particular, the disclosed surface molecules are not limited to substances, compounds, compositions, particles or other materials composed of a single molecule. Rather, the disclosed surface molecules are any substance(s), compound(s), composition(s), particle(s) and/or other material(s) that can be associated with one or more CAQK peptides such that at least some of the CAQK peptides are presented and/or accessible on the surface of the surface molecule. A variety of examples of suitable surface molecules are described and disclosed herein.

In some forms, the surface molecule can include a nanoparticle, a nanoworm, an iron oxide nanoworm, an iron oxide nanoparticle, an albumin nanoparticle, a liposome, a micelle, a phospholipid, a polymer, a microparticle, a bead, a virus, a phage, a viral particle, a phage particle, a viral capsid, a phage capsid, a virus-like particle, or a fluorocarbon microbubble.

The term "nanoparticle" refers to a nanoscale particle with a size that is measured in nanometers, for example, a nanoscopic particle that has at least one dimension of less than about 100 nm. Examples of nanoparticles include paramagnetic nanoparticles, superparamagnetic nanoparticles, metal nanoparticles, nanoworms, fullerene-like materials, inorganic nanotubes, dendrimers (such as with covalently attached metal chelates), nanofibers, nanohorns, nano-onions, nanorods, nanoropes and quantum dots. A nanoparticle can produce a detectable signal, for example, through absorption and/or emission of photons (including radio frequency and visible photons) and plasmon resonance.

Microspheres (or microbubbles) can also be used with the disclosed compositions and methods disclosed. Microspheres containing chromophores have been utilized in an extensive variety of applications, including photonic crystals, biological labeling, and flow visualization in microfluidic channels. See, for example, Y. Lin, et al., Appl. Phys Lett. 2002, 81, 3134; D. Wang, et al., Chem. Mater. 2003, 15, 2724; X. Gao, et al., J. Biomed. Opt. 2002, 7, 532; M. Han, et al., Nature Biotechnology. 2001, 19, 631; V. M. Pal, et al., Mag. & Magnetic Mater. 1999, 194, 262, each of which is incorporated by reference in its entirety. Both the photostability of the chromophores and the monodispersity of the microspheres can be important.

Nanoparticles, such as, for example, metal nanoparticles, metal oxide nanoparticles, or semiconductor nanocrystals can be incorporated into microspheres. The optical, magnetic, and electronic properties of the nanoparticles can allow them to be observed while associated with the microspheres and can allow the microspheres to be identified and spatially monitored. For example, the high photostability, good fluorescence efficiency and wide emission tunability of colloidally synthesized semiconductor nanocrystals can make them an excellent choice of chromophore. Unlike organic dyes, nanocrystals that emit different colors (i.e. different wavelengths) can be excited simultaneously with a single light source. Colloidally synthesized semiconductor nanocrystals (such as, for example, core-shell CdSe/ZnS and CdS/ZnS nanocrystals) can be incorporated into microspheres. The microspheres can be monodisperse silica microspheres.

The nanoparticle can be a metal nanoparticle, a metal oxide nanoparticle, or a semiconductor nanocrystal. The metal of the metal nanoparticle or the metal oxide nanoparticle can include titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, zinc, cadmium, scandium, yttrium, lanthanum, a lanthanide series or actinide series element (e.g., cerium, praseodymium, neodymium, promethium, samarium, europium, gadolinium, terbium, dysprosium, holmium, erbium, thulium, ytterbium, lutetium, thorium, protactinium, and uranium), boron, aluminum, gallium, indium, thallium, silicon, germanium, tin, lead, antimony, bismuth, polonium, magnesium, calcium, strontium, and barium. In some forms, the metal can be iron, ruthenium, cobalt, rhodium, nickel, palladium, platinum, silver, gold, cerium or samarium. The metal oxide can be an oxide of any of these materials or combination of materials. For example, the metal can be gold, or the metal oxide can be an iron oxide, a cobalt oxide, a zinc oxide, a cerium oxide, or a titanium oxide. Preparation of metal and metal oxide nanoparticles is described, for example, in U.S. Pat. Nos. 5,897,945 and 6,759,199, each of which is incorporated by reference in its entirety.

The nanoparticles can be comprised of cargo molecules and a carrier protein (such as albumin). Such nanoparticles are useful, for example, to deliver hydrophobic or poorly soluble compounds. Nanoparticles of poorly water soluble drugs (such as taxane) have been disclosed in, for example, U.S. Pat. Nos. 5,916,596; 6,506,405; and 6,537,579 and also in U.S. Pat. Pub. No. 2005/0004002A1.

In some forms, the nanoparticles can have an average or mean diameter of no greater than about 1000 nanometers (nm), such as no greater than about any of 900, 800, 700, 600, 500, 400, 300, 200, and 100 nm. In some forms, the average or mean diameters of the nanoparticles can be no greater than about 200 nm. In some forms, the average or mean diameters of the nanoparticles can be no greater than about 150 nm. In some forms, the average or mean diameters of the nanoparticles can be no greater than about 100 nm. In some forms, the average or mean diameter of the nanoparticles can be about 20 to about 400 nm. In some forms, the average or mean diameter of the nanoparticles can be about 40 to about 200 nm. In some forms, the nanoparticles are sterile-filterable.

The nanoparticles can be present in a dry formulation (such as lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

Examples of suitable carrier proteins include proteins normally found in blood or plasma, which include, but are not limited to, albumin, immunoglobulin including IgA, lipoproteins, apolipoprotein B, alpha-acid glycoprotein, beta-2-macroglobulin, thyroglobulin, transferin, fibronectin, factor VII, factor VIII, factor IX, factor X, and the like. In some forms, the carrier protein is non-blood protein, such as casein, .alpha.-lactalbumin, and beta-lactoglobulin. The carrier proteins may either be natural in origin or synthetically prepared. In some forms, the pharmaceutically acceptable carrier includes albumin, such as human serum albumin. Human serum albumin (HSA) is a highly soluble globular protein of $M_r$ 65K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Intravenous use of HSA solution has been indicated for the prevention and treatment of hypovolumic shock (see, e.g., Tullis, JAMA 237:355-360, 460-463 (1977)) and Houser et al., Surgery, Gynecology and Obstetrics, 150:811-816 (1980)) and in conjunction with exchange transfusion in the treatment of neonatal hyperbilirubinemia (see, e.g., Finlayson, Seminars in Thrombosis and Hemostasis, 6:85-120 (1980)). Other albumins are contemplated, such as bovine serum albumin. Use of such non-human albumins could be appropriate, for example, in the context of use of these compositions in non-human mammals, such as the veterinary (including domestic pets and agricultural context).

Carrier proteins (such as albumin) in the composition generally serve as a carrier for the hydrophobic cargo molecules, i.e., the carrier protein in the composition makes the cargo molecules more readily suspendable in an aqueous medium or helps maintain the suspension as compared to compositions not comprising a carrier protein. This can avoid the use of toxic solvents (or surfactants) for solubilizing the cargo molecules, and thereby can reduce one or more side effects of administration of the cargo molecules into an individual (such as a human). Thus, in some forms, the composition described herein can be substantially free (such as free) of surfactants, such as Cremophor (including Cremophor EL® (BASF)). In some forms, the composition can be substantially free (such as free) of surfactants. A composition is "substantially free of Cremophor" or "substantially free of surfactant" if the amount of Cremophor or surfactant in the composition is not sufficient to cause one or more side effect(s) in an individual when the composition is administered to the individual.

The amount of carrier protein in the composition described herein will vary depending on other components in the composition. In some forms, the composition can include a carrier protein in an amount that is sufficient to stabilize the cargo molecules in an aqueous suspension, for example, in the form of a stable colloidal suspension (such as a stable suspension of nanoparticles). In some forms, the carrier protein is in an amount that reduces the sedimentation rate of the cargo molecules in an aqueous medium. For particle-containing compositions, the amount of the carrier protein also depends on the size and density of nanoparticles of the cargo molecules.

Methods of making nanoparticle compositions are known in the art. For example, nanoparticles containing cargo molecules and carrier protein (such as albumin) can be prepared under conditions of high shear forces (e.g., sonication, high pressure homogenization, or the like). These methods are disclosed in, for example, U.S. Pat. Nos. 5,916,596; 6,506,405; and 6,537,579 and also in U.S. Pat. Pub. No. 2005/0004002A1.

Briefly, the hydrophobic carrier molecules can be dissolved in an organic solvent, and the solution can be added to a human serum albumin solution. The mixture is subjected to high pressure homogenization. The organic solvent can then be removed by evaporation. The dispersion obtained can be further lyophilized. Suitable organic solvent include, for example, ketones, esters, ethers, chlorinated solvents, and other solvents known in the art. For example, the organic solvent can be methylene chloride and chloroform/ethanol (for example with a ratio of 1:9, 1:8, 1:7, 1:6, 1:5, 1:4, 1:3, 1:2, 1:1, 2:1, 3:1, 4:1, 5:1, 6:1, 7:1, 8:1, or 9:1).

The nanoparticle can also be, for example, a heat generating nanoshell. As used herein, "nanoshell" is a nanoparticle having a discrete dielectric or semi-conducting core section surrounded by one or more conducting shell layers. U.S. Pat. No. 6,530,944 is hereby incorporated by reference herein in its entirety for its teaching of the methods of making and using metal nanoshells. CAQK peptides can be attached to the disclosed compositions and/or carriers.

"Liposome" as the term is used herein refers to a structure comprising an outer lipid bi- or multi-layer membrane surrounding an internal aqueous space. Liposomes can be used to package any cargo molecule for targeting to nervous system injury. Materials and procedures for forming liposomes are well-known to those skilled in the art. Upon dispersion in an appropriate medium, a wide variety of phospholipids swell, hydrate and form multilamellar concentric bilayer vesicles with layers of aqueous media separating the lipid bilayers. These systems are referred to as multilamellar liposomes or multilamellar lipid vesicles ("MLVs") and have diameters within the range of 10 nm to 100 µm. These MLVs were first described by Bangham, et al., J Mol. Biol. 13:238-252 (1965). In general, lipids or lipophilic substances are dissolved in an organic solvent. When the solvent is removed, such as under vacuum by rotary evaporation, the lipid residue forms a film on the wall of the container. An aqueous solution that typically contains electrolytes or hydrophilic biologically active materials is then added to the film. Large MLVs are produced upon agitation. When smaller MLVs are desired, the larger vesicles are subjected to sonication, sequential filtration through filters with decreasing pore size or reduced by other forms of mechanical shearing. There are also techniques by which MLVs can be reduced both in size and in number of lamellae, for example, by pressurized extrusion (Barenholz, et al., FEBS Lett. 99:210-214 (1979)).

Liposomes can also take the form of unilamnellar vesicles, which are prepared by more extensive sonication of MLVs, and consist of a single spherical lipid bilayer surrounding an aqueous solution. Unilamellar vesicles ("ULVs") can be small, having diameters within the range of 20 to 200 nm, while larger ULVs can have diameters within the range of 200 nm to 2 µm. There are several well-known techniques for making unilamellar vesicles. In Papahadjopoulos, et al., Biochim et Biophys Acta 135:624-238 (1968), sonication of an aqueous dispersion of phospholipids produces small ULVs having a lipid bilayer surrounding an aqueous solution. Schneider, U.S. Pat. No. 4,089,801 describes the formation of liposome precursors by ultrasonication, followed by the addition of an aqueous medium containing amphiphilic compounds and centrifugation to form a biomolecular lipid layer system.

Small ULVs can also be prepared by the ethanol injection technique described by Batzri et al., Biochim et Biophys Acta 298:1015-1019 (1973) and the ether injection technique of Deamer et al., Biochim et Biophys Acta 443:629-634 (1976). These methods involve the rapid injection of an organic solution of lipids into a buffer solution, which results in the rapid formation of unilamellar liposomes. Another technique for making ULVs is taught by Weder et al. in "Liposome Technology", ed. G. Gregoriadis, CRC Press Inc., Boca Raton, Fla., Vol. I, Chapter 7, pg. 79-107 (1984). This detergent removal method involves solubilizing the lipids and additives with detergents by agitation or sonication to produce the desired vesicles.

Papahadjopoulos et al., U.S. Pat. No. 4,235,871, describes the preparation of large ULVs by a reverse phase evaporation technique that involves the formation of a water-in-oil emulsion of lipids in an organic solvent and the drug to be encapsulated in an aqueous buffer solution. The organic solvent is removed under pressure to yield a mixture which, upon agitation or dispersion in an aqueous media, is converted to large ULVs. Suzuki et al., U.S. Pat. No. 4,016,100, describes another method of encapsulating agents in unilamellar vesicles by freezing/thawing an aqueous phospholipid dispersion of the agent and lipids.

In addition to the MLVs and ULVs, liposomes can also be multivesicular. Described in Kim et al., Biochim et Biophys Acta 728:339-348 (1983), these multivesicular liposomes are spherical and contain internal granular structures. The outer membrane is a lipid bilayer and the internal region contains small compartments separated by bilayer septum. Still yet another type of liposomes are oligolamellar vesicles ("OLVs"), which have a large center compartment surrounded by several peripheral lipid layers. These vesicles, having a diameter of 2-15 µm, are described in Callo, et al., Cryobiology 22(3):251-267 (1985).

Mezei et al., U.S. Pat. Nos. 4,485,054 and 4,761,288 also describe methods of preparing lipid vesicles. More recently, Hsu, U.S. Pat. No. 5,653,996 describes a method of preparing liposomes utilizing aerosolization and Yiournas, et al., U.S. Pat. No. 5,013,497 describes a method for preparing liposomes utilizing a high velocity-shear mixing chamber. Methods are also described that use specific starting materials to produce ULVs (Wallach, et al., U.S. Pat. No. 4,853,228) or OLVs (Wallach, U.S. Pat. Nos. 5,474,848 and 5,628,936).

A comprehensive review of all the aforementioned lipid vesicles and methods for their preparation are described in "Liposome Technology", ed. G. Gregoriadis, CRC Press Inc., Boca Raton, Fla., Vol. I, II & III, $3^{rd}$ Ed. (2006). This and the aforementioned references describing various lipid vesicles suitable for use in the disclosed compositions are incorporated herein by reference.

"Micelle" as used herein refers to a structure comprising an outer lipid monolayer. Micelles can be formed in an aqueous medium when the Critical Micelle Concentration (CMC) is exceeded. Small micelles in dilute solution at approximately the critical micelle concentration (CMC) are generally believed to be spherical. However, under other conditions, they may be in the shape of distorted spheres, disks, rods, lamellae, and the like. Micelles formed from relatively low molecular weight amphiphile molecules can have a high CMC so that the formed micelles dissociate rather rapidly upon dilution. If this is undesired, amphiphile molecules with large hydrophobic regions can be used. For example, lipids with a long fatty acid chain or two fatty acid chains, such as phospholipids and sphingolipids, or polymers, specifically block copolymers, can be used.

Polymeric micelles have been prepared that exhibit CMCs as low as $10^{-6}$ M (molar). Thus, they tend to be very stable while at the same time showing the same beneficial characteristics as amphiphile micelles. Any micelle-forming polymer can be used in the disclosed compositions and methods. Examples of micelle-forming polymers include, without limitation, methoxy poly(ethylene glycol)-b-poly(ε-caprolactone), conjugates of poly(ethylene glycol) with phosphatidyl-ethanolamine, poly(ethylene glycol)-b-polyesters, poly(ethylene glycol)-b-poly(L-aminoacids), poly(N-vinylpyrrolidone)-b1-poly(orthoesters), poly(N-vinylpyrrolidone)-b-polyanhydrides and poly(N-vinylpyrrolidone)-b-poly(alkyl acrylates).

Micelles can be produced by processes conventional in the art. Examples of such are described in, for example, Liggins (Liggins and Burt, Adv. Drug Del. Rev. 54: 191-202, (2002)); Zhang et al. (Zhang, X. et al., Int. J. Pharm. 132: 195-206, (1996)); and Churchill (Churchill and Hutchinson, U.S. Pat. No. 4,745,160 (1988)). In one such method, polyether-polyester block copolymers, which are amphipathic polymers having hydrophilic (polyether) and hydrophobic (polyester) segments, are used as micelle forming carriers.

Another type of micelle can be formed using, for example, AB-type block copolymers having both hydrophilic and hydrophobic segments, as described in, for example, Tuzar (Tuzar and Kratochvil, Adv. Colloid Interface Sci. 6:201-232, (1976)); and Wilhelm et al. (Wilhelm et al., Macromolecules 24: 1033-1040 (1991)). These polymeric micelles are able to maintain satisfactory aqueous stability. These micelles, in the range of approximately <200 nm in size, are effective in reducing non-selective RES scavenging and show enhanced permeability and retention.

U.S. Pat. No. 5,929,177 to Kataoka et al. describes a polymeric molecule usable as, for example, a drug delivery carrier. The micelle is formed from a block copolymer having functional groups on both of its ends and which includes hydrophilic/hydrophobic segments. The polymer functional groups on the ends of the block copolymer include amino, carboxyl and mercapto groups on the .alpha.-terminal and hydroxyl, carboxyl group, aldehyde group and vinyl group on the .omega.-terminal. The hydrophilic segment includes polyethylene oxide, while the hydrophobic segment is derived from lactide, lactone or (meth)acrylic acid ester.

Poly(D,L-lactide)-b-methoxypolyethylene glycol (MePEG:PDLLA) diblock copolymers can be made using MePEG 1900 and 5000. The reaction can be allowed to proceed for 3 hr at 160° C., using stannous octoate (0.25%) as a catalyst. However, a temperature as low as 130° C. can be used if the reaction is allowed to proceed for about 6 hours, or a temperature as high as 190° C. can be used if the reaction is carried out for only about 2 hours.

N-isopropylacrylamide ("IPAAm") (Kohjin, Tokyo, Japan) and dimethylacrylamide ("DMAAm") (Wako Pure Chemicals, Tokyo, Japan) can be used to make hydroxyl-terminated poly(IPAAm-co-DMAAm) in a radical polymerization process, using the method of Kohori et al. (1998). (Kohori et al., J. Control. Rel. 55: 87-98, (1998)). The obtained copolymer can be dissolved in cold water and filtered through two ultrafiltration membranes with a 10,000 and 20,000 molecular weight cut-off. The polymer solution is first filtered through a 20,000 molecular weight cut-off membrane. Then the filtrate was filtered again through a 10,000 molecular weight cut-off membrane. Three molecular weight fractions can be obtained as a result, a low molecular weight, a middle molecular weight, and a high molecular weight fraction. A block copolymer can then be synthesized by a ring opening polymerization of D,L-lactide from the terminal hydroxyl group of the poly(IPAAm-co-DMAAm) of the middle molecular weight fraction. The resulting poly(IPAAm-co-DMAAm)-b-poly(D,L-lactide) copolymer can be purified as described in Kohori et al. (1999). (Kohori et al., Colloids Surfaces B: Biointerfaces 16: 195-205, (1999)).

Examples of block copolymers from which micelles can be prepared are found in U.S. Pat. No. 5,925,720, to Kataoka et al., U.S. Pat. No. 5,412,072 to Sakurai et al., U.S. Pat. No. 5,410,016 to Kataoka et al., U.S. Pat. No. 5,929,177 to Kataoka et al., U.S. Pat. No. 5,693,751 to Sakurai et al., U.S. Pat. No. 5,449,513 to Yokoyama et al., WO 96/32434, WO 96/33233 and WO 97/0623, the contents of all of which are incorporated by reference. Modifications thereof, which are prepared by introducing thereon a suitable functional group (including an ethyleneically unsaturated polymerizable group), are also examples of block copolymers from which micelles can be prepared. If the block copolymer has a sugar residue on one end of the hydrophilic polymer segment, as in the block copolymer of WO 96/32434, the sugar residue should preferably be subjected to Malaprade oxidation so that a corresponding aldehyde group may be formed.

Lipids are synthetically or naturally-occurring molecules, which includes fats, waxes, sterols, prenol lipids, fat-soluble vitamins (such as vitamins A, D, E and K), glycerolipids, monoglycerides, diglycerides, triglycerides, glycerophospholipids, sphingolipids, phospholipids, fatty acids monoglycerides, saccharolipids and others. Lipids can be hydrophobic or amphiphilic small molecules; the amphiphilic nature of some lipids allows them to form structures such as monolayers, vesicles, micelles, liposomes, bi-layers or membranes in an appropriate environment i.e. aqueous environment. Any of a number of lipids can be used as amphiphile molecules, including amphipathic, neutral, cationic, and anionic lipids. Such lipids can be used alone or in combination, and can also include bilayer stabilizing components such as polyamide oligomers (see, e.g., U.S. Pat. No. 6,320,017, "Polyimide Oligomers", by Ansell), peptides, proteins, detergents, lipid-derivatives, such as PEG coupled to phosphatidylethanolamine and PEG conjugated to ceramides (see U.S. Pat. No. 5,885,613). In some forms, cloaking agents, which reduce elimination of liposomes by the host immune system, can also be included, such as polyamide-oligomer conjugates, e.g., ATTA-lipids, (see U.S. Pat. No. 5,693,463), and PEG-lipid conjugates (see U.S. Pat. Nos. 5,820,873, 5,534,499 and 5,885,613).

Any of a number of neutral lipids can be included, referring to any of a number of lipid species which exist either in an uncharged or neutral zwitterionic form at physiological pH, including diacylphosphatidylcholine, diacylphosphatidylethanolamine, ceramide, sphingomyelin, cephalin, cholesterol, cerebrosides, and diacylglycerols.

Cationic lipids, which carry a net positive charge at physiological pH, can readily be used as amphiphile molecules. Such lipids include, but are not limited to, N,N-dioleyl-N,N-dimethylammonium chloride ("DODAC"); N-(2,3-dioleyloxy) propyl-N,N—N-triethylammonium chloride ("DOTMA"); N,N-distearyl-N,N-dimethylammonium bromide ("DDAB"); N-(2,3-dioleoyloxy)propyl)-N,N, N-trimethylammonium chloride ("DOTAP"); 3.beta.-(N—(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethyl-ammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), and N-(1,2-dimyristyloxyprop-3-yl)-N,N-dimethyl-N-hydroxyethyl ammonium bromide ("DMRIE"). Additionally, a number of commercial preparations of cationic lipids can be used, such as LIPOFECTIN (including DOTMA and DOPE, available from GIBCO/BRL), LIPOFECTAMINE (comprising DOSPA and DOPE, available from GIBCO/BRL), and TRANSFECTAM (comprising DOGS, in ethanol, from Promega Corp.).

Anionic lipids can be used as amphiphile molecules and include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

Amphipathic lipids can also be suitable amphiphile molecules. "Amphipathic lipids" refer to any suitable material, where the hydrophobic portion of the lipid material orients into a hydrophobic phase, while the hydrophilic portion orients toward the aqueous phase. Such compounds include, but are not limited to, fatty acids, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lysophosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and β-acyloxyacids, can also be used. Additionally, such amphipathic lipids can be readily mixed with other lipids, such as triglycerides and sterols. Zwitterionic lipids are a form of amphiphatic lipid.

Sphingolipids are fatty acids conjugated to the aliphatic amino alcohol sphingosine. The fatty acid can be covalently bond to sphingosine via an amide bond. Any amino acid as described above can be covalently bond to sphingosine to form a sphingolipid. A sphingolipid can be further modified by covalent bonding through the α-hydroxyl group. The modification can include alkyl groups, alkenyl groups, alkynyl groups, aromatic groups, heteroaromatic groups, cyclyl groups, heterocyclyl groups, phosphonic acid groups. Non-limiting examples of shingolipids are N-acylsphingosine, N-Acylsphingomyelin, Forssman antigen.

Saccharolipids are compounds that contain both fatty acids and sugars. The fatty acids are covalently bonded to a sugar backbone. The sugar backbone can contain one or more sugars. The fatty acids can bond to the sugars via either amide or ester bonds. The sugar can be any sugar base. The fatty acid can be any fatty acid as described elsewhere herein. The provided compositions can include either natural or synthetic saccharolipids. Non-limiting saccharolipids are UDP-3-O-((β-hydroxymyristoyl)-GlcNAc, lipid IV A, Kdo2-lipid A.

D. Homing Molecules

Disclosed are homing molecules that selectively home to CSPG-rich extracellular matrix complexes (extracellular matrix containing hyaluronic acid, versican, tenascin-R, and Hapln and exemplified by the matrix of cultured U251 astrocytoma cells). CAQK peptides are a type of such homing molecules, but other peptides, molecules, compounds can also home to CSPG-rich extracellular matrix complexes at sites of nervous system injury. Such homing molecules can be identified by any suitable method. For example, in some forms, the homing molecules can be identified by bringing into contact the homing molecule and versican, tenascin-R, Hapln, or combinations thereof, and assessing whether the homing molecule specifically binds to the versican, tenascin-R, Hapln, or combination thereof. The homing molecule is identified if the homing molecule specifically binds to the versican, tenascin-R, Hapln, or combination thereof. In some forms, the homing molecules can be identified by bringing into contact the homing molecule and CSPG-rich extracellular matrix complexes, and assessing whether the homing molecule specifically binds to the CSPG-rich extracellular matrix complexes. The homing molecule is identified if the homing molecule specifically binds to the CSPG-rich extracellular matrix complexes. In some forms the CSPG-rich extracellular matrix complexes can be matrix produced by U251 astrocytoma cells.

Methods

A. Methods of Making

The disclosed peptides, cargo molecules, surface molecules, cargo compositions, and other components of the disclosed compositions can be synthesized and produced generally using known methods, some of which are described elsewhere herein. For example, methods for peptide synthesis are well known and can be used to make the disclosed peptides. Cargo molecules, which are often therapeutic or detectable agents, can be made as is known and/or as is appropriate for the molecule involved.

Association of the components of the disclosed compositions can be aided or accomplished via molecules, conjugates and/or compositions. Where such molecules, conjugates and/or compositions are other than CAQK peptides, cargo compositions, cargo molecules, or surface molecules, they can be referred to herein as linkers. Such linkers can be any molecule, conjugate, composition, etc. that can be used to associate components of the disclosed compositions. Generally, linkers can be used to associate components other than surface molecules to surface molecules and to associate different components with each other. Useful linkers include materials that are biocompatible, have low bioactivity, have low antigenicity, etc. That is, such useful linker materials can serve the linking/association function without adding unwanted bioreactivity to the disclosed compositions. Many such materials are known and used for similar linking and association functions. Polymer materials are a particularly useful form of linker material. For example, polyethylene glycols can be used.

Disclosed are linkers for associating components of the disclosed compositions. Such linkers can be any molecule, conjugate, composition, etc. that can be used to associate components of the disclosed compositions. Generally, linkers can be used to associate components other than surface molecules to surface molecules and to associate different components with each other. Useful linkers include materials that are biocompatible, have low bioactivity, have low antigenicity, etc. That is, such useful linker materials can serve the linking/association function without adding unwanted bioreactivity to the disclosed compositions. Many such materials are known and used for similar linking and association functions. Polymer materials are a particularly useful form of linker material. For example, polyethylene glycols can be used.

Linkers of different lengths can be used to couple the disclosed components to surface molecules and to each other. A flexible linker can function well even if relatively short, while a stiffer linker can be longer to allow effective exposure and density. The length of a linker can refer to the number of atoms in a continuous covalent chain between the attachment points on the components being linked or to the length (in nanometers, for example) of a continuous covalent chain between the attachment points on the components being linked. Unless the context clearly indicates otherwise, the length refers to the shortest continuous covalent chain between the attachment points on the components being linked not accounting for side chains, branches, or loops. Due to flexibility of the linker, all of the linkers may not have same distance from the surface molecule or between components. Thus linkers with different chain lengths can make the resulting composition more effective (by increasing density, for example). Branched linkers bearing multiple components also allow attachment of more than one component at a given site of the surface molecule or on another component. Useful lengths for linkers include at least, up to, about, exactly, or between 10, 15, 20, 25, 30, 35, 40, 45, 50, 60, 70, 80, 90, 100, 120, 140, 150, 160, 180, 200, 250, 300, 350, 400, 450, 500, 550, 600, 650, 700, 750, 800, 850, 900, 950, 1,000, 2,000, 3,000, 4,000, 5,000, 6,000, 7,000, 8,000, 9,000, and 10,000 atoms. Useful lengths for linkers include at least, up to, about, exactly, or between 10, 15, 20, 25, 30, 35, 40, 45, 50, 60, 70, 80, 90, 100, 120, 140, 150, 160, 180, 200, 250, 300, 350, 400, 450, 500, 550, 600, 650, 700, 750, 800, 850, 900, 950, 1,000, 2,000, 3,000, 4,000, 5,000, 6,000, 7,000, 8,000, 9,000, and 10,000 nanometers. Any range of these lengths and all lengths between the listed lengths are specifically contemplated.

Hydrophilic or water-solubility linkers can increase the mobility of the attached components. Examples of water-soluble, biocompatible polymers which can serve as linkers include, but are not limited to polymers such polyethylene glycol (PEG), polyethylene oxide (PEO), polyvinyl alcohol, polyhydroxyethyl methacrylate, polyacrylamide, and natural polymers such as hyaluronic acid, chondroitin sulfate, carboxymethylcellulose, and starch. Useful forms of branched tethers include star PEO and comb PEO. Star PEO can be formed of many PEO "arms" emanating from a common core.

Polyethylene glycols (PEGs) are simple, neutral polyethers which have been given much attention in biotechnical and biomedical applications (Milton Harris, J. (ed) "Poly(ethylene glycol) chemistry, biotechnical and biomedical applications" Plenum Press, New York, 1992). PEGs are soluble in most solvents, including water, and are highly hydrated in aqueous environments, with two or three water molecules bound to each ethylene glycol segment; this hydration phenomenon has the effect of preventing adsorption either of other polymers or of proteins onto PEG-modified surfaces. Furthermore, PEGs may readily be modified and bound to other molecules with only little effect on their chemistry. Their advantageous solubility and biological properties are apparent from the many possible uses of PEGs and copolymers thereof, including block copolymers such as PEG-polyurethanes and PEG-polypropylenes. Appropriate molecular weights for PEG linkers used in the disclosed compositions can be from about 120 daltons to about 20 kilodaltons. For example, PEGs can be at least, up to, about, exactly, or between 100, 150, 200, 250, 300, 350, 400, 450, 500, 600, 700, 800, 900, 1000, 1200, 1400, 1500, 1600, 1800, 2000, 2500, 3000, 3500, 4000, 4500, 5000, 5500, 6000, 6500, 7000, 7500, 8000, 8500, 9000, 9500, 10,000, 20,000, 30,000, 40,000, and 50,000 daltons. Any range of these masses and all masses between the listed masses are specifically contemplated. PEGs are usually available as mixtures of somewhat heterogeneous masses with a stated average mass (PEG-5000, for example).

The disclosed compositions can be produced using any suitable techniques. Many techniques, reactive groups, chemistries, etc. for linking components of the types disclosed herein are known and can be used with the disclosed components and compositions.

Protein crosslinkers that can be used to crosslink the disclosed compositions, surface molecules, CAQK peptides, cargo molecules, cargo compositions, and other molecules are known in the art and are defined based on utility and structure. Examples include DSS (Disuccinimidylsuberate), DSP (Dithiobis(succinimidylpropionate)), DTSSP (3,3'-Dithiobis (sulfosuccinimidylpropionate)), SULFO BS OCOES (Bis[2-(sulfosuccinimdooxycarbonyloxy) ethyl]sulfone), BS OCOES (Bis[2-(succinimdooxycarbonyloxy)ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis (sulfosuccinimidylsuccinate)), DPDPB (1,2-Di[3'-(2'-pyridyldithio) propionamido]butane), BSSS (Bis (sulfosuccinimdyl) suberate), SMPB (Succinimdyl-4-(p-maleimidophenyl) butyrate), SULFO SMPB (Sulfosuccinimdyl-4-(p-maleimidophenyl) butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl) aminobenzoate), SULFO SIAB (N-Sulfosuccinimidyl(4-iodoacetyl)aminobenzoate), SMCC (Succinimidyl-4-(N-maleimidomethyl) cyclohexane-1-carboxylate), SULFO SMCC (Sulfosuccinimidyl-4-(N-maleimidomethyl) cyclohexane-1-carboxylate), NHS LC SPDP (Succinimidyl-643-(2-pyridyldithio) propionamido) hexanoate), SULFO NHS LC SPDP (Sulfosuccinimidyl-6-[3-(2-pyridyldithio) propionamido) hexanoate), SPDP (N-Succinimdyl-3-(2-pyridyldithio) propionate), NHS BROMOACETATE (N-Hydroxysuccinimidylbromoacetate), NHS IODOACETATE (N-Hydroxysuccinimidyliodoacetate), MPBH (4-(N-Maleimidophenyl) butyric acid hydrazide hydrochloride), MCCH (4-(N-Maleimidomethyl) cyclohexane-1-carboxylic acid hydrazide hydrochloride), MBH (m-Maleimidobenzoic acid hydrazidehydrochloride), SULFO EMCS (N-(epsilon-Maleimidocaproyloxy) sulfosuccinimide), EMCS (N-(epsilon-Maleimidocaproyloxy) succinimide), PMPI (N-(p-Maleimidophenyl) isocyanate), KMUH (N-(kappa-Maleimidoundecanoic acid) hydrazide), LC SMCC (Succinimidyl-4-(N-maleimidomethyl)-cyclohexane-1-carboxy(6-amidocaproate)), SULFO GMBS (N-(gamma-Maleimidobutryloxy) sulfosuccinimide ester), SMPH (Succinimidyl-6-(beta-maleimidopropionamidohexanoate)), SULFO KMUS (N-(kappa-Maleimidoundecanoyloxy) sulfosuccinimide ester), GMBS (N-(gamma-Maleimidobutyrloxy) succinimide), DMP (Dimethylpimelimidate hydrochloride), DMS (Dimethylsuberimidate hydrochloride), MHBH (Wood's Reagent; Methyl-p-hydroxybenzimidate hydrochloride, 98%), DMA (Dimethyladipimidate hydrochloride).

Components of the disclosed compositions, such as CAQK peptides, cargo compositions, cargo molecules, surface molecules, etc., can also be coupled using, for example, maleimide coupling. By way of illustration, components can be coupled to lipids by coupling to, for example, 1,2-distearoyl-sn-glycero-3-phosphoethanolamine-N-[maleimide(polyethylene glycol)$_{2000}$; DSPE-PEG$_{2000}$-maleimide] (Avanti Polar Lipids) by making use of a free cysteine sulfhydryl group on the component. The reaction can be performed, for example, in aqueous solution at room temperature for 4 hours. This coupling chemistry can be used to couple components of co-compositions and cargo compositions.

Components of the disclosed compositions, such as CAQK peptides, cargo compositions, cargo molecules, surface molecules, etc., can also be coupled using, for example, amino group-functionalized dextran chemistry. Particles, such as, for example, nanoparticles, nanoworms, and micelles, can be coated with amino group functionalized dextran. Attachment of PEG to aminated particles increases the circulation time, presumably by reducing the binding of plasma proteins involved in opsonization (Moghimi et al., Pharm. Rev. 53, 283-318 (2001)). The particles can have surface modifications, for example, for reticuloendothelial system avoidance (PEG) and homing (CAQK peptides), endosome escape (pH-sensitive peptide; for example, Pirollo et al., Cancer Res. 67, 2938-43 (2007)), a detectable agent (cargo molecule), a therapeutic compound (cargo molecule), or a combination. To accommodate all these functions on one particle, optimization studies can be conducted to determine what proportion of the available linking sites at the surface of the particles any one of these elements should occupy to give the best combination of targeting and payload delivery.

The disclosed peptides can have additional N-terminal, C-terminal, or intermediate amino acid sequences, e.g., amino acid linkers or tags. The term "amino acid linker" refers to an amino acid sequences or insertions that can be used to connect or separate two distinct peptides, polypeptides, or polypeptide fragments, where the linker does not otherwise contribute to the essential function of the composition. The term "amino acid tag" refers to a distinct amino acid sequence that can be used to detect or purify the disclosed peptide, where the tag does not otherwise contribute to the essential function of the composition. The disclosed peptides can further have deleted N-terminal, C-terminal or intermediate amino acids that do not contribute to the essential activity of the peptides.

Components can be directly or indirectly covalently bound to surface molecules or each other by any functional group (e.g., amine, carbonyl, carboxyl, aldehyde, alcohol). For example, one or more amine, alcohol or thiol groups on the components can be reacted directly with isothiocyanate, acyl azide, N-hydroxysuccinimide ester, aldehyde, epoxide, anhydride, lactone, or other functional groups incorporated onto the surface molecules or other components. Schiff bases formed between the amine groups on the components and aldehyde groups on the surface molecule or other components can be reduced with agents such as sodium cyanoborohydride to form hydrolytically stable amine links (Ferreira et al., J. Molecular Catalysis B: Enzymatic 2003, 21, 189-199). Components can be coupled to surface molecules and other components by, for example, the use of a heterobifunctional silane linker reagent, or by other reactions that activate functional groups on either the surface molecule or the components.

Useful modes for linking components to surface molecules and to other components include heterobifunctional linkers or spacers. Such linkers can have both terminal amine and thiol reactive functional groups for reacting amines on components with sulfhydryl groups, thereby coupling the components in an oriented way. These linkers can contain a variable number of atoms. Examples of such linkers include, but are not limited to, N-Succinimidyl 3-(2-pyridyldithio)propionate (SPDP, 3- and 7-atom spacer), long-chain-SPDP (12-atom spacer), (Succinimidyloxycarbonyl-a-methyl-2-(2-pyridyldithio) toluene) (SMPT, 8-atom spacer), Succinimidyl-4-(N-maleimidomethyl)cyclohexane-1-carboxylate) (SMCC, 11-atom spacer) and Sulfosuccinimidyl-4-(N-maleimidomethyl)cyclohexane-1-carboxylate, (sulfo-SMCC, 11-atom spacer), m-Maleimidobenzoyl-N hydroxysuccinimide ester (MBS, 9-atom spacer), N-(g-maleimidobutyryloxy)succinimide ester (GMBS, 8-atom spacer), N-(g-maleimidobutyryloxy) sulfosuccinimide ester (sulfo-GMBS, 8-atom spacer), Succinimidyl 6-((iodoacetyl) amino) hexanoate (SIAX, 9-atom spacer), Succinimidyl 6-(6-(((4-iodoacetyl)amino)hexanoyl)amino)hexanoate (SI-AXX, 16-atom spacer), and p-nitrophenyl iodoacetate (NPIA, 2-atom spacer). It is understood that a number of other coupling agents or links, with different number of atoms, can be used.

Hydrophilic spacer atoms can be incorporated into linkers to increase the distance between the reactive functional groups. For example, polyethylene glycol (PEG) can be incorporated into sulfo-GMBS. Hydrophilic molecules such as PEG have also been shown to decrease non-specific binding (NSB) and increase hydrophilicity of surfaces when covalently coupled. PEG can also be used as the primary linker material.

Free amine groups of components can also be attached to surface molecules or other components containing reactive amine groups via homobifunctional linkers. Linkers such as dithiobis(succinimidylpropionate) (DSP, 8-atom spacer), disuccinimidyl suberate (DSS, 8-atom spacer), glutaraldehyde (4-atom spacer), Bis[2-(succinimidyloxycarbonyloxy) ethyl]sulfone (BSOCOES, 9-atom spacer), all requiring high pH, can be used for this purpose. Examples of homobifunctional sulfhydryl-reactive linkers include, but are not limited to, 1,4-Di-[3'-2'-pyridyldithio)propion-amido]butane (DP-DPB, 16-atom spacer) and Bismaleimidohexane (BMH, 14-atom spacer). For example, these homobifunctional linkers are first reacted with a thiolated surface in aqueous solution (for example PBS, pH 7.4), and then in a second step, the thiolated antibody or protein is joined by the link. Homo- and heteromultifunctional linkers can also be used.

Direct binding of components to thiol, amine, or carboxylic acid functional groups on surface molecules and other components be used to produce compositions which exhibit viral binding (due to increased density of components, for example), resulting in enhanced sensitivity.

As an example, when necessary to achieve high peptide coupling density, additional amino groups can be added to the surface molecules (such as commercially obtained SPIO) as follows: First, to crosslink the particles before the amination step, 3 ml of the colloid (~10 mgFe/ml in double-distilled water) was added to 5 ml of 5M NaOH and 2 ml of epichlorohydrin (Sigma, St. Louis, Mo.). The mixture was agitated for 24 hours at room temperature to promote interaction between the organic phase (epichlorohydrin) and aqueous phase (dextran-coated particle colloid). In order to remove excess epichlorohydrin, the reacted mixture was dialyzed against double-distilled water for 24 hours using a dialysis cassette (10,000 Da cutoff, Pierce, Rockford Ill.). Amino groups were added to the surface of the particles as follows: 0.02 ml of concentrated ammonium hydroxide (30%) was added to lml of colloid (~10 mg Fe/ml). The mixture was agitated at room temperature for 24 hours. The reacted mixture was dialyzed against double-distilled water for 24 hours. To further rinse the particles, the colloid was trapped on a MACS® Midi magnetic separation column (Miltenyi Biotec, Auburn Calif.), rinsed with PBS three times, and eluted from the column with lml PBS.

Linkers are useful for achieving useful numbers and densities of the components (such as CAQK peptides and cargo molecules) on surface molecules. For example, linkers of fibrous form are useful for increasing the number of components per surface molecule or per a given area of the surface molecule. Similarly, linkers having a branching form are useful for increasing the number of components per surface molecule or per a given area of the surface molecule. Linkers can also have a branching fibrous form.

Sufficiency of the number and composition of CAQK peptides in the composition can be determined by assessing homing to the target and effectively delivery of the cargo molecules in a non-human animal. The composition can include a sufficient number and composition of CAQK peptides such that the composition homes to the target and effectively delivers the cargo molecules. In one example, sufficiency of the number and composition of modified and/or unmodified CAQK peptides can be determined by assessing cargo delivery and/or therapeutic effect on the target.

The composition can include a sufficient density and composition of CAQK peptides such that the composition homes to the target and effectively delivers the cargo molecules. Sufficiency of the density and composition of CAQK peptides can be determined by assessing cargo delivery and/or therapeutic effect on the target in a non-human animal.

As used herein, reference to components (such as a peptide and a cargo composition) as being "not covalently coupled" means that the components are not connected via covalent bonds (for example, that the peptide and a cargo composition are not connected via covalent bonds). That is, there is no continuous chain of covalent bonds between, for example, the peptide and a cargo composition. Conversely, reference to components (such as a peptide and a cargo composition) as being "covalently coupled" means that the components are connected via covalent bonds (for example, that the peptide and a cargo composition are connected via covalent bonds). That is, there is a continuous chain of covalent bonds between, for example, the peptide and a cargo composition. Components can be covalently coupled either directly or indirectly. Direct covalent coupling refers to the presence of a covalent bond between atoms of each of the components. Indirect covalent coupling refers to the absence of a covalent bond between atoms of each of the components. That is, some other atom or atoms not belonging to either of the coupled components intervenes between atoms of the components. Both direct and indirect covalent coupling involve a continuous chain of covalent bonds.

Non-covalent association refers to association of components via non-covalent bonds and interactions. A non-covalent association can be either direct or indirect. A direct non-covalent association refers to a non-covalent bond involving atoms that are each respectively connected via a chain of covalent bonds to the components. Thus, in a direct non-covalent association, there is no other molecule intervening between the associated components. An indirect non-covalent association refers to any chain of molecules and bonds linking the components where the components are not covalently coupled (that is, there is a least one separate molecule other than the components intervening between the components via non-covalent bonds).

Reference to components (such as a peptide and a cargo composition) as not being "non-covalently associated" means that there is no direct or indirect non-covalent association between the components. That is, for example, no atom covalently coupled to a peptide is involved in a non-covalent bond with an atom covalently coupled to a cargo composition. Within this meaning, a peptide and a cargo composition can be together in a composition where they are indirectly associated via multiple intervening non-covalent bonds while not being non-covalently associated as that term is defined herein. For example, a peptide and a cargo composition can be mixed together in a carrier where they are not directly non-covalently associated. A peptide and a cargo composition that are referred to as not indirectly non-covalently associated cannot be mixed together in a continuous composition. Reference to components (such as a peptide and a cargo composition) as not being "directly non-covalently associated" means that there is no direct non-covalent association between the components (an indirect non-covalent association may be present). Reference to components (such as a peptide and a cargo composition) as not being "indirectly non-covalently associated" means that there is no direct or indirect non-covalent association between the components.

It is understood that components can be non-covalently associated via multiple chains and paths including both direct and indirect non-covalent associations. For the purposes of these definitions, the presence a single direct non-covalent association makes the association a direct non-covalent association even if there are also indirect non-covalent associations present. Similarly, the presence of a covalent connection between components means the components are covalently coupled even if there are also non-covalent associations present. It is also understood that covalently coupled components that happened to lack any non-covalent association with each other are not considered to fall under the definition of components that are not non-covalently associated.

Additional homing molecules that target sites of nervous system injury can be identified. Such homing molecules are useful and useable in all the ways that CAQK peptides useful and useable. The method can involve bringing into contact a test compound and versican, tenascin-R, Hapln, or combinations thereof, and assessing whether the test compound specifically binds to the versican, tenascin-R, Hapln, or combination thereof. The test compound is identified as a compound that target sites of nervous system injury if the test compound specifically binds to the versican, tenascin-R, Hapln, or combination thereof. In some forms, the method can involve bringing into contact the homing molecule and CSPG-rich extracellular matrix complexes, and assessing whether the homing molecule specifically binds to the CSPG-rich extracellular matrix complexes. The homing molecule is identified if the homing molecule specifically binds to the CSPG-rich extracellular matrix complexes. In some forms the CSPG-rich extracellular matrix complexes can be matrix produced by U251 astrocytoma cells.

In some forms of the method, the versican, tenascin-R, Hapln, or combination thereof can be part of extracellular matrix. In some forms of the method, the extracellular matrix can be in or obtained from glial scar. In some forms of the method, the extracellular matrix is a CSPG-rich extracellular matrix complex (extracellular matrix containing hyaluronic acid, versican, tenascin-R, and Hapln and exemplified by the matrix of cultured U251 astrocytoma cells). In some forms of the method, the extracellular matrix is matrix from cultured U251 astrocytoma cells.

In some forms of the method, assessing whether the test compound specifically binds the versican, tenascin-R, Hapln, or combination thereof, can be accomplished by assessing whether the test compound specifically binds the CSPG-rich extracellular matrix complex. In some forms of the method, the CSPG-rich extracellular matrix complex can be at a site of nervous system injury in test animal, where bringing into contact is accomplished by administering the test compound to the animal intravenously.

In some forms of the method, the versican, tenascin-R, Hapln, or combination thereof is not comprised in extracellular matrix. In some forms of the method, the versican, tenascin-R, Hapln, or combination thereof can be made from individual versican, tenascin-R, and Hapln proteins.

In some forms of the method, the test compound can be coupled to a label, wherein assessing whether the test compound specifically binds is accomplished by detecting the label.

B. Methods of Targeting and Treating

The disclosed peptides and compositions are useful for selective targeting nervous system injury, such as brain injury and stroke injury, sites of glial scar formation, sites where hyaluronic acid, versican, tenascin-R, and Hapln are being deposited, and CSPG-rich extracellular matrix complexes. For example, the disclosed peptides and compositions are useful for selectively targeting acute nervous system injury, such as traumatic brain injury and stroke injury. Thus, methods for selectively targeting a cargo to a site of acute nervous system injury in a subject are disclosed.

In some forms, the method involves administering the disclosed composition to a subject having an acute nervous system injury. The composition selectively homes to a site of the nervous system injury in the subject thereby selectively targeting the cargo composition of the composition to the site of the nervous system injury.

In some forms, the nervous system injury includes a brain injury. In some forms, the peptide selectively homes to a site of the brain injury. In some forms, the brain injury includes traumatic brain injury, stroke injury, or both. In some forms, the peptide specifically binds to one or more of versican, tenascin-R, and Hapln. In some forms, the peptide selectively homes to a site of glial scar formation. In some forms, the peptide selectively homes to a site where hyaluronic acid, versican, tenascin-R, and Hapln are being deposited. In some forms, the peptide selectively homes to CSPG-rich extracellular matrix complex.

The disclosed peptides and compositions are particularly useful for targeting acute nervous system injury. Thus, in some forms, the composition near the time of the injury or during the acute phase of the injury. In some forms, the composition is administered within 10 days of the onset of the nervous system injury. In some forms, the composition is administered within 5 days of the onset of the nervous system injury. In some forms, the composition is administered within 24 hours of the onset of the nervous system injury.

Disclosed in particular are methods of selectively targeting a cargo composition to a site of acute nervous system injury in a subject, where the method involves administering the composition to a subject having an acute nervous system injury, where the composition includes a peptide and a cargo composition, where the peptide consists of the amino acid sequence CAQK (SEQ ID NO:4), where the cargo composition includes a surface molecule and cargo molecule, where the surface molecule includes a nanoparticle, where the cargo molecule is encapsulated in the nanoparticle, where the cargo molecule is a therapeutic agent, and where the therapeutic agent includes a functional nucleic acid. The composition selectively homes to a site of the nervous system injury in the subject thereby selectively targeting the cargo composition of the composition to the site of the nervous system injury.

Studies have revealed extensive molecular heterogeneity in the molecular targets accessible to circulating blood in different normal tissues. In addition, pathological lesions, such as tumors and locations of injury, impose their own changes on the accessible molecular targets. Targeting accessible molecular targets enable docking-based ('synaphic') targeting to selectively deliver diagnostics and therapeutics into a specific tissue. This approach can produce greater efficacy and diminished side effects. The targeted delivery principle has been established, particularly in cancer. It has been realized that it may be more effective to target the delivery to molecular targets accessible to circulating blood because of their accessibility. While penetration outside of the vasculature has been a problem for some such targeted diagnostics and therapeutics, the presence of injury where the targets of CAQK peptides occur provides entry points and access for the disclosed targeted peptides and compositions.

Binding in the context of a homing molecule recognizing and/or binding to its target can refer to both covalent and non-covalent binding, for example where a homing molecule can bind, attach or otherwise couple to its target by covalent and/or non-covalent binding. Binding can be either high affinity or low affinity, preferably high affinity. Examples of binding forces that can be useful include, but are not limited to, covalent bonds, dipole interactions, electrostatic forces, hydrogen bonds, hydrophobic interactions, ionic bonds, and/or van der Waals forces. This binding can occur in addition to that binding which occurs with the disclosed targeted peptides and compositions.

Also disclosed more generally are methods of selectively targeting CSPG-rich extracellular matrix complexes (extracellular matrix containing hyaluronic acid, versican, tenascin-R, and Hapln and exemplified by the matrix of cultured U251 astrocytoma cells). The method can involve administering a composition to a subject, where the composition comprises a homing molecule and a pharmaceutically acceptable carrier. The composition selectively homes to the CSPG-rich extracellular matrix complex thereby selectively targeting the CSPG-rich extracellular matrix complex.

In some forms of the method, the homing molecule can specifically bind to one or more of versican, tenascin-R, and Hapln. In some forms of the method, the homing molecule can selectively home to a site where hyaluronic acid, versican, tenascin-R, and Hapln are being deposited. In some forms of the method, the composition can be administered intravenously. In some forms of the method, the composition can be administered systemically.

In some forms of the method, the composition can further comprise a cargo composition. In some forms of the method, the cargo composition can include one or more cargo molecules. In some forms of the method, the cargo molecules can each independently be a therapeutic agent, a therapeutic protein, a therapeutic compound, a therapeutic composition, a polypeptide, a nucleic acid molecule, a small molecule, a label, a labeling agent, a contrast agent, an imaging agent, a fluorophore, fluorescein, rhodamine, a radionuclide, indium-111, technetium-99, carbon-11, or carbon-13, or combinations thereof. In some forms of the method, at least one of the cargo molecules comprises a therapeutic agent. In some forms of the method, at least one of the cargo molecules comprises a functional nucleic acid. In some forms of the method, at least one of the cargo molecules comprises a detectable agent.

1. Targets and Subjects

The disclosed compositions are targeted and can home to sites of nervous system injury. As used herein, "nervous system injury" refers to an injury or damage to any part of the nervous system. Different parts of the nervous system can be injured, which injuries can be referred to by the part of the nervous system that is injured. Thus, for example, central nervous system injury, peripheral nervous system injury, brain injury, spinal cord injury, neural injury, and neuronal injury refer to injury of the central nervous system, peripheral nervous system, brain, spinal cord, nerves, and neurons, respectively. Some nervous system injuries can be distributed, such as neurodegenerative diseases (such as Alzheimer's disease and Parkinson's disease), demyelinating diseases (multiple sclerosis is an example), and autoimmune diseases that affect nerves or parts or components of the nervous system. Nervous system injury can be acute or chronic.

A nervous system injury can be from numerous causes, including accident, disease, and condition. The disclosed peptides, compositions, and methods are most useful for acute nervous system injuries, which can occur from the same causes. As used herein, an acute injury refers to an injury that occurs from a sudden event or change in condition. For example, a traffic accident, gunshot, fall, stroke, and heart attack can all be the cause of an acute injury, including an acute nervous system injury. As an example, acute brain injury can be caused by, for example, an open head injury, a closed head injury, a deceleration injury, hypoxia, and stroke.

Open head injuries can result from bullet wounds, crushing, penetrating wounds, etc. The damage tends to be focal and to involve penetration of the skull. Closed head injuries can result from falls, motor vehicle crashes, etc. Damage can be both focal and diffuse and the effects tend to be broad and diffuse. There is no penetration of the skull in closed head injuries. Deceleration injuries tend to cause diffuse axonal injury. Deceleration injuries tend to occur because of differential movement of the skull and the brain when the head is struck. This can result in direct brain injury due to diffuse axonal shearing, contusion, and brain swelling. Diffuse axonal shearing can occur when the brain is slammed back and forth inside the skull it is alternately compressed and stretched because of the gelatinous consistency. If the impact is strong enough, axons can be stretched until they are torn, resulting in axonal shearing. Hypoxia of brain tissue can be caused by a reduction in oxygen in the blood. Hypoxia can be caused by, for example, heart attacks, respiratory failure, drops in blood pressure, and a low oxygen environment. Stroke of brain tissue can be caused by interruption of blood flow to the brain or part of the brain or by, for example, vascular blockage or bleeding.

Glial scar formation (gliosis) is a reactive cellular process involving astrogliosis that occurs after injury to the central nervous system. In the context of neurodegeneration, formation of the glial scar has been shown to have both beneficial and detrimental effects. Particularly, many neurodevelopmental inhibitor molecules are secreted by the cells within the scar that prevent complete physical and functional recovery of the central nervous system after injury or disease. On the other hand, absence of the glial scar has been associated with impairments in the repair of the blood brain barrier. Glial scars are composed of several components: reactive astrocytes, microglia, endothelial cells, fibroblasts, and basal membrane. Relative to the disclosed peptides, compositions, and methods, the basal membrane is the most significant because the histopathological extracellular matrix making up the basal membrane includes the target of CAQK peptides.

A main target of the disclosed peptides and compositions is a CSPG-rich protein-carbohydrate extracellular matrix complex that is that is rich in chondroitin sulfate proteoglycans (CSPGs) and is produced in nervous system injuries. These CSPG-rich extracellular matrix complexes (also referred to herein as CR-ECM and CSPG-rich complexes) are the binding and homing target of the disclosed CAQK peptides. In this regard, the CSPG-rich complexes contain the molecules/structures to which the disclosed CAQK peptides bind. The CSPG-rich extracellular matrix complexes include a number of proteins and carbohydrate polymers that define the complex. Although different ECM have common components and features, the various forms of ECM are characterized by specific proteins and carbohydrate polymers. The CSPG-rich extracellular matrix complexes produced in nervous system injuries include components such as hyaluronic acid, around which CSPGs assemble. Significant CSPGs present in CSPG-rich extracellular matrix complexes produced in nervous system injuries include phosphacan, neuron-glial antigen 2 (NG2), and members of the lectican family of CSPGs: aggrecan, brevican, neurocan, and versican. Also present in CSPG-rich extracellular matrix complexes produced in nervous system injuries are glycoproteins such as tenascin, laminin, and fibronectin, and proteins such as hyaluronan and proteoglycan link protein (Hapln). A useful reference form of CSPG-rich extracellular matrix complexes is the matrix produced by cultured U251 astrocytoma cells. Unless the context indicates otherwise, reference to "CSPG-rich extracellular matrix complexes," "CR-ECM," and "CSPG-rich complexes" refer to the extracellular matrix characterized in this paragraph and exemplified by the matrix produced by cultured U251 astrocytoma cells and should not be considered just a generic reference to any extracellular matrix complex that is rich in or have a high amount of CSPGs.

Hyaluronic acid (HA; also called hyaluronan) is an anionic, nonsulfated glycosaminoglycan distributed widely throughout connective, epithelial, and neural tissues. It is unique among glycosaminoglycans in that it is nonsulfated, forms in the plasma membrane instead of the Golgi, and can be very large, with its molecular weight often reaching the millions (Fraser et al., *J. Intern. Med.* 242(1): 27-33 (1997)). Hyaluronic acid is one of the chief components of the extracellular matrix.

Versican is a large extracellular matrix proteoglycan that is present in a variety of human tissues. It is encoded by the VCAN gene (Iozzo et al., *Genomics* 14(4):845-51 (1992)). Versican is a large chondroitin sulfate proteoglycan with an apparent molecular mass of more than 1000 kDa. In 1989, Zimmermann and Ruoslahti cloned and sequenced the core protein of fibroblast chondroitin sulfate proteoglycan (Zimmermann and Ruoslahti, *EMBO J.* 8(10): 2975-81 (1989). They designated it versican in recognition of its versatile modular structure. Versican belongs to the lectican protein family, with aggrecan (abundant in cartilage), brevican and neurocan (nervous system proteoglycans) as other members. Versican is also known as chondroitin sulfate proteoglycan core protein 2 or chondroitin sulfate proteoglycan 2 (CSPG2), and PG-M.

Phosphacan, one of the principal proteoglycans in the extracellular matrix of the central nervous system, is implicated in neuron-glia interactions associated with neuronal differentiation and myelination. Although phosphacan occurs in the CNS as a large CSPG (>800 kDa) (Faissner et al., *J. Cell Biol.* 126:783-799 (1994)); it is in fact a secreted splice variant of an even larger transmembrane receptor protein tyrosine phosphatase (RPTP), RPTP-β, also known as PTP-zeta). Hence phosphacan corresponds to the entire extracellular part of the long RPTP-β receptor. These proteins are characterized by a carbonic anhydrase-like (CA) domain at their extracellular N terminus.

Tenascin-R (TNR) is an extracellular matrix protein expressed primarily in the central nervous system. It is a member of the tenascin (TN) gene family, which includes at least 3 genes in mammals: TNC (or hexabrachion), TNX (TNXB), and TNR (Erickson, *Curr. Opin. Cell Biol.* 5(5): 869-76 (1993)). The genes are expressed in distinct tissues at different times during embryonic development and are present in adult tissues.

Hyaluronan and proteoglycan link protein (Hapln) links hyaluronan to versican (and other protetoglycans). The Hapln involved in the target of the CAQK peptide appears to be Hapln4 (Spicer et al., *J Biol Chem* 278(23):21083-21093 (2003)).

Laminins are high-molecular weight (~400 kDa) proteins of the extracellular matrix. They are a major component of the basal lamina (one of the layers of the basement membrane), a protein network foundation for most cells and organs. Laminins are heterotrimeric proteins that contain an α-chain, a β-chain, and a γ-chain, found in five, four, and three genetic variants, respectively. The laminin molecules are named according to their chain composition. The laminin family of glycoproteins are an integral part of the structural scaffolding in almost every tissue of an organism. They are secreted and incorporated into cell-associated extracellular matrices.

Fibronectin is a high-molecular weight (~440 kDa) glycoprotein of the extracellular matrix that binds to membrane-spanning receptor proteins called integrins. Similar to integrins, fibronectin binds extracellular matrix components such as collagen, fibrin, and heparan sulfate proteoglycans (e.g. syndecans). Fibronectin exists as a protein dimer, consisting of two nearly identical monomers linked by a pair of disulfide bonds. Insoluble cellular fibronectin is a major component of the extracellular matrix. It is secreted by various cells, primarily fibroblasts, as a soluble protein dimer and is then assembled into an insoluble matrix in a complex cell-mediated process. Fibronectin plays a major role in cell adhesion, growth, migration, and differentiation, and it is important for processes such as wound healing and embryonic development.

The CAQK peptides target and home to sites of nervous system injury due to the presence of targets for binding of the CAQK peptides. The targets are present at sites of injury where neural extracellular matrix is being produced, in particular, where CSPG-rich extracellular matrix complex (extracellular matrix containing hyaluronic acid, versican, tenascin-R, and Hapln and exemplified by the matrix of cultured U251 astrocytoma cells) is being produced after injury. Thus, the CAQK peptides can be targeted and will home to sites where CSPG-rich extracellular matrix complex is being produced. Similarly, the CAQK are also targeted and will home to sites where the particular targets of CAQK peptides, hyaluronic acid, versican, tenascin-R, and Hapln, are being deposited. In this context, "being deposited" refers to new or greater amounts of these proteins, generally as components of extracellular matrix.

The CAQK peptide can selectively home to a site of nervous system injury. The CAQK peptide can selectively home to a site of acute nervous system injury. The CAQK peptide can selectively home to a site of brain injury. The CAQK peptide can selectively home to a site of acute brain injury. The CAQK peptide can selectively home to a site of stroke injury. The CAQK peptide can selectively home to a site of acute stroke injury. The CAQK peptide can selectively bind to one or more of versican, tenascin-R, and Hapln. The CAQK peptide can selectively home to a site of glial scar formation. The CAQK peptide can selectively home to a site where hyaluronic acid, versican, tenascin-R, and Hapln are being deposited. The CAQK peptide can selectively home to CSPG-rich extracellular matrix complex. The composition can selectively home to a site of nervous system injury. The composition can selectively home to a site of acute nervous system injury. The composition can selectively home to a site of brain injury. The composition can selectively home to a site of acute brain injury. The composition can selectively home to a site of stroke injury. The composition can selectively home to a site of acute stroke injury. The composition can selectively bind to one or more of versican, tenascin-R, and Hapln. The composition can selectively home to a site of glial scar formation. The composition can selectively home to a site where hyaluronic acid, versican, tenascin-R, and Hapln are being deposited. The composition can selectively home to CSPG-rich extracellular matrix complex.

i. Traumatic Brain Injury (TBI)

TBI is a significant cause of disability and death worldwide and can result from stroke, motor vehicle accidents, sports injuries, blast injuries, assaults, and falls. Stroke in particular, is a condition that results when poor blood flow to the brain results in cell death. There are two main types of stroke. Hemorrhagic stroke occurs spontaneously due to bleeding from an aneurysm or a weakened blood vessel. Ischemia, which is the more common type of stroke, occurs due to lack of blood flow to the brain, resulting in tissue death. Inadequate blood flow can be caused by many factors such as atherosclerosis, hypoglycemia, tachycardia, hypotension, anemia, frostbite, tumors, tourniquet application, premature discontinuation of any oral anticoagulant, and sickle cell disease.

TBI causes neuronal damage, which results from both primary and secondary injury mechanisms. Primary injury involves mechanical impact and inertial forces at the time of trauma, causing cellular strain and damage to neurons, axons, glia, and blood vessels as a result of shearing, tearing, or stretching. Secondary injury can happen in minutes, but can also evolve over days and even months after initial traumatic insult, resulting from delayed biochemical, metabolic, and cellular changes that are triggered by the primary event. Physical damage compromises the blood brain barrier, leading to infiltration of inflammatory cytokines and chemokines into the brain parenchyma and initiating inflammation. During secondary injury, proteases such as calpains and caspases contribute to cell death due to necrosis or apoptosis (Loane et al., *Trends Pharmacol. Sci.* 31:596-604 (2010); Schoch et al., *Neurotherapeutics* 9:323-337 (2012)). These secondary injury cascades are thought to be responsible for the development of many of the neurological issues that arise after TBI, and their delayed nature suggests that there is a therapeutic window for pharmacological or other treatment to prevent progressive tissue damage and improve outcome (Loane et al., *Trends Pharmacol. Sci.* 31:596-604 (2010)).

ii. Glial Scarring

The glial cells of the central nervous system (CNS), which include astrocytes, microglia, oligodendrocytes and their precursors, supply both structural and physiological support, and also respond to injury or disease. Damage to the CNS can lead to glial scarring, a process that has both beneficial and detrimental effects. Ultimately, the scar functions to reestablish the physical and chemical integrity of the CNS and is central to the repair of the blood brain barrier (Faulkner et al., *J. Neurosci.* 24:2143-2155 (2004)). However, the glial scar also prevents neuronal regrowth, and is thus detrimental to the physical and functional recovery of the CNS (Silver et al., *Nat. Rev. Neurosci.* 5:146-156 (2004)).

Reactive astrocytes are produced in a process called astrogliosis, and are the main cellular component of the glial scar. Astrocytes undergo morphological changes and produce extracellular matrix, such as chondroitin sulfate proteoglycans (CSPGs), which physically and chemically inhibit axon growth. Strategies that inhibit astrogliosis or prevent the synthesis of, or degrade CSPGs have been demonstrated to relieve axon growth inhibition and improve function.

CSPGs are generally secreted from cells, and are structural components of a variety of human tissues, including cartilage. They are composed of a core protein and a sugar side chain. The core protein is generally a glycoprotein, and the side chains are glycosaminoglycan (GAG) sugar chains attached through a covalent bond. Among CSPGs that have been identified are aggrecan (CSPG1), versican (CSPG2), neurocan (CSPG3), CSPG4-6, brevican (CSPG7), CSPG8, and phosphacan. Neurocan, brevican, versican, and aggrecan all share similar N-terminal and C-terminal domains, making up the lectican family of proteoglycans. Lecticans interact with hyaluronan and tenascin-R to form a ternary complex. Aggrecan is a major component of extracellular matrix in cartilage and the function of joints, whereas Versican is widely expressed in a number of connective tissues, including those in vascular smooth muscle, skin epithelial cells, and the cells of central and peripheral nervous system. The expression of neurocan and brevican is largely restricted to neural tissues.

CSPGs play key roles in neural development and glial scar formation. They are involved in cell processes such as cell adhesion, cell growth, receptor binding, cell migration, and interaction with other extracellular matrix constituents. They also interact with laminin, fibronectin, tenascin, and collagen. CSPGs are known to inhibit axon regeneration after spinal cord injury, by acting as a barrier against new axons growing into the injury site. CSPGs play a crucial role in explaining why the spinal cord doesn't self-regenerate after an injury.

Plasticity, associated with some return of brain function in affected areas, has been attributed to down-regulation of CSPGs. Rats that were able to recover from induced stroke exhibited down-regulation of several CSPGs, including aggrecan, versican, and phosphacan (Galtrey et al., *Brain Res. Rev.* 54:1-18 (2007)). Rats that did not return any brain function did not have significant down-regulation of CSPGs. The reduction of CSPGs in rats that returned some brain function after stroke suggests that more neurological connections could be made with less CSPGs present. Medications that are able to down-regulate CSPGs may help return more brain function to stroke patients.

CSPGs have also been implicated in Alzheimer's disease and epilepsy. Although Alzheimer's disease is mostly characterized by neurofibrillary tangles and senile plaques, these features in the postmortem brains of Alzheimer's patients have indicated the presence of CSPGs as well. CSPG4 and CSPG6, both localized on the perimeter of neurofibrillary tangles and senile plaques, were found on dystrophic neurons as well. Given the inhibitory effects of CSPGs, these results suggest that CSPGs play an important role in Alzheimer's disease progression, and could be responsible for facilitating the regression of neurons around neurofibrillary tangles and senile plaques. Medications that target the CSPGs in the neurofibrillary tangles and senile plaques may help to alleviate some of the symptoms of Alzheimer's disease.

Epilepsy is a disease characterized by seizures that are caused by excessive neurological activity in the brain. Researchers have observed that CSPGs are somewhat removed from the brain in epilepsy patients. Studies have shown a decrease in phosphacan in both the temporal lobe and the hippocampus in epilepsy cases, suggesting that there CSPGs play a role in the control of axonal regrowth (Galtrey et al., *Brain Res. Rev.* 54:1-18 (2007)). In addition, brain-derived neurotrophic factor (BDNF) mRNA and protein have been shown to be upregulated in the hippocampus by seizure activity in animal models. BDNF, a protein that is primarily located in the CNS where it acts on cells in the brain and the eye, causes certain types of nerve cells to survive and grow. In the peripheral nervous system, BDNF promotes the growth of sensory and motor neurons. In the brain, BDNF is released by either a nerve cell or a support cell, such as an astrocyte, and then binds to a receptor on a nearby nerve cell. This binding results in the production of a signal which can be transported to the nucleus of the receiving nerve cell. There, it prompts the increased production of proteins associated with nerve cell survival and function. Infusion of anti-BDNF agents or use of BDNF knockout mice has been shown to inhibit epileptogenesis in animal models (Binder et al., *Growth Factors* 22:123-131 (2004)).

In addition to the conditions described above, glial scarring occurs in a variety of other conditions involving the CNS, such as Korakoff's syndrome, multiple system atrophy, prion disease, multiple sclerosis, AIDS dementia complex, vasculitis, Parkinson's disease, Amyotrophic Lateral Sclerosis (ALS), and Huntington's disease (McMillian et al., *Trends Neurosci.* 17:138-142 (1994)). In autoimmune conditions such as multiple sclerosis, myelin damage may be exacerbated by cytokines produced by both active astrocytes and microglia. This could alter blood brain barrier permeability, allowing the migration of lymphocytes into the CNS, thus amplifying the autoimmune effect (Barron, *J. Neurol. Sci.* 134:57-68 (1995)). ALS has been shown to involve reactive astrocytes through either a loss of their neuroprotective ability or through the gain of neurotoxic effects. Late stages of ALS are also characterized by significant astrogliosis and astrocyte proliferation around areas of degeneration (Verkhratsky et al., *Neurotherapeutics* 7:399-412 (2010)).

2. Treating

The disclosed peptides and compositions are useful for treating nervous system injuries. By selectively targeting nervous system injury, such as brain injury and stroke injury, sites of glial scar formation, sites where hyaluronic acid, versican, tenascin-R, and Hapln are being deposited, and CSPG-rich extracellular matrix complexes, the disclosed compositions can deliver therapeutic agents to the site where they can be most effective. The composition selectively homes to a site of the nervous system injury in the subject thereby selectively targeting the cargo composition of the composition to the site of the nervous system injury and allowing therapeutic agents in the cargo composition to act at the site of the nervous system injury.

In some forms, the nervous system injury includes a brain injury. In some forms, the peptide selectively homes to a site of the brain injury. In some forms, the brain injury includes traumatic brain injury, stroke injury, or both. In some forms, the peptide specifically binds to one or more of versican, tenascin-R, and Hapln. In some forms, the peptide selectively homes to a site of glial scar formation. In some forms, the peptide selectively homes to a site where hyaluronic acid, versican, tenascin-R, and Hapln are being deposited. In some forms, the peptide selectively homes to CSPG-rich extracellular matrix complex.

The composition can be administered by any suitable route. In some forms, the composition is administered intravenously. In some forms, the composition is administered systemically. In some forms, the composition is not administered locally.

The disclosed peptides and compositions are particularly useful for targeting acute nervous system injury. Thus, in some forms, the composition near the time of the injury or during the acute phase of the injury. In some forms, the composition is administered within 10 days of the onset of the nervous system injury. In some forms, the composition is administered within 5 days of the onset of the nervous system injury. In some forms, the composition is administered within 24 hours of the onset of the nervous system injury.

Disclosed in particular are methods of selectively targeting a cargo composition to a site of acute nervous system injury in a subject, where the method involves administering the composition to a subject having an acute nervous system injury, where the composition includes a peptide and a cargo composition, where the peptide consists of the amino acid sequence CAQK (SEQ ID NO:4), where the cargo composition includes a surface molecule and cargo molecule, where the surface molecule includes a nanoparticle, where the cargo molecule is encapsulated in the nanoparticle, where the cargo molecule is a therapeutic agent, and where the therapeutic agent includes a functional nucleic acid. The composition selectively homes to a site of the nervous system injury in the subject thereby selectively targeting the cargo composition of the composition to the site of the nervous system injury.

The disclosed methods can be most effective while the target of the CAQK peptide is present and accessible at the site of nervous system injury, at least a number of days after the onset of the nervous system injury. The effectiveness of different therapeutic agents for nervous system injuries generally also depend on their use soon after the onset of a nervous system injury. The disclosed methods of treatment generally will be performed as part of a suite of treatments relating to that cause of the nervous system injury. For example, emergency treatment for traumatic brain injuries should be started within the so-called "golden hour" following the injury. Treatment depends on the recovery stage of the patient. In the acute stage, the primary aim of the medical personnel is to stabilize the patient and focus on preventing further injury because little can be done to reverse the initial damage caused by trauma. The main treatments for the subacute and chronic states of recovery focus on rehabilitation.

In one aspect, the compositions described herein can be administered to a subject comprising a human or an animal including, but not limited to, a mouse, dog, cat, horse, bovine or ovine and the like, that is in need of alleviation or amelioration from a recognized medical condition.

The dosages or amounts of the compositions, cargo compositions, and cargo molecules are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied.

The efficacy of administration of a particular dose of the compositions, cargo compositions, and cargo molecules according to the methods described herein can be determined by evaluating the particular aspects of the medical history, signs, symptoms, and objective laboratory tests that are known to be useful in evaluating the status of a subject suffering a nervous system injury or other diseases and/or conditions. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: (1) a subject's physical condition is shown to be improved (e.g., a tumor has partially or fully regressed), (2) the progression of the disease or condition is shown to be stabilized, or slowed, or reversed, or (3) the need for other medications for treating the disease or condition is lessened or obviated, then a particular treatment regimen will be considered efficacious.

Any of the compositions can be used therapeutically and can include or be used in combination with a pharmaceutically acceptable carrier. The compositions described herein can be conveniently formulated into pharmaceutical compositions composed of one or more of the compositions in association with a pharmaceutically acceptable carrier. See, e.g., *Remington's Pharmaceutical Sciences*, latest edition, by E. W. Martin Mack Pub. Co., Easton, Pa., which discloses typical carriers and conventional methods of preparing pharmaceutical compositions that can be used in conjunction with the preparation of formulations of the compositions described herein and which is incorporated by reference herein. These most typically would be standard carriers for administration of compositions to humans. In one aspect, humans and non-humans, including solutions such as sterile water, saline, and buffered solutions at physiological pH. Other compounds can be administered according to standard procedures used by those skilled in the art.

The pharmaceutical compositions described herein can include, but are not limited to, carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The disclosed compositions are most useful for delivery systemically, and particularly for intravenous administration. However, other routes and modes of delivery are not precluded for the disclosed compositions. The manner of delivery can vary depending on whether local or systemic treatment is desired, and on the area to be treated. Thus, for example, a compound or pharmaceutical composition described herein can be administered as an ophthalmic solution and/or ointment to the surface of the eye. Moreover, a compound or pharmaceutical composition can be administered to a subject vaginally, rectally, intranasally, orally, by inhalation, or parenterally, for example, by intradermal, subcutaneous, intramuscular, intraperitoneal, intrarectal, intraarterial, intralymphatic, intravenous, intrathecal and intratracheal routes. Parenteral administration, if used, is generally characterized by injection. Injectables, the preferred form, can be prepared in conventional forms, either as liquid solutions or suspensions, solid forms suitable for solution or suspension in liquid prior to injection, or as emulsions. Another approach for parenteral administration involves use of a slow release or sustained release system such that a constant dosage is maintained. See, e.g., U.S. Pat. No. 3,610,795, which is incorporated by reference herein.

In some forms, the disclosed methods can have a therapeutic effect. In some forms, the therapeutic effect can be reducing damage of a nervous system injury. In some forms, the therapeutic effect can be increasing retention of nervous system function following a nervous system injury. In some forms, the subject can have one or more sites to be targeted, where the composition homes to one or more of the sites to be targeted. In some forms, the subject can have a site of nervous system injury, where the composition has a therapeutic effect at the site of nervous system injury.

The terms "high," "higher," "increases," "elevates," or "elevation" refer to increases above basal levels, e.g., as compared to a control. The terms "low," "lower," "reduces," or "reduction" refer to decreases below basal levels, e.g., as compared to a control.

The term "inhibit" means to reduce or decrease in activity or expression. This can be a complete inhibition of activity or expression, or a partial inhibition. Inhibition can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

The term "monitoring" as used herein refers to any method in the art by which an activity can be measured.

The term "providing" as used herein refers to any means of adding a compound or molecule to something known in the art. Examples of providing can include the use of pipettes, pipettemen, syringes, needles, tubing, guns, etc. This can be manual or automated. It can include transfection by any mean or any other means of providing nucleic acids to dishes, cells, tissue, cell-free systems and can be in vitro or in vivo.

The term "preventing" as used herein refers to administering a compound prior to the onset of clinical symptoms of a disease or conditions so as to prevent a physical manifestation of aberrations associated with the disease or condition.

The term "in need of treatment" as used herein refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that include the knowledge that the subject is ill, or will be ill, as the result of a condition that is treatable by the disclosed compositions.

As used herein, "subject" includes, but is not limited to, animals, plants, bacteria, viruses, parasites and any other organism or entity. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

By "treatment" and "treating" is meant the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, ameliorization, stabilization or prevention. The effects of treatment can be measured or assessed as described herein and as known in the art as is suitable for the disease, pathological condition, or disorder involved. Such measurements and assessments can be made in qualitative and/or quantitiative terms. Thus, for example, characteristics or features of a disease, pathological condition, or disorder and/or symptoms of a disease, pathological condition, or disorder can be reduced to any effect or to any amount.

A cell can be in vitro. Alternatively, a cell can be in vivo and can be found in a subject. A "cell" can be a cell from any organism including, but not limited to, a bacterium.

By the term "effective amount" of the disclosed compositions, peptides, cargo compositions, cargo molecules, surface molecules, etc. is meant a nontoxic but sufficient amount of the compound to provide the desired result. The term effective amount is generally used to refer to compounds and compositions that are intended to have certain effects. As discussed elsewhere herein, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation.

By "pharmaceutically acceptable" is meant a material that is not biologically or otherwise undesirable, i.e., the material can be administered to a subject along with the selected compound without causing any undesirable biological effects or interacting in a deleterious manner with any of the other components of the pharmaceutical composition in which it is contained.

EXAMPLES

Example 1. Isolation of Brain Injury Selective Peptide by Phage Display

Materials and Methods
Brain Injury Models.

All animal experiments were conducted under an approved protocol of the Institutional Animal Care and Use Committee of Sanford Burnham Prebys Medical Discovery Institute. Eight to ten week old male BL6 mice were anesthetized with 4% isoflurane (Aerrane; Baxter, UK) in 70% $N_2O$ and 30% $O_2$ and positioned in a stereotaxic frame. Using a head restraint, a 5-mm craniotomy was made using a portable drill and a trephine over the right parietotemporal cortex and the bone flap was removed. Penetrating brain injury model was used as described (Kielian et al., *J. Immunol.* 166:4634-4643 (2001); Kielian, *J. Neuroinflammation* 1:16 (2004)). Nine needle punctures using a 21 G needle were made 3 mm deep according to a 3×3 grid, spaced 1 mm in width and 1 mm in height. For traumatic brain injury, a Controlled Cortical Impact (CCI) model was used as described (Krajewska et al., *PLoS One* 6:e24341 (2011)). Mice were subjected to CCI using the benchmark stereotaxic impactor (Impact One™; myNeuroLab.com) with the actuator part mounted directly on the stereotaxic instrument. The impactor (3 mm in diameter) tip accelerated down to the 1.0 mm distance, reaching the preset velocity of 3 m/s, and the applied electromagnetic force remained there for the dwell time of 85 ms, and then retracted automatically. The contact sensor indicated the exact point of contact for reproducible results. In both models, facemask anesthesia (1-2% isoflurane in 70%/30% nitrous oxide/oxygen) was used during the entire procedure and afterwards, the scalp was closed with sutures, anesthesia discontinued, and mice were administered buprenorphine i.p. for pain control. For the first 2 hours after injury, mice were closely monitored in their cages.

In Vivo Phage Display.

Six hours after brain injury, mice were intravenously injected with 1e10 pfu of a CX7C naïve phage library, in 100 µL, of PBS. The library was allowed to circulate for 30 minutes, after which mice were anesthetized with 2.5% avertin and perfused with PBS intracardially. Brains were extracted, and the tissue surrounding the injury and the corresponding region from the contralateral side was isolated. Tissues were homogenized in LB-NP 40 (1%) and phage was processed as described (Teesalu et al., *Methods Enzymol* 503:35-56 (2012)). Briefly, recovered phages were titered and amplified in *E. coli* BLT5403 and purified for input for second round of screening. The colonies recovered from second round were sequenced using Sanger sequencing (Eton biosciences, San Diego, USA). Alternatively, after first round, the phages in the lysate were rescued by amplification in *E. coli* and peptide-encoding portion of the phage genome was sequenced using Ion Torrent high throughput sequencing.

Peptide Synthesis and Coupling.

The peptides were synthesized on a microwave-assisted automated peptide synthesizer (Liberty; CEM, Matthews, N.C.) following Fmoc/t-Bu (Fmoc:Fluorenyl methoxy carbonyl, t-Bu: tertiary-butyl) strategy on rink amide resin with HBTU (N,N,N',N'-Tetramethyl-O-(1H-benzotriazol-1-yl) uranium hexafluorophosphate (OR) O-(Benzotriazol-1-yl)-N,N,N',N'-tetramethyluronium hexafluorophosphate) activator, collidine activator base and 5% piperazine for deprotection. Fluorescein and biotin tags were incorporated during synthesis at the N-terminus of the sequence. Cleavage using a 95% TFA Trifluoro acetic acid followed by purification gave peptides with >90% purity. Peptides were lyophilized and stored at −20° C.

Animal Experiments for Skin and Liver Injury.

For liver injury model, animals were anesthetized and a midline laparotomy was performed by first cutting the skin, bluntly separating the muscle, and then lifting the peritoneum with sterile forceps. A small hole was made into the lifted peritoneum and the hole was carefully expanded (without damage to the internal organs) in both directions along the midline. Once good exposure to liver was obtained, the artery was clamped (Roboz surgical (RS-5420)) and an excision wound 2 mm in depth on the surface of one of the liver lobes was made. The clamp was removed from the artery allowing blood to flow. The incisions on peritoneum, muscle and skin were closed. The mice were then placed on a heating pad in their cage and monitored closely until they recovered from anesthesia.

For skin wounds, induction of anesthesia was done and the skin was cleaned with alcohol and betadine and four 6 or 8 mm skin biopsies were made to the back skin of the mouse. None of the skin wounds were covered or sutured closed in order to guarantee optimal and infection-free healing. To test peptide homing, FAM-labeled peptide (50 nmoles) was injected i.v. 6 hours after injury and allowed to circulate for 30 minutes. Mice were perfused intracardially with saline and organs were isolated and analyzed by immunostaining.

CLARITY Imaging of Brain.

CLARITY was performed on freshly-extracted brain tissues as described (Chung et al., *Nature* 497:332-337 (2013)). Briefly, mice were intravenously injected with FAM-labeled peptides 6 hours after brain injury. After 30-minute circulation, mice were intracardially perfused with PBS and hydrogel solution (Acrylamide (4%), bis (0.05%), VA-044 Initiator (0.25%), paraformaldehyde 4% in PBS). Following perfusion, the tissues were incubated in the hydrogel solution at 4° C. for 2-3 days. At UCSD Neuroscience Core and Light Microscopy Facility the tissues were then degased with nitrogen and incubated at 37° C. for 3-4 hours for polymerization. Samples were then passively cleared in 4% SDS solution for around 4 weeks until the tissue became transparent. Finally, the samples were washed in PBS-T for 2 days and incubated in gradient glycerol solutions: 30, 50 and 80%, about 1 day each and stored in 80% glycerol at room temperature until imaged on a confocal microscope (Leica SP5).

Results

To isolate peptides that specifically target brain injury, unilateral puncturing stab wound injuries were inflicted to the right hemisphere of adult male mice (FIG. 1A). The penetrating brain injury (PBI) resulted in rupturing of BBB visualized by selective leakage of mouse IgG into the brain parenchyma on the injured side. PBI also caused cortical tissue loss, axonal damage, and loss of myelin in the corpus callosum, and was accompanied by an increase in glysocaminoglycan deposition in the injured hemisphere.

Figure 1B:
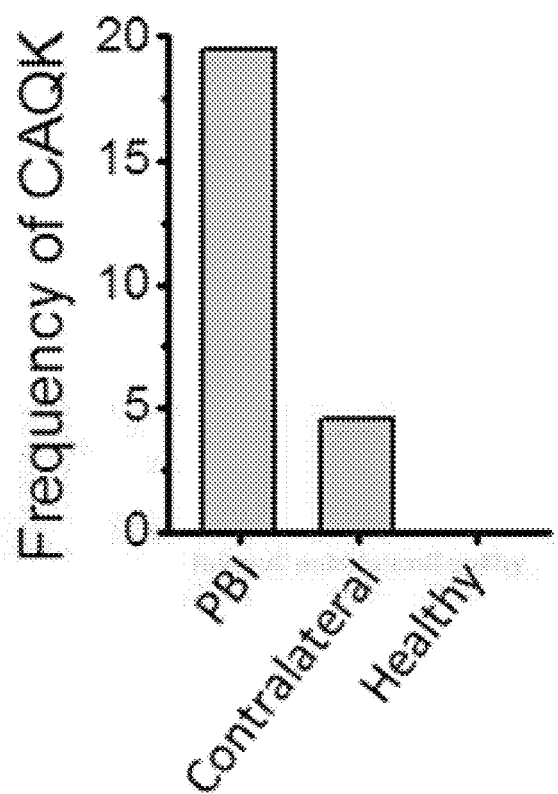
FIG. 1B is a graph showing CAQK phage frequency in brain as percentage of total phage recovered. Compared to PBI, CAQK was present at a lower percentage in the contralateral hemisphere in injured mice, and absent in healthy, control mice.

A T7 phage library that displays on the phage surface 9-amino acid cyclic peptides with the general composition of CX7C (SEQ ID NO:3) (C=cysteine; X=any amino acid) (Teesalu et al., *Methods Enzymol* 503:35-56 (2012)) was intravenously injected 6 hours after PBI. Phage was harvested 30 min after injection from the injury site and the corresponding contralateral hemisphere. Phage recovery was 10-fold higher from the injured hemisphere than from the uninjured contralateral side, indicating BBB breakdown caused by the injury. High-throughput sequencing analysis of the recovered phage pool revealed a striking enrichment of phage with the tetra-peptide insert, CAQK (SEQ ID NO:4), which comprised 22% ($1.28 \times 10^5$ pfu) of total recovered phage pool ($6.4 \times 10^5$ pfu). In addition to the truncated CAQK peptide, full-length (9aa) cyclic inserts starting with the CAQK motif were also recovered at lower frequency. A second round of biopanning increased the CAQK fraction to 83% of the total recovered phage pool. Interestingly, there was some CAQK phage recovery from the contralateral side (4%), which suggested a mild impairment triggered through the contralateral injury (FIG. 1B). No CAQK was recovered from the brain of a normal mouse injected with the phage library.

Figure 1C:
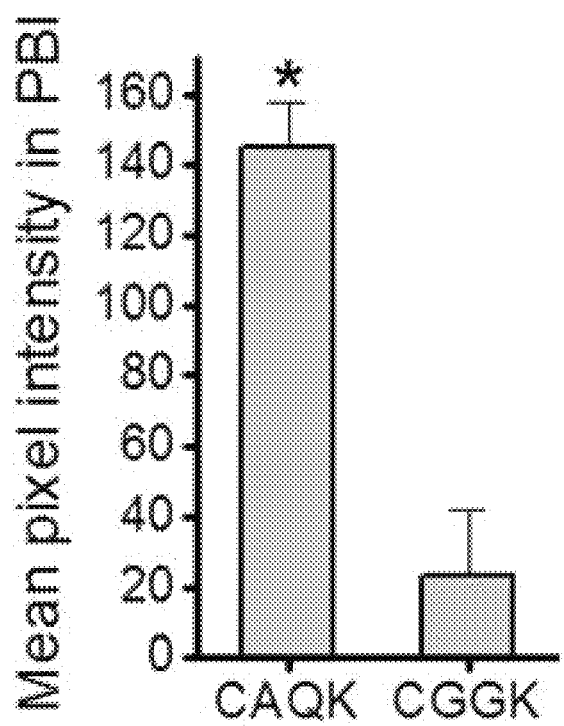
FIG. 1C is a graph quantifying fluorescence brain images of mice injected with FAM-labeled peptides six hours after PBI. Brains were perfused, isolated, and imaged under an Illumatool System (green channel). (*P<0.05, ANOVA analysis, n=6); Mean±SEM.
Figure 1D:
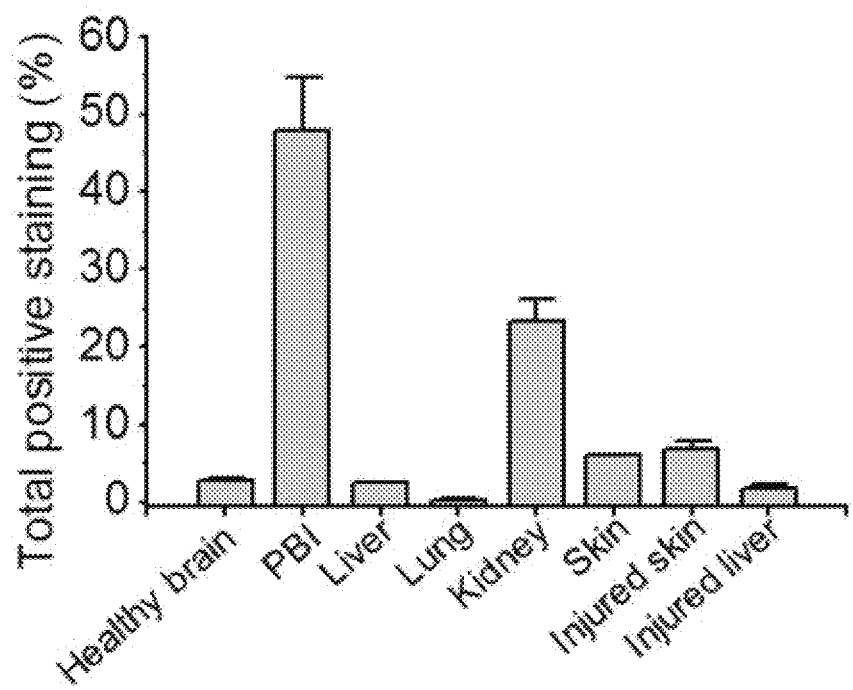
FIG. 1D is a graph illustrating selective homing of a synthetic FAM-CAQK peptide to the injured brain. The graph was compiled by quantifying and plotting signal from immunohistochemical staining for FAM.

To validate the selectivity of CAQK, a fluoresceinamine (FAM)-labeled CAQK peptide was chemically synthesized. In agreement with the phage screening results, the synthetic FAM-CAQK peptide (SEQ ID NO:5), when injected intravenously, showed selective homing to the injured brain upon macroscopic examination (FIG. 1C), and immuno-histochemical staining for the FAM-label on the peptide. A FAM-labeled control peptide (CGGK) (SEQ ID NO:7) of the same length and overall charge as CAQK yielded minimal fluorescent signal. No CAQK accumulation was observed in healthy brain or in other major tissues after 30-minute circulation, except in the kidney, which is the common route for peptide elimination from the circulation (FIG. 1D).

To investigate if CAQK targets other types of brain injuries, peptide homing was tested in a controlled cortical impact injury (CCI) model. Without penetrating injury, this model mimics cortical tissue loss, axonal injury, concussion and BBB dysfunction of TBI (Xiong et al., Nature Reviews Neuroscience 14:128-142 (2013)). CAQK homed to the injured area in the brain in this model. Binding of CAQK peptide was specific to brain injuries as no peptide accumulation was detected in perforating injuries inflicted on the liver and skin (FIG. 1D). These findings suggest that the binding epitope for CAQK peptide is specific for sites of brain injury, at least in the models tested.

Figure 1E:
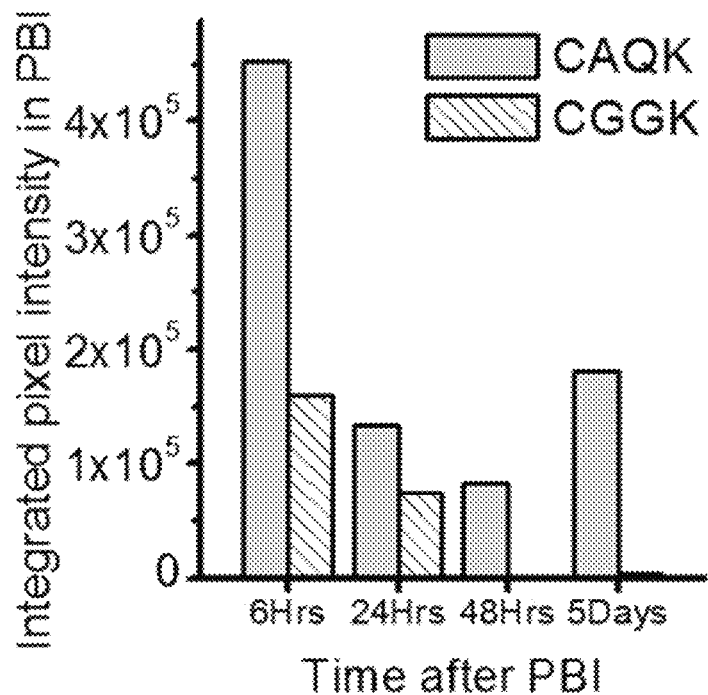
FIG. 1E is a graph illustrating a time course of CAQK accumulation in PBI.
Figure 1F:
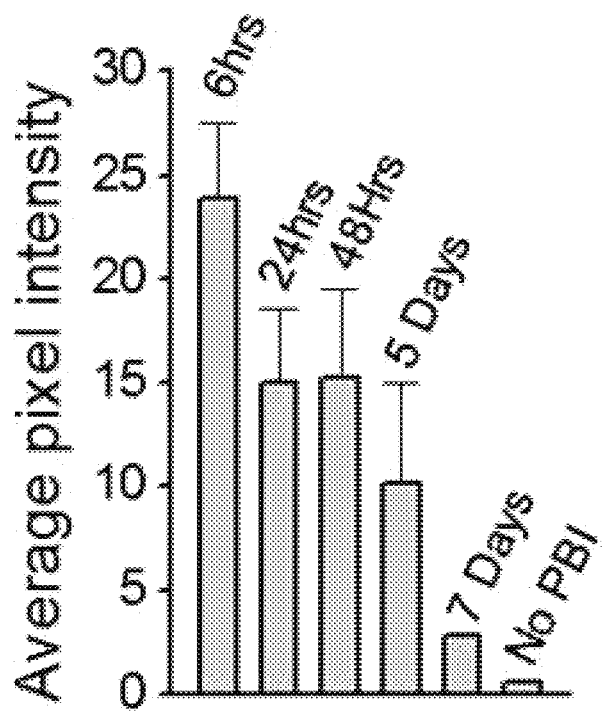
FIG. 1F is a graph illustrating blood brain barrier leakage in PBI. Brains isolated from mice after different time points after PBI were stained for mouse IgG. Total fluorescence intensity was quantified and plotted. Mean±SEM, n=3.

CAQK homing to PBI was observed up to 5 days after the injury (FIG. 1E), indicating a potential window for effective systemic CAQK-targeting. To visualize peptide accumulation across the entire brain, whole brains were processed and made transparent using the CLARITY protocol (Chung at al., Nature 497:332-337 (2013)) and FAM-CAQK was visualized in the transparent tissue. FAM-CAQK signal in the clarified brain was restricted to the injured quadrant of the brain and was higher than the signal from FAM-CGGK control. CAQK accumulated in the region of the commissural fibers of the corpus callosum and in ring-shaped cellular structures in the cortex. CAQK accumulation led to a greater retention in the injured brain, as the peptide signal was visible 3 hours after injection whereas the control peptide was completely washed out.

Example 2. CAQK Homing is Specific to Sites of Brain Injury

Materials and Methods
Silver Nanoparticles Synthesis and Targeting.

Silver nanoparticles (AgNPs) with PEG coating and peptide functionality were prepared as reported previously with some modifications (Braun et al., Nature Materials 13:904-911 (2014)). AgNPs of ~20 nm diameter were synthesized by tannic acid reduction of silver nitrate in citrate solution (Dadosh, Mater Lett 63:2236-2238 (2009)). $AgNO_3$ (252 mg) dissolved in 2.5 L water was stirred and heated to 60° C., then 50 mL water containing tannic acid (6.1 mg) and trisodium citrate dihydrate (1 g) was added. After 3 min the solution was brought to a boil for 20 min. Final optical density at 400 nm was ~10. Lipoic PEG amine (LPN, 51.9 mg, 3400 g/mol, Nanocs) was reduced in 84 mM tris-carboxylethyl phosphine (TCEP pH 7.0, Sigma) in 4.1 mL water for 3 h. AgNPs were portioned to 500 mL and heated to 50° C., then LPN solution (0.79 mL) was added, followed by 0.25 mL 0.5 M TCEP. After 30 min, the solution was cooled to room temperature (RT). Tween 20 (T20, 0.25 mL, 10% in water) and 20 mL 2 M NaCl were added, and incubated overnight at 4° C. AgNPs were concentrated 50-fold and purified by stirred cell (Millipore) with a 100 kDa membrane into 0.5×PBS with 0.005% T20 and 5 mM TCEP, then passivated with 0.03 mM N-acetyl-L-cysteine methyl ester (Sigma), and 0.10 mM tetracysteine peptide (acetyl-CCPGCC-amide, LifeTein) (SEQ ID NO:8), washed at 20 kRCF and resuspended at 300 O.D. in 0.05 M phosphate buffer with 0.005% T20. This product could be stored at least 6 months at 4° C. A bifunctional linker was reacted with the amine to introduce maleimide groups (NHS-PEG-Mal, 5 kDa JenKem USA), washed by centrifugation, and reacted with cysteine peptide (FAM-x-CAQK-NH2) (SEQ ID NOP:9) or a control thiol-containing peptide, or L-cysteine (Sigma). The product was washed in PBS with 0.005% T20 (PBST), filtered (0.22 µm), with a typical final optical density of 150 at the Ag plasmon peak of 400 nm. This concentration was estimated to be ~30 nM in AgNPs using an extinction coefficient of $5\times10^9$ $M^{-1}$ $cm^{-1}$ for spherical silver obtained from Braun et al., Nature Materials 13:904-911 (2014) (Navarro et al., The Analyst 138:583-592 (2013)). Fixed tissue sections were stained for Ag using Silver Enhance (Thermo Fischer), counterstained with Nuclear Fast Red (Sigma), and mounted in DPX (Sigma). Silver nanoparticle signal in tissue sections was quantified by Image J software by isolating grey pixels that represent Ag. For animal experiments, 35 nM of peptide-conjugated silver nanoparticles were injected intravenously in mice 6 hours after PBI. The particles were allowed to circulate for 2 hours, the mice were perfused and the brains were isolated. Silver accumulation in the brain was analyzed by silver staining autometallography with counterstaining with nuclear fast red (Sigma).

Homing Studies and Tissue Sections.

Animals were intravenously injected, six hours after injury, with 50 nmoles of peptide dissolved in PBS, and allowed to circulate for 30 minutes. Mice were perfused intracardially with saline and organs were isolated and imaged using the Illumatool Bright Light System LT-9900 (Lightools Research). Brains and organs were placed in 4% PFA at pH 7.4 overnight, washed with PBS and placed in graded sucrose solutions overnight before OCT embedding. 10 µm thick sections were cut and analyzed by immunofluorescence. For a complete histological analysis, sections were stained with the Movat pentachrome kit (American Mastertech Inc.) following the manufacturer's instructions.

Tissue Section Overlay of Silver Nanoparticles.

Overlay experiments to analyze ex vivo binding were carried out on frozen brain tissue sections following the same protocol for immunofluorescence staining described above taking the nanoparticles as if they were the primary antibody and using no secondary antibody. Peptide coated silver nanoparticles in PBS-T at a 1 nM concentration were used and the incubation time was 1 hour at 37° C. Sections were imaged with fluorescent microscopy by looking at intrinsic emission from the FAM tag on the peptide.

Results

To further characterize the binding of CAQK to the injured brain area, overlay binding experiments with silver nanoparticles conjugated with CAQK (CAQK-NPs) on mouse brain sections were carried out. CAQK-NPs showed strong binding to the injured brain sections, whereas the binding of control NPs (CGGK-NP) was negligible. Low binding of CAQK-NPs to brain sections from normal animals was observed, suggesting the presence of low levels of the peptide binding epitope in normal brain, and its elevation upon injury. Similar binding pattern of CAQK-NPs was also observed in the controlled cortical impact model. Binding specificity was confirmed by inhibiting the CAQK-NP binding with excess of free CAQK, which resulted in near complete inhibition.

Example 3. CAQK Peptide Interacts with Component of the Brain ECM

Materials and Methods
Affinity Chromatography and Proteomics.

For identifying CAQK binding proteins, mouse brains with brain injury were collected 6 hrs after injury. Using liquid nitrogen, the brains were crushed and ground into powder using a mortar and pestle. Next, brain tissue was lysed in PBS containing 200 mM n-octyl-beta-D-glucopyranoside and protease inhibitor cocktail (Roche) as described (Teesalu et al., PNAS 16157-16162 (2009)). The cleared lysate was loaded on to CAQK or control peptide (CGGK) coated Sulfolink-agarose beads (Pierce, Waltham, Mass.) and incubated at 4° C. for 3-4 hrs. The column was washed with wash buffer (75 mM octyl-beta-D-glucopyranoside and protease inhibitor cocktail in PBS) followed by washing with 0.5 mM control peptide in wash buffer to remove nonspecifically bound proteins. The bound proteins were eluted with 2 mM free CAQK peptide. The eluted factions were pooled, their protein concentration determined by using bicinchoninic acid (BCA) protein assay (Thermo Fischer) and the samples were digested using the Filter-aided Sample Preparation (FASP) method (Wisniewski et al., Nat Methods 6:359-362 (2009)). Finally, the digested samples were desalted, dried, and subjected to LC-MS/MS analysis at the Proteomics Core facility of the Sanford Burnham Prebys Medical Discovery Institute. All mass spectra were analyzed with MaxQuant software version 1.5.0.25. The MS/MS spectra were searched against the Mus musculus Uniprot protein sequence database (version July 2014). For the data in Table 1, proteins belonging to the PNN complex were identified by peptide-affinity chromatography and mass spectrometry analysis on mouse PBI brains. The LFQ intensities were derived using MAXQuant software and averaged for three technical replicates. Intensities are plotted on a $\log_2$ scale. Empty column denotes protein was not detected.

Immunofluorescence.

Frozen sections were permeabilized using PBS-Triton (0.2%), blocking was carried out using 5% blocking buffer: 5% BSA, 1% goat serum, 1% donkey serum in PBS-T. Primary antibodies were incubated in diluted (1%) blocking buffer overnight at dilutions 1/100 or 1/200 at 4° C., washed with PBS-T and incubated with secondary antibodies diluted 1/200 or 1/500 in 1% diluted buffer for one hour at room temperature, subsequently washed with PBS-T, counter-stained with DAPI 1 µg/mL in PBS for five minutes, washed with PBS, mounted using mounting media (Vector Biolabs), and imaged on a confocal microscope (Zeiss LSM-710). Staining was done using the following antibodies and reagents: Fluorescein (Invitrogen A889), Versican (abcam, ab177480), Hapln4 (R&D systems, AF4085), tenascin R (R&D systems, AF3865), WFA (Sigma, L1516), CSPG (Sigma, C8035), NG2 and olig2 (gift from Dr. William Stallcup at SBPMDI), GFAP (Dako, Z0334) and MBP (Millipore—MAB386).

Phage Binding to ECM.

Cells grown as confluent monolayer in a 96-well plate were gently removed by an enzyme free cell dissociation buffer (Thermo Fisher Scientific) and plates blocked with 200 µL of 0.5% bovine serum albumin (BSA) in PBST for 1 h at 37° C. Phage was incubated in the plate at 4° C. for overnight and unbound phage was removed by washing 3 times with 200 µL of PB ST. The bound phage was detected by incubating with an in-house generated anti-T7 phage antibody for 1 hour at 4° C. Following washing, horseradish peroxidase (HRP)-labeled anti-rabbit IgG (Sigma-Aldrich) was diluted 1:1000 in PBS, and 100 µL was added to the wells, followed by 30 minute incubation at room temperature and washing 3 times. Next, 100 µL of OPD silver and gold substrate (Sigma-Aldrich) was added to the wells and incubated at room temperature until visible color was observed (<30 min). Adding 50 µL of 1M $H_2SO_4$ stopped the reaction and the plate was read at 495 nm (FlexStation 3 Reader, Molecular Devices, Sunnyvale, Calif., USA). For enzymatic digestion, chondroitinase ABC (2 U/ml, Sigma) or hyaluronidase (500 IU/ml) was added to the plate for 3 hours at 37° C. The plate was then washed with PBST three times before incubation with phage.

Results

To identify the potential protein targets of CAQK in the brain tissue, mass spectrometry proteomics analysis was performed of proteins separated from extracts of injured brain by affinity chromatography on immobilized peptides. Table 1 shows a comparison of proteins in eluates from CAQK and control (CGGK) columns. Among the large number of proteins identified, peptides prominent in the CAQK column eluates belonged primarily to the lectican family of chondroitin sulfate proteoglycans (CSPGs (Ruoslahti, Glycobiology 6:489-492 (1996))). These included versican, associated proteins tenascin-R and the hyaluronan and proteoglycan link protein (Hapln). Versican and Hapln4 were exclusively present in the CAQK column eluates. In normal brain, lectican sulfate proteoglycans form extracellular matrix (ECM) complexes known as perineuronal nets around neuronal surfaces (PNN) (Kwok et al., Int. J. Biochem. Cell Biol. 44:582-586 (2012)), and the expression of some of these lectican proteoglycans is upregulated at sites of CNS injury (Asher et al., J. Neuroscience 22:2225-2236 (2002); Lau et al., Nat. Rev. Neuroscience 14:722-729 (2013)).

TABLE 1

CAQK Binds to Brain ECM Proteins.

| Protein Name | UniProt ID | Gene Name | $\log_2$ LFQ intensity | |
|---|---|---|---|---|
| | | | CGGK column | CAQK column |
| Versican core protein | Q62059 | VCAN | — | 25.98 |
| Hyaluronan and proteoglycan link protein 4 | Q80WM4 | HAPLN4 | — | 19.84 |
| Tenascin-R | Q8BYI9 | TNR | 24.14 | 26.71 |

Figure 2:
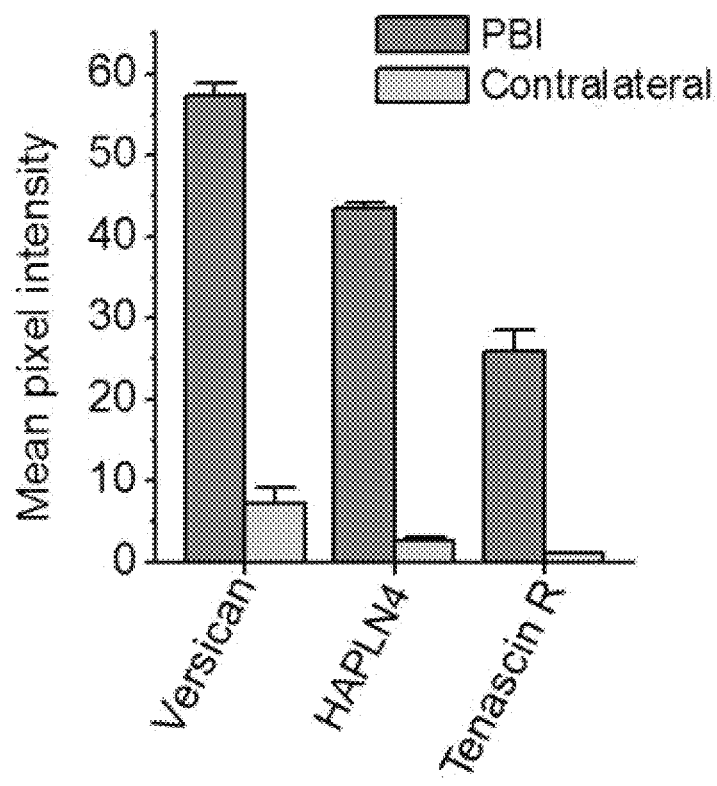
FIG. 2 is a graph showing protein expression of PNN components in PBI brain. Frozen sections of perfused mouse brains six hours after PBI were immunostained and analyzed by confocal microscopy. The graph shows quantification of immunofluorescence of versican, Hapln4 and tenascin R in injured and contralateral hemispheres in PBI brain. Signal intensity was quantified by taking the integrated pixel intensity in the red channel of three images. Mean±SEM.

The increase in expression of ECM-associated CSPGs at sites of brain injury was confirmed by immunostaining. Versican, tenascin-R, and the hyaluronan and proteoglycan link protein (Hapln4), all of which are components of the brain ECM complex upregulated following an injury, showed high expression in the injured but not the uninjured hemisphere of the brain (FIG. 2). The signal from intravenously injected CAQK co-localized with versican, tenascin-R and Hapln4. The peptide signal also co-stained with WFA (Wisteria floribunda agglutinin) lectin, a marker for PNNs. At the cellular level, FAM-CAQK prominently accumulated at mature oligodendrocytes identified by expression of the APC (Adenomatous polyposis coli) marker. In several instances, the CAQK binding pattern followed elongated cells that aligned in the direction of the callosal axons. Only a few isolated Olig-2 and NG2-positve cells, most likely oligodendrocyte progenitor cells, bound the peptide. No CAQK was detected in or around other glial cell populations, including astrocytes (GFAP+) and microglia. Collectively, these data suggest that the binding molecule (receptor) for CAQK peptide is present in the perineuronal net (PNN) complex that is upregulated in brain injuries.

Figure 3A:
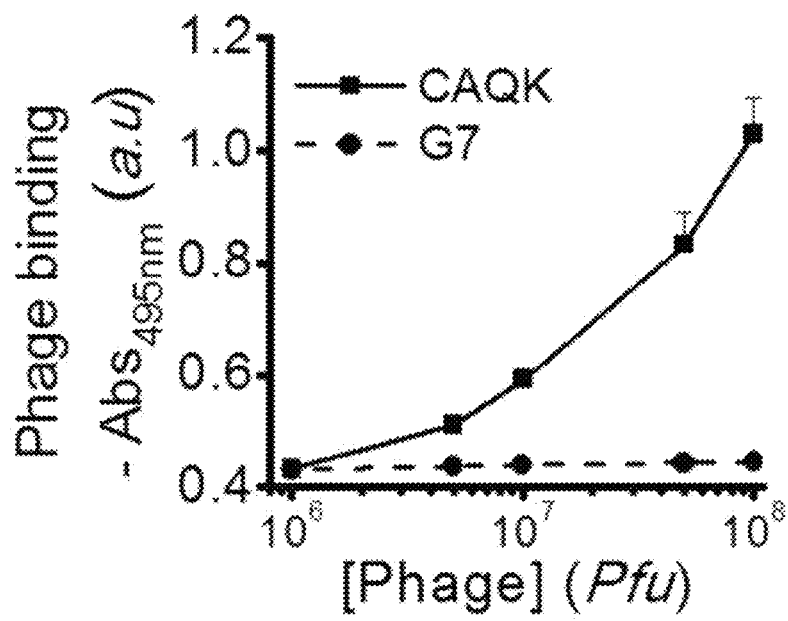
FIGS. 3A-3C are graphs illustrating colocalization of CAQK with chondroitin sulfate in PBI.
Figure 3B:
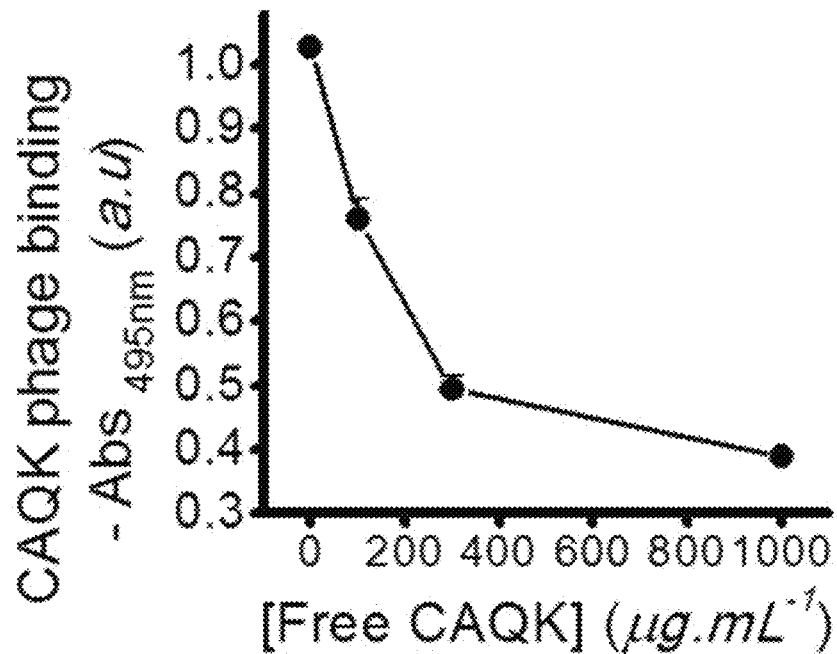
Figure 3C:
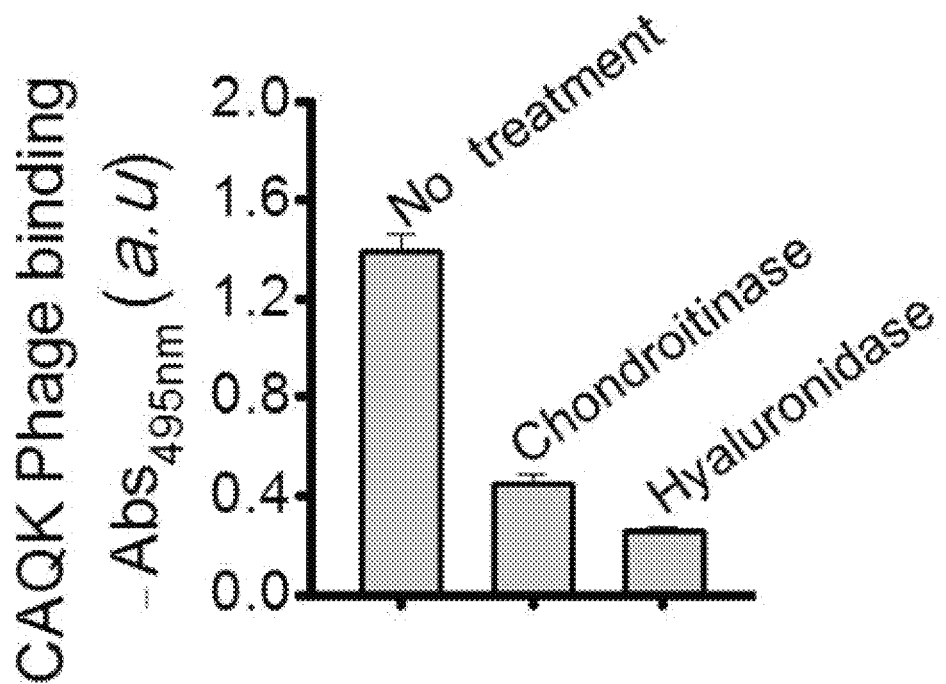
Figure 3D:
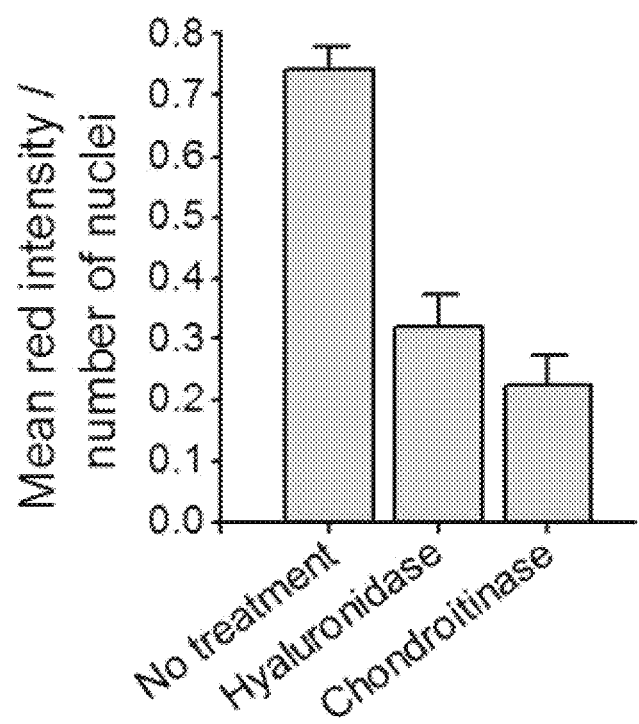
FIG. 3D is a graph showing versican expression in U251 cells. U251 cells grown as confluent monolayer were stained for versican expression and analyzed by immunofluorescence after no treatment or treatment with hyaluronidase (50 U/ml) or chondroitinase ABC (3 U/ml) for 1 hour at 37° C. Cells were counterstained with DAPI. Versican was quantified and plotted in the bar graph. Representative of three experiments is shown.

To explore further the association of CAQK with the PNN complex, in vitro binding of CAQK phage to ECM produced by U251 human astrocytoma cells was tested. These cells express high levels of versican and other members of the brain ECM (Dours-Zimmermann et al., *J. Biol. Chem.* 269:32992-32998 (1994)), which suggests that these cells are activated in culture. CAQK phage showed significantly higher binding to the U251 ECM than a control phage (FIG. 3A). In addition to providing further evidence for the ECM binding of CAQK, this result indicates that CAQK recognizes the human target. This is not surprising, as peptides are generally not species-specific in their binding properties (Ruoslahti, *Advanced Mat.* n/a-n/a (2012)). Binding to this ECM was specific as it was inhibited with excess free CAQK peptide. Moreover, enzymatic treatment of the ECM with chondroitinase ABC or hyaluronidase resulted in loss of versican staining (FIG. 3D) and correspondingly reduced CAQK binding. This suggests that the epitope for CAQK resides in the PNN complex formed by the CSPGs, hyaluronic acid and associated proteins (FIGS. 3B, 3C).

Example 4. CAQK as a Carrier of Diagnostics and Therapeutics to Brain Injuries

Materials and Methods

Synthesis and Functionalization of Porous Silicon Nanoparticles (PSiNPs).

Single-crystalline highly doped p-type silicon wafers (~1 m$\Omega$ cm resistivity, <100> polished, boron-doped) were purchased from Virginia Semiconductor, Inc. Porous silicon nanoparticles (PSiNPs) were prepared by electrochemical perforation etching of the silicon wafers, as described previously (Qin et al., *Part. Part. Syst. Char.* 31:252-256 (2014)). Briefly, the silicon wafer was anodically etched in an electrolyte consisting of 3:1 (by volume) of 48% aqueous HF:ethanol. Etching was carried out in a Teflon etch cell that exposed the polished silicon wafer surface, using a platinum coil counter electrode. The silicon wafer was contacted on the backside with a strip of aluminum foil. The etching waveform consisted of a square wave in which a lower current density of 50 mA/cm$^2$ was applied for 1.8 sec, followed by a higher current density of 400 mA/cm$^2$ for 0.36 sec. This waveform was repeated for 140 cycles, generating a perforated porous silicon film with alternating layers of high and low porosity. The resulting porous nanostructure was removed from the silicon substrate by applying a current density of 3.7 mA/cm$^2$ for 250 sec in an electrolyte consisting of 1:30 (by volume) of 48% aqueous HF:ethanol. The freestanding porous silicon films were then fractured to the desired size (nominally 150 nm) by ultrasonication, and the resulting nanoparticles were oxidized by immersion in aqueous borax solution to activate photoluminescence (Joo et al., *Adv. Funct. Mat.* 24:5688-5694 (2014)).

Characterization of PSiNPs.

Transmission electron microscope (TEM) images were obtained on JEOL-1200 EX II operating at 120 kV. Dynamic light scattering (DLS, Zetasizer ZS 90, Malvern Instruments) was used to determine the hydrodynamic size and Zeta potential of the nanoparticles. Photoluminescence and fluorescence spectra were obtained using a QE pro spectrometer (Ocean Optics). Concentration of siRNA was determined by measuring absorbance at 260 nm using a spectrometer (NanoDrop 2000, Thermo Fisher Scientific) based on the OD$_{260}$ standard curve of siRNA.

Peptide Conjugation and siGFP Loading to PSiNPs.

An aliquot of PSiNPs (2 mg/ml in ethanol) was mixed with 20 µL of 3-(ethoxydimethyl)-propylamine silane by vortex overnight at room temperature. The amine-terminated nanoparticles were rinsed three times with ethanol and then further reacted with 1 mL of succinimidyl carboxy methyl ester-polyethylene glycol-maleimide (10 mg/ml in ethanol) for 2 hours, followed by rinsing with ethanol and deionized water (three times each). An aqueous solution of the peptides (500 µL, 1 mg/ml, either CAQK or control) was added to the resulting nanoparticles and mixed by vortexing for 2 hours to conjugate the peptide via the free cysteine residue at the terminal group of the peptide (Cai et al., *Nat. Prot.* 3:89-96 (2008)). Peptide conjugation was confirmed by measuring fluorescence of a FAM tagged to the peptide. The amount of peptide on nanoparticles was estimated to be ~70 nmol/mg (peptide/PSiNPs). The oligonucleotide siGFP was electrostatically loaded to the positively charged porous inner structure of the nanoparticles by mixing with siRNA solution (200 µM) at 4° C. for 24 hr. The loading amount of siGFP was ~7 wt % (siGFP/PSiNP), which was determined by measuring absorbance at 260 nm. Note that the PEG linkers were attached only onto the outer surface (not the inside pores) of PSiNPs due to their large molecular weight and long chain length relative to the pore size (~12 nm). 3-(ethoxydimethyl)-propylamine silane and succinimidyl carboxy methyl ester-polyethylene glycol-maleimide (SCM-PEG-Mal, MW 5000) were purchased from Sigma-Aldrich and Laysan Bio, respectively, and used as received without further purification. RNase free water was purchased from Thermo Fischer (Carlsbad, Calif.). Small interfering RNA against green fluorescent protein (siGFP) was purchased from Dharmacon. The sequences for the sense and antisense strands of siGFP are: 5'-GGCUACGUCCAGGAGCGCAC-CdTdT-3' (sense) (SEQ ID NO:1) and 5'-UGCGCUCCUG-GACGUAGCCTTdTdT-3' (antisense) (SEQ ID NO:2).

In Vivo siRNA Targeting and Analysis.

Transgenic CAG-GFP mice were purchased from The Jackson Laboratory (stock #006567). Brain injuries were done as described above. Peptide-conjugated and siRNA-loaded PSiNPs (300 µg) were administered twice via tail-vein injections at 6 and 24 hours post injury (n=3). Three days after injury, mice were perfused, organs harvested and fixed for downstream analysis. The tissues were imaged under a time-gated imaging setup and the GFP expression was analyzed by researchers blinded to the experimental groups.

Gated Luminescence Imaging of Silicon Nanoparticles (GLISiN).

Gated luminescence images were acquired from a custom-built time-domain imaging system using an intensified CCD camera (iSTAR 334T, Andor Technology Ltd.), as reported (Joo et al., *ACS Nano* 9:6233-6241 (2015)). A tunable laser consisting of a tripled Nd:YAG-pumped optical parametric oscillator (Opolette 355, Opotek Inc.) were used as an excitation source at a repetition rate of 10 Hz, which was synchronized and triggered with the CCD. The Andor SOLIS software was used to control time delays and acquisition conditions and to analyze signal-to-noise ratio (SNR). Mouse tissues were placed on a black polystyrene plate, and bright field (under ambient light) and gated luminescence (under excitation with pulsed laser, $\lambda_{ex}$=410 nm) images were taken.

Human Tissue Experiments.

Formalin fixed human brain tissues were obtained from the Brain Tissue Repository maintained by the Center for Neuroscience & Regenerative Medicine (CNRM) at the Uniformed Services University of the Health Sciences (USU) in Bethesda, Md. The TBI case is from a patient with moderate TBI (automobile accident) who died at age 72. The control case is from a 63 year-old male without any neurologic diagnosis or any signs of TBI on detailed neuropathologic evaluation. Fixed tissues were cryopreserved and sectioned for overlay binding with AgNPs as described above. For immunohistochemistry, an antigen retrieval step was done prior to incubation with anti-Hapln4 and anti-versican antibodies.

Statistical Analysis.

All data represent mean value ±SEM. All the significance analysis was done using Statistica 8.0 software, using one-way ANOVA or two-tailed heteroscedastic Student's t test. The details of the statistical tests carried out are indicated in respective figure legends.

Results

Figure 4A:
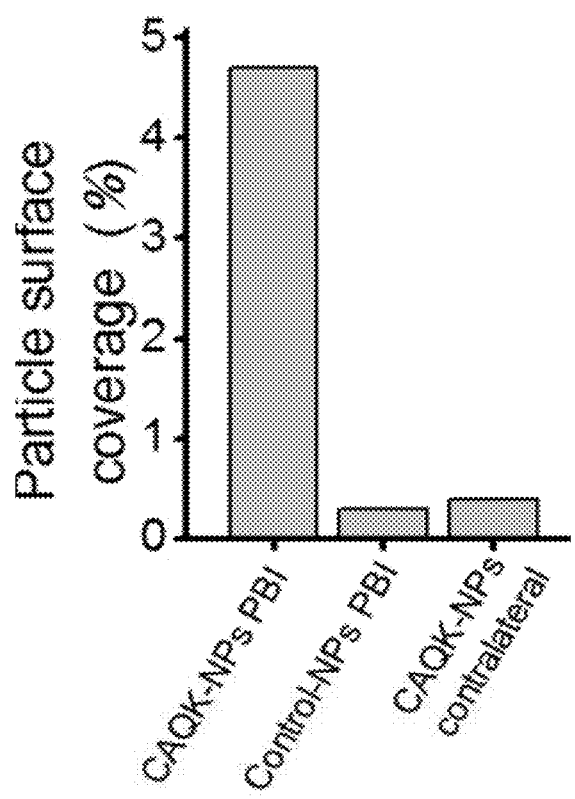
FIG. 4A is a graph illustrating CAQK-mediated delivery of silver nanoparticles to PBI. Silver nanoparticles conjugated with CAQK (CAQK-NPs) or a control peptide (control-NPs) were injected i.v. 6 hours after PBI and allowed to circulate for two hours before perfusion (n=3).

The accumulation of the FAM label attached to the CAQK peptide suggested that CAQK is capable of delivering low molecular weight compounds into sites of brain injury. To investigate further the translational potential of the CAQK targeting approach, CAQK-mediated delivery to brain injury of nanoparticles (NPs) was first examined as a model of both an imaging agent and a drug carrier. CAQK-conjugated, silver NPs (mean diameter—20 nm), administered intravenously, showed significantly greater accumulation in injured brain tissue than control NPs (FIG. 4A). The localization of CAQK-NPs was in excellent agreement with the localization of the free CAQK peptide. Thus, CAQK targeted NPs mimic the homing ability of the free peptide.

Figure 4B:
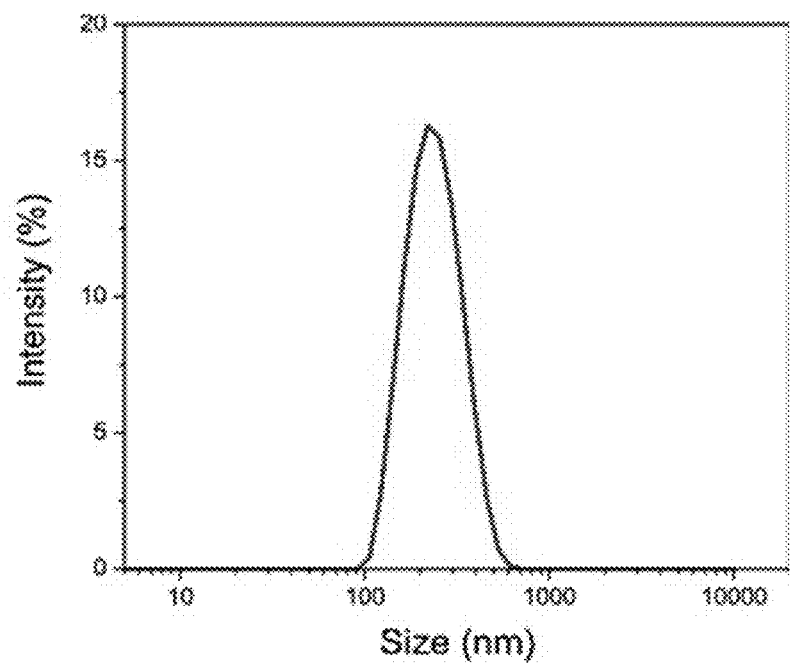
FIGS. 4B-4D are graphs showing characterization of PSiNPs.
Figure 4C:
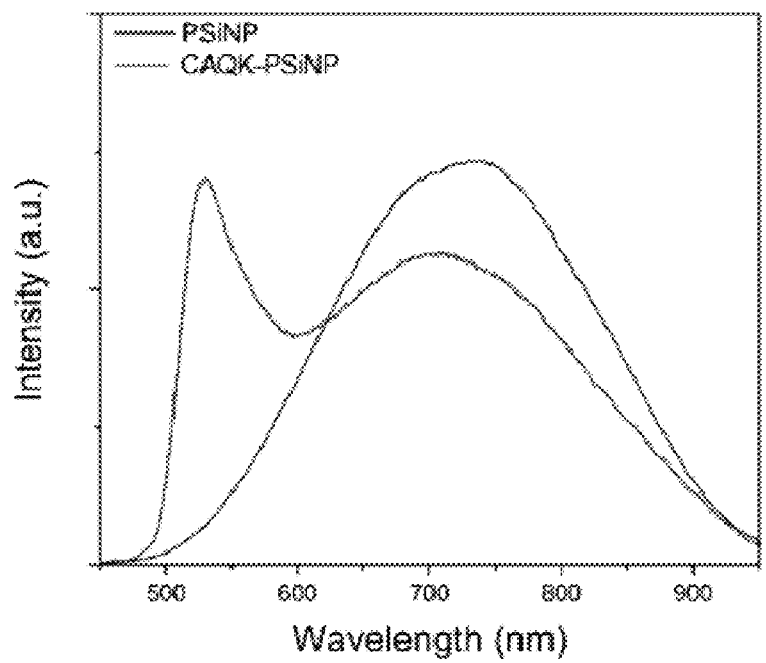
Figure 4D:
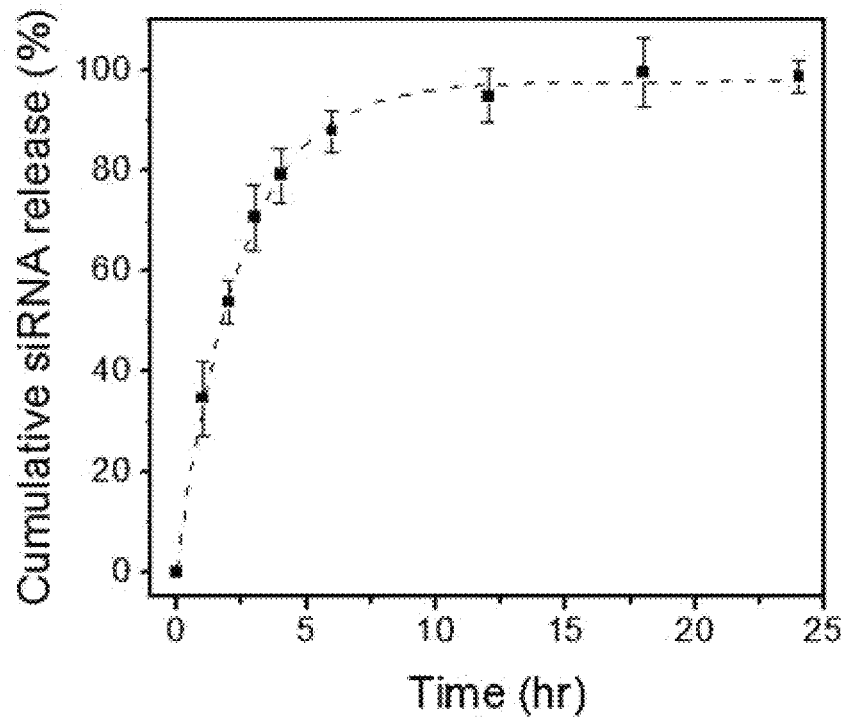
Figure 5A:
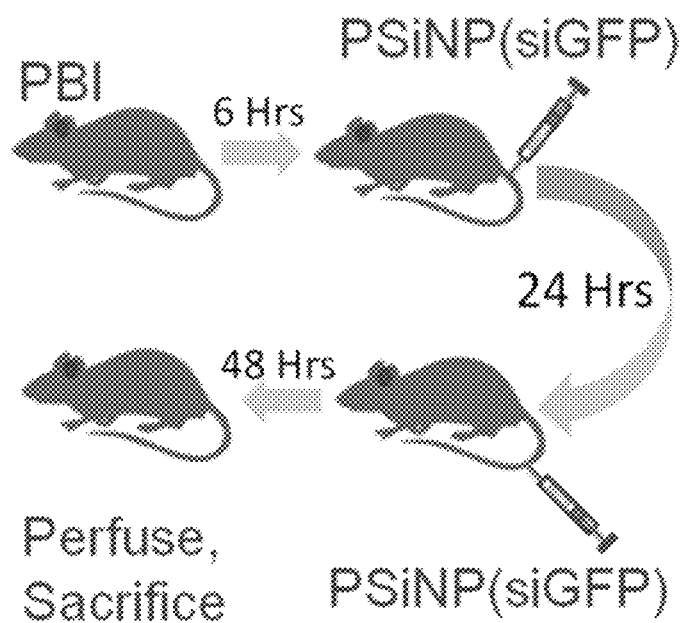
FIGS. 5A-5C illustrate siRNA delivery in PBI with CAQK-conjugated PSiNPs.
Figure 5B:
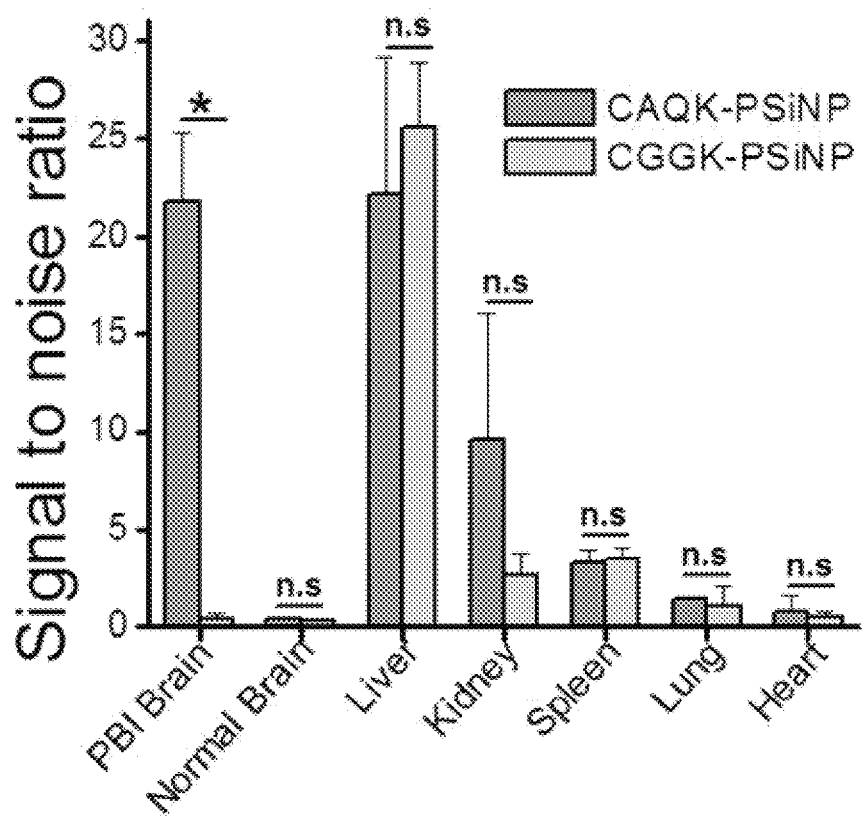
Figure 5C:
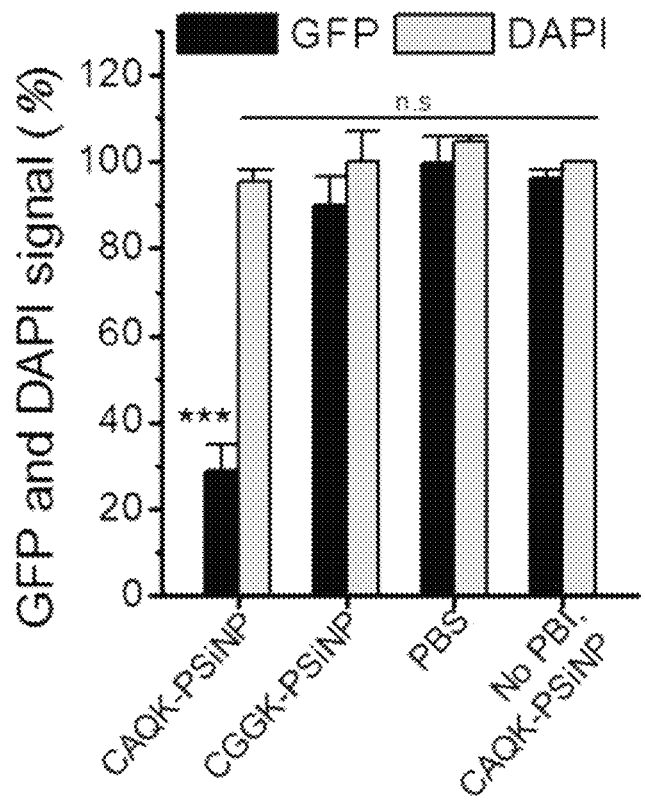

To demonstrate the versatility of the CAQK system, delivery of oligonucleotides loaded into porous silicon NPs as a carrier was tested (Park et al., *Nat. Mater.* 331-336 (2009)). The proof of concept approach was to silence local expression of green fluorescent protein (GFP) systemically expressed in transgenic mice from the CAG promoter (Okabe et al., *FEBS Lett* 407:313-319 (1997)). Therapeutic oligonucleotides were simulated by using siRNA against GFP loaded in CAQK conjugated porous silicon nanoparticles (CAQK-PSiNP) (FIGS. 4B-4D). PSiNPs were intravenously injected into the GFP mice with PBI and visualized by time-gated luminescence imaging (Joo et al., *ACS Nano* 9:6233-6241 (2015); Gu et al., *Nat. Commun.* 4:2326 (2013)), allowing quantification of their accumulation in the excised brains. The imaging showed that CAQK-PSiNPs accumulated in the injuries at markedly higher (35 fold) levels than PSiNPs coated with a control peptide. Other tissues, including regions of the brain outside the injury area, showed no significant difference in the accumulation of CAQK and control PSiNPs (FIG. 5B). Confocal microscopy on transverse cortical sections from mice injected with CAQK-PSiNP-siGFP exhibited a large void of GFP expression at the injury site, whereas brains from mice treated with control NPs did not differ from untreated brains. A 70% silencing of GFP expression was observed by targeting siGFP, whereas minimal silencing was observed with untargeted siGFP and other controls. This silencing was visible across the entire injury and not just in a particular cell type due to the gradual degradation of PSiNP and release of the siGFP over time in the injury. The gene silencing was specific for brain injury, as GFP expression remained unaltered in normal brains or in other major tissues.

Figure 6A:
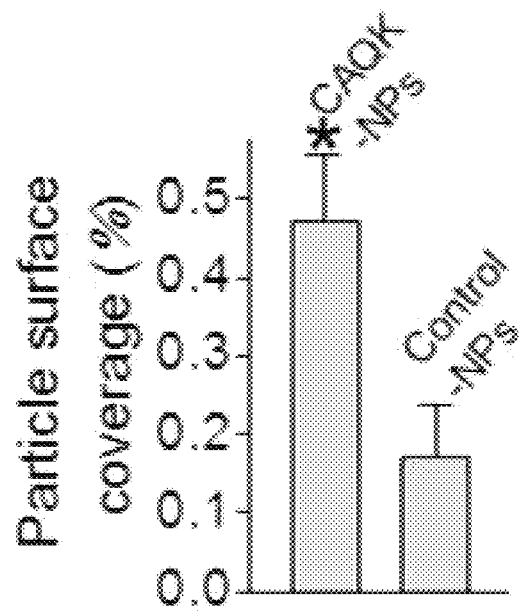
FIGS. 6A-6E are graphs illustrating CAQK binding to injured human brains.
Figure 6B:
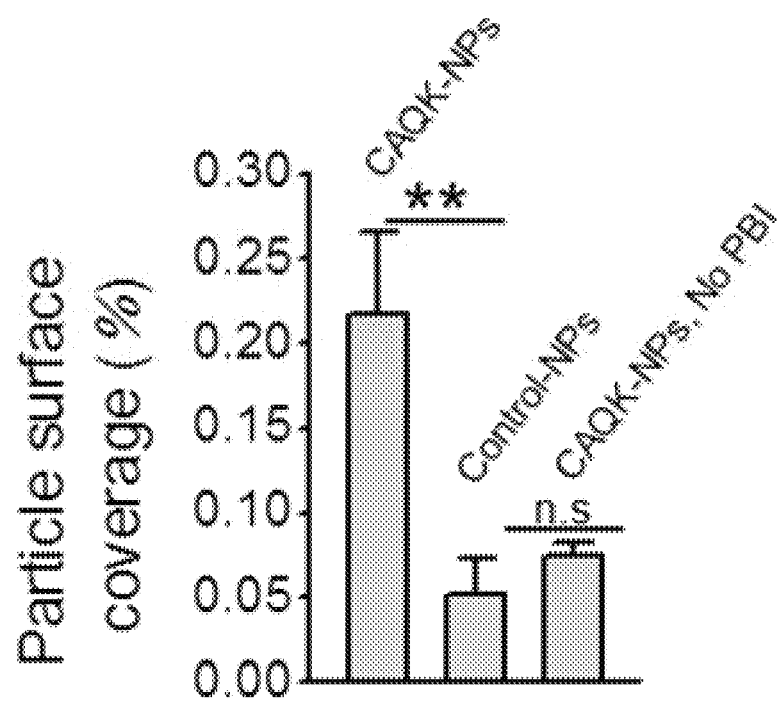
Figure 6C:
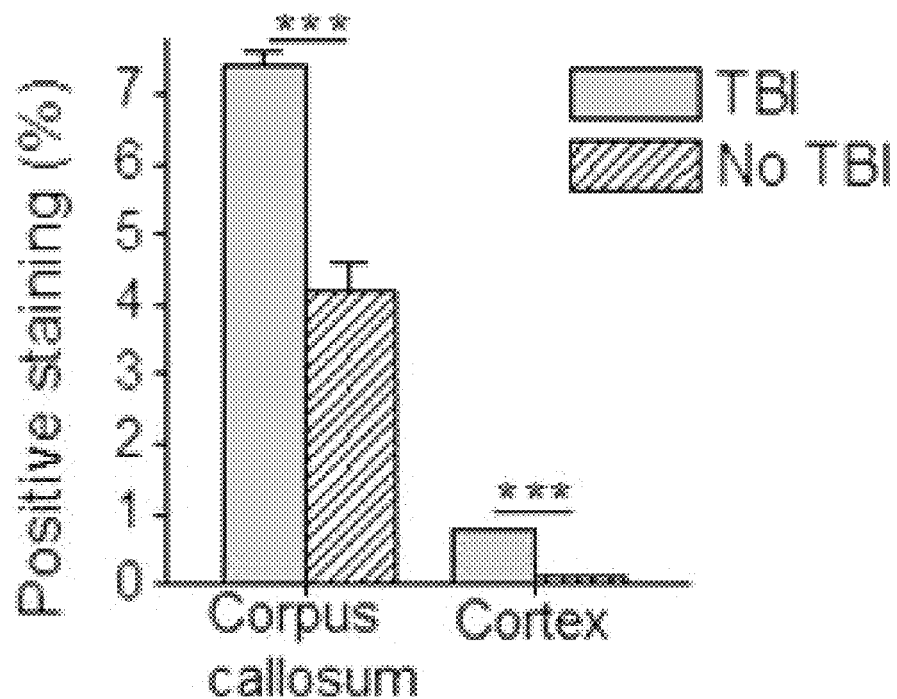
Figure 6D:
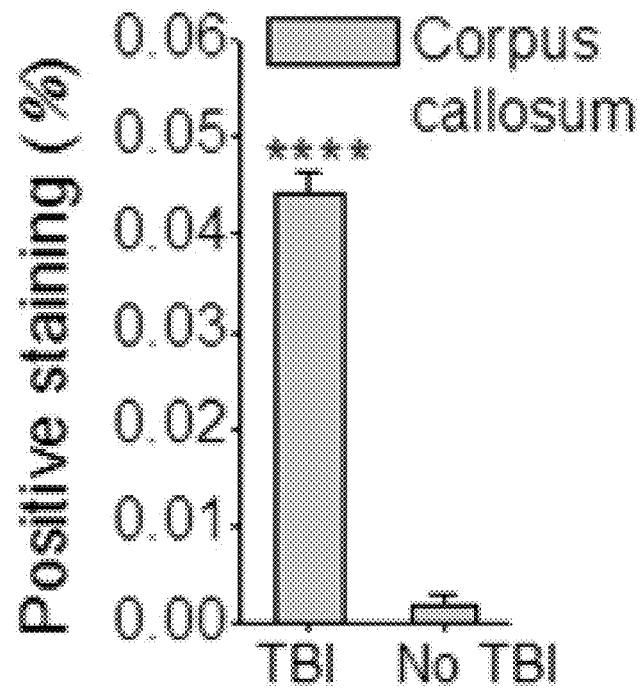
Figure 6E:
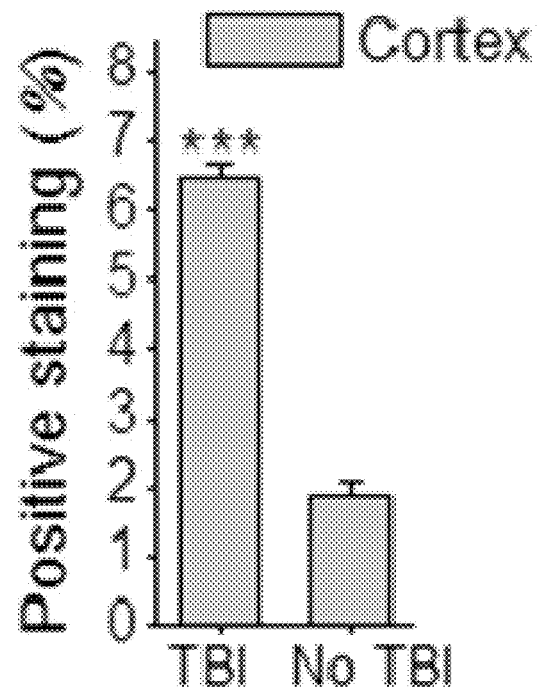

Lastly, to examine CAQK recognition of human brain injury, ex vivo binding of CAQK-conjugated silver NPs was tested on human cortical sections obtained from a head trauma patient. The CAQK-NPs showed intense binding to the injured brain sections from the cortex and the corpus callosum areas, whereas binding to normal brain sections was minimal (FIGS. 6A and 6B). Similar to the mouse brains, a significant elevation in expression of versican and Hapln4 was observed in injured brain compared to normal brain by immuno-histochemistry (FIGS. 6C-6E). These findings confirm CAQK binding to human target and support its potential utility for therapeutic application in humans.

Discussion

Two mouse models were used in this study. The penetrating brain injury model mimics gunshot or shrapnel wounds, such as the ones sustained by a warfighter. The blunt cortical impact model more generally reproduces the features of severe TBI. CAQK recognized the injuries in both models, suggesting broad utility across acute brain injuries. The fact that the contralateral hemisphere, unlike normal brain, accumulated some CAQK phage indicating that less severe injuries than the ones used here can also be targeted with CAQK. CAQK will also home to spinal cord injuries and demyelinating CNS lesions such as in multiple sclerosis to the extent they express the target of CAQK. CAQK recognition of its target in cultured human cells and in cortical sections of injured human brain has been demonstrated.

The phage screening in this study revealed a novel aspect of the in vivo screening: whereas the previous screens have probed the vasculature of the target tissue, even in the brain (Chen et al., *Nat. Med.* 15:1215-1218 (2009); Pasqualini et al., *Nature* 380:364-366 (1996); Fan et al., *Pharm. Res.* 24:868-879 (2007)), the compromised BBB integrity in brain injury allowed the phage to probe the extravascular brain tissue. Secondly, the high-throughput sequencing of the peptide-encoding inserts in the phage genome provided a technical improvement to the screening. One round of selection, as opposed to repeated rounds as previously done, provided a fingerprint of over 200,000 peptide sequences, revealing a striking enrichment of phage displaying the CAQK peptide sequence. Although a cyclic phage library was used, a library of this design contains a minority of linear peptides because stop codons occur within the random insert causing truncation of the cyclic peptide. Additionally, mutations may also change the structure of the peptide. Thus, peptides that do not conform to the general structure of the library are commonly encountered in phage screening (Hoffman et al., *Cancer Cell* 4:383-391 (2003); Simberg et al., *PNAS* 104:932-936 (2007)). The recovery of cyclic peptides containing the CAQK motif, in addition to the dominant linear CAQK peptide, suggests that CAQK motif is also active in the context of a cyclic peptide.

BBB disruption is an important contributor to secondary injury following TBI, and therapies to restore BBB functionality are under investigation for neuroprotection (Pillai et al., *J. Cerebral Flow and Metabol.* 29:1846-1855 (2009)). The localized permeability of BBB and the delayed onset of secondary injury provide a window of opportunity for therapeutic intervention. The literature (Cunningham et al., *J. Neurotrauma* 31:505-514 (2014)) and the results shown here suggest the duration of the BBB impairment is at least up to 5 days. Within this time window, affinity ligand-based (synaphic) targeting can be an effective drug delivery approach; results show as high as 35-fold enhancement in the accumulation of systemically administered imaging agents and therapeutics at and around the site of injury.

The concentrating effect of synaphic targeting is likely accounted for by two factors: the peptide can access and bind to its target that allows accumulation of the payload and causes retention at the site of injury. The impairment of the BBB allows all circulating substances to enter the injury area. And, if the peptide receptor is sufficiently abundant relative to the amount of the peptide-drug conjugate used, the binding of the peptide to the receptor can drive payload accumulation beyond what is caused by passive leakage (Hussain et al., *Scien. Rep.* 4:5232 (2014)). This is the case in brain injury, where the components of the CSPG complex are overexpressed upon an injury (Kwok et al., *Int. J. Biochem. Cell Biol.* 44:582-586 (2012)) (FIG. 2). The second important factor is the retention effect. As the drug concentration decreases in circulation, the drug is washed out of the injury area (Stewart et al., *J. Neurosci. Meth.* 41:75-84 (1992)). Peptide binding to its target can retain the drug in the injured microenvironment by minimizing this washout. Therefore, the targeting approach in this work encompasses the critical period of healing, which may provide a more lasting therapeutic effect, at least when the therapeutic action is long-acting. Notably, some oligonucleotides, which is one of the types of drugs that were successfully delivered in this work, have been shown to remain active for weeks in tissues (Bartlett et al., *Nuc. Acids Res.* 34:322-333 (2006)).

CNS injury results in formation of a CSPG-rich glial scar, which is a major barrier to regeneration (Silver et al., *Nat. Rev. Neurosci.* 5:146-156 (2004)). Strategies to prevent the accumulation of CSPGs in injury or dissolve existing deposits have been explored (Lau et al., *Nat. Rev. Neurosci.* 14:722-729 (2013)). However, site-specific delivery of the active compounds has been a challenge. The intrinsic affinity of CAQK peptide for CSPG rich areas in injured brain could be effective in directing a CSPG-reducing payload, such as the chondroitinase ABC enzyme (Hill et al., *PNAS* 109: 9155-9160 (2012)). Having successfully targeted nanoparticle payload into brain injuries indicates that the same can be accomplished with proteins, such as chondroitinase. The ability of the present approach to concentrate a payload at the site of brain injury is useful for reducing toxicity at off-target sites. An example of an existing therapeutic agent that would benefit from reduced toxicity is the neuroprotective agent Brain Derived Neurotrophic Factor (BDNF) (Nagahara et al., *Nat. Rev. Drug Disc.* 10:209-219 (2011)). It has side effects in the normal brain, which CAQK does not target. Thus, the targeting approach disclosed here has the potential of converting agents with unfavorable pharmacokinetic profile into efficient drugs.

Oligonucleotide-based drugs are a new class of drugs with great potential but hampered by delivery problems in vivo. An example is siRNA, a therapeutic modality with the desired characteristics of specificity and potency, but particularly difficult to deliver through systemic circulation. Previous studies on siRNA therapy of brain injuries have either used direct injection into the CNS space or silenced a target present in the brain endothelial cells (Fukuda et al., *Genes* 4:435-456 (2013)). The CAQK-mediated targeted delivery of siRNA reported here provides the first evidence of delivery of active siRNA into injured brain tissue from systemic circulation. A number of targets for gene silencing (such as Bcl-2 family proteins, caspases, HDAC, and PTEN) have been suggested for brain injury (Fukuda et al., *Genes* 4:435-456 (2013)). Here, CAQK-mediated siRNA delivery was accomplished by using porous nanoparticles as a carrier. Thus, these results also open up brain injuries for nanomedicine-based therapeutic approaches.

The discovery of CAQK is therapeutically useful because it can direct a payload from systemic circulation to the site of acute brain injury and retain it there for therapeutically relevant timescales. This approach provides an alternative to local delivery, which is invasive and can add complications to the injury. Moreover, the approach is applicable to human patients because CAQK recognizes the human target molecule and because the expression of the target appears to be elevated in injured human brain tissues in the same way it is in the mouse injuries.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cargo molecule" includes a plurality of such cargo molecules, reference to "the cargo molecule" is a reference to one or more cargo molecules and equivalents thereof known to those skilled in the art, and so forth.

Throughout the description and claims of this specification, the word "comprise" and variations of the word, such as "comprising" and "comprises," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. It should be understood that all of the individual values and sub-ranges of values contained within an explicitly disclosed range are also specifically contemplated and should be considered disclosed unless the context specifically indicates otherwise. Finally, it should be understood that all ranges refer both to the recited range as a range and as a collection of individual numbers from and including the first endpoint to and including the second endpoint. In the latter case, it should be understood that any of the individual numbers can be selected as one form of the quantity, value, or feature to which the range refers. In this way, a range describes a set of numbers or values from and including the first endpoint to and including the second endpoint from which a single member of the set (i.e. a single number) can be selected as the quantity, value, or feature to which the range refers. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. may include numerous options and alternatives, this should not be construed as, and is not an admission that, such options and alternatives are equivalent to each other or, in particular, are obvious alternatives. Thus, for example, a list of different cargo molecules does not indicate that the listed cargo molecules are obvious one to the other, nor is it an admission of equivalence or obviousness.

Those skilled in the art will recognize, or be able to ascertain using no more than routine experimentation, many equivalents to the specific embodiments of the method and compositions described herein. Such equivalents are intended to be encompassed by the following claims.

We claim:

1. A method of selectively targeting a cargo composition to a site of nervous system injury in a subject, the method comprising:
    administering a composition to a subject having a nervous system injury, the composition comprising a cargo composition linked or conjugated to a peptide comprising the amino sequence CAQK (SEQ ID NO:4),
    wherein the composition selectively homes to a site of the nervous system injury in the subject thereby selectively targeting the cargo composition to the site of the nervous system injury.

2. The method of claim 1, wherein the nervous system injury comprises a brain injury, wherein the peptide selectively homes to a site of the brain injury.

3. The method of claim 2, wherein the brain injury comprises traumatic brain injury, stroke injury, or both.

4. The method of claim 1, wherein the nervous system injury is a central nervous system injury, a peripheral nervous system injury, a brain injury, a spinal cord injury, a neural injury, a neuronal injury, or combinations thereof.

5. The method of claim 1, wherein the nervous system injury is an autoimmune disease that affects nerves or parts or components of the nervous system, a demyelinating disease, multiple sclerosis, or combinations thereof.

6. The method of claim 1, wherein the nervous system injury is acute.

7. The method of claim 1, wherein the nervous system injury is chronic.

8. The method of claim 1, wherein the peptide selectively binds to one or more selected from the group consisting of versican, tenascin-R, and Hapln.

9. The method of claim 1, wherein the peptide selectively homes to a site of glial scar formation.

10. The method of claim 1, wherein the peptide selectively homes to a site where hyaluronic acid, versican, tenascin-R, and Hapln are being deposited.

11. The method of claim 1, wherein the composition is administered intravenously.

12. The method of claim 1, wherein the composition is administered systemically.

13. The method of claim 1, wherein the composition is administered within 10 days of the onset of the nervous system injury.

14. The method of claim 1, wherein the composition is administered within 5 days of the onset of the nervous system injury.

15. The method of claim 1, wherein the composition is administered within 24 hours of the onset of the nervous system injury.

16. The method of claim 1, wherein the cargo composition comprises a surface molecule.

17. The method of claim 16, wherein the surface molecule comprises a nanoparticle.

18. The method of claim 1, wherein the cargo composition comprises a cargo molecule.

19. The method of claim 18, wherein the cargo molecule is selected from the group consisting of a therapeutic agent, a labelling agent, a contrasting agent, and an imaging agent.

20. A method of selectively targeting a cargo composition to a site of nervous system injury in a subject, the method comprising:
    administering a composition to a subject having a nervous system injury, wherein the composition comprises a peptide and a cargo composition, wherein the peptide comprises the amino acid sequence CAQK (SEQ ID NO:4), wherein the cargo composition comprises a surface molecule and a cargo molecule, wherein the surface molecule comprises a nanoparticle, wherein the peptide is conjugated or linked to the nanoparticle, wherein the cargo molecule is encapsulated in the nanoparticle, wherein the cargo molecule is a therapeutic agent, and wherein the therapeutic agent comprises a functional nucleic acid,
    wherein the peptide selectively homes to a site of the nervous system injury in the subject thereby selectively targeting the cargo composition to the site of the nervous system injury.

* * * * *

SEQUENCE LISTING

```
<160> NUMBER OF SEQ ID NOS: 9

<210> SEQ ID NO 1
<211> LENGTH: 23
<212> TYPE: DNA
<213> ORGANISM: Artificial Sequence
<220> FEATURE:
<223> OTHER INFORMATION: siRNA for sense strand of siGFP
<220> FEATURE:
<221> NAME/KEY: misc_feature
<222> LOCATION: (22)..(23)
<223> OTHER INFORMATION: deoxythymidine

<400> SEQUENCE: 1
ggcuacgucc aggagcgcac ctt                                                 23

<210> SEQ ID NO 2
<211> LENGTH: 23
<212> TYPE: DNA
<213> ORGANISM: Artificial Sequence
<220> FEATURE:
<223> OTHER INFORMATION: siRNA for antisense strand of siGFP
<220> FEATURE:
<221> NAME/KEY: misc_feature
<222> LOCATION: (22)..(23)
<223> OTHER INFORMATION: deoxythymidine

<400> SEQUENCE: 2
ugcgcuccug gacguagcct ttt                                                 23

<210> SEQ ID NO 3
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(8)
<223> OTHER INFORMATION: Xaa = any amino acid

<400> SEQUENCE: 3

Cys Xaa Xaa Xaa Xaa Xaa Xaa Xaa Cys
1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 4

Cys Ala Gln Lys
```

<210> SEQ ID NO 5
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-terminal FAM tag

<400> SEQUENCE: 5

Cys Ala Gln Lys
1

<210> SEQ ID NO 6
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 6

Cys Gly Gly Lys
1

<210> SEQ ID NO 7
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-terminal FAM tag

<400> SEQUENCE: 7

Cys Gly Gly Lys
1

<210> SEQ ID NO 8
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: N-terminal acetyl modification
<220> FEATURE:
<221> NAME/KEY: MISC_FEATURE
<222> LOCATION: (6)..(6)
<223> OTHER INFORMATION: C-terminal amide modification

<400> SEQUENCE: 8

Cys Cys Pro Gly Cys Cys
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE

```
<222> LOCATION: (1)..(1)
<223> OTHER INFORMATION: N-terminal FAM tag
<220> FEATURE:
<221> NAME/KEY: MISC_FEATURE
<222> LOCATION: (1)..(1)
<223> OTHER INFORMATION: Xaa = any amino acid
<220> FEATURE:
<221> NAME/KEY: MISC_FEATURE
<222> LOCATION: (5)..(5)
<223> OTHER INFORMATION: C-terminal NH2 modification

<400> SEQUENCE: 9

Xaa Cys Ala Gln Lys
1               5
```